United States Patent
Park et al.

(10) Patent No.: US 11,562,584 B2
(45) Date of Patent: Jan. 24, 2023

(54) SYSTEMS AND METHODS TO REDUCE SCATTERING IN TEMPORAL FOCUSING MULTIPHOTON MICROSCOPY

(71) Applicant: Massachusetts Institute of Technology, Cambridge, MA (US)

(72) Inventors: Jong Kang Park, Arlington, MA (US); Dushan Wadduwage, Cambridge, MA (US); Yi Xue, Cambridge, MA (US); Elly Nedivi, Newton, MA (US); Peter T. C. So, Boston, MA (US); Christopher Rowlands, London (GB); Kalen Berry, Florence, KY (US)

(73) Assignee: Massachusetts Institute of Technology, Cambridge, MA (US)

( * ) Notice: Subject to any disclaimer, the term of this patent is extended or adjusted under 35 U.S.C. 154(b) by 214 days.

(21) Appl. No.: 16/844,323

(22) Filed: Apr. 9, 2020

(65) Prior Publication Data
US 2020/0342205 A1    Oct. 29, 2020

Related U.S. Application Data

(63) Continuation of application No. PCT/US2019/015272, filed on Jan. 25, 2019.
(Continued)

(51) Int. Cl.
*G02B 21/00* (2006.01)
*G06V 20/69* (2022.01)
(Continued)

(52) U.S. Cl.
CPC .......... *G06V 20/69* (2022.01); *A61B 1/00172* (2013.01); *G01N 21/6458* (2013.01);
(Continued)

(58) Field of Classification Search
CPC .... G02B 21/0076; G02B 21/06; G02B 21/16; G02B 2207/114; G02B 21/00;
(Continued)

(56) References Cited

U.S. PATENT DOCUMENTS

| 5,034,613 A | 7/1991 | Denk et al. |
| 9,599,805 B2 | 3/2017 | Chiang et al. |

(Continued)

FOREIGN PATENT DOCUMENTS

| CN | 107505695 A | 12/2017 |
| WO | 2006/127967 A2 | 11/2006 |
| WO | 2012/135823 A1 | 10/2012 |

OTHER PUBLICATIONS

Accanto et al., Multiplexed temporally focused light shaping for high-resolution multi-cell targeting. bioRxiv. Retrieved online at: https://www.biorxiv.org/content/early/2017/11/08/216135. 25 pages. Nov. 8, 2017.
(Continued)

*Primary Examiner* — Arnel C Lavarias
(74) *Attorney, Agent, or Firm* — McCarter & English, LLP; Thomas O. Hoover; Nathan D. Harrison

(57) ABSTRACT

Systems and methods herein provide improved, high-throughput multiphoton imaging of thick samples with reduced emission scattering. The systems and methods use structured illumination to modify the excitation light. A reconstruction process can be applied to the resulting images to recover image information free of scattering. The disclosed systems and methods provide high throughput, high signal-to-noise ratio, and high resolution images that are depth selective.

42 Claims, 39 Drawing Sheets

Related U.S. Application Data

(60) Provisional application No. 62/622,692, filed on Jan. 26, 2018.

(51) Int. Cl.
*A61B 1/00* (2006.01)
*G01N 21/64* (2006.01)
*G02B 21/06* (2006.01)
*G02B 21/16* (2006.01)
*G01N 1/28* (2006.01)

(52) U.S. Cl.
CPC ......... *G02B 21/0076* (2013.01); *G02B 21/06* (2013.01); *G02B 21/16* (2013.01); *G01N 2001/282* (2013.01); *G02B 2207/114* (2013.01)

(58) Field of Classification Search
CPC .............. G02B 21/0004; G02B 21/002; G02B 21/0024; G02B 21/0032; G02B 21/0036; G02B 21/0052; G02B 21/006; G02B 21/0072; G02B 21/008; G02B 21/0084; G02B 21/36; G02B 21/361; G02B 21/365; G01N 21/6458; G01N 2001/282; G01N 21/645; G01N 21/6456; G01N 2021/6463; G01N 21/6486; G06V 20/69; G06V 20/693; G06V 20/695; A61B 1/00172; A61B 1/00163; A61B 1/00194
USPC ....... 359/385, 362, 363, 368, 369, 388, 389, 359/390, 434, 435
See application file for complete search history.

(56) References Cited

U.S. PATENT DOCUMENTS

| | | | |
|---|---|---|---|
| 9,867,525 | B2 | 1/2018 | Yew et al. |
| 10,042,150 | B2 | 8/2018 | Brown |
| 2008/0130093 | A1 | 6/2008 | Silberberg et al. |
| 2008/0192231 | A1 | 8/2008 | Jureller et al. |
| 2011/0025870 | A1 | 2/2011 | Baraniuk et al. |
| 2014/0128743 | A1 | 5/2014 | Yew et al. |
| 2015/0362717 | A1 | 12/2015 | Chen et al. |
| 2020/0284724 | A1* | 9/2020 | Dholakia ........... G02B 21/0032 |

OTHER PUBLICATIONS

Alemohammad et al., Widefield compressive multiphoton microscopy. Opt Lett. Jun. 15, 2018;43(12):2989-2992.
Candes et al., Stable Signal Recovery from Incomplete and Inaccurate Measurements. arXiv:math/0503066. 15 pages. Jun. 2005.
Choi et al., 3D-resolved fluorescence and phosphorescence lifetime imaging using temporal focusing wide-field two-photon excitation. Opt Express. Nov. 19, 2012;20(24):26219-35.
Choi et al., Improvement of axial resolution and contrast in temporally focused widefield two-photon microscopy with structured light illumination. Biomed Opt Express. Jun. 3, 2013;4(7):995-1005.
Dai et al., Adaptive compressed 3D imaging based on wavelet trees and Hadamard multiplexing with a single photon counting detector. arXiv:1709.05961. 11 pages. Sep. 15, 2017.
Ducros et al., Encoded multisite two-photon microscopy. Proc Natl Acad Sci U S A. Aug. 6, 2013;110(32):13138-43.
Escobet-Montalban et al., Wide-Field Multiphoton Imaging Through Scattering Media. arXiv:1712.07415v1. 19 pages. Dec. 20, 2017.
Escobet-Montalbán et al., Wide-field multiphoton imaging through scattering media without correction. Sci Adv. Oct. 12, 2018;4(10):eaau1338. 9 pages.
Hirano et al., Recent advancements in structured-illumination microscopy toward live-cell imaging. Microscopy. Aug. 1, 2015;64(4):237-49.
Isobe et al., Enhancement of lateral resolution and optical sectioning capability of two-photon fluorescence microscopy by combining temporal-focusing with structured illumination. Biomed Opt Express. Oct. 10, 2013;4(11):2396-410.
Kurtz et al., Application of multiline two-photon microscopy to functional in vivo imaging. J Neurosci Methods. Mar. 15, 2006;151(2):276-86.
Lum et al., Fast Hadamard transfers for compressive sensing of joint systems: measurement of a 3.2 million-dimensional bi-photon probability distribution. arXiv:1505.05431v3. 14 pages. Jul. 24, 2015.
Meng et al., Fast two-snapshot structured illumination for temporal focusing microscopy with enhanced axial resolution. Opt Express. Sep. 18, 2017;25(19):23109-23121.
Oron et al., Scanningless depth-resolved microscopy. Opt Express. Mar. 7, 2005;13(5):1468-76.
Oron et al., Temporal focusing microscopy. Cold Spring Harb Protoc. Feb. 2, 2015;2015(2):145-51.
Papagiakoumou et al., Temporal focusing with spatially modulated excitation. Optics express. Mar. 30, 2009;17(7):5391-401.
Park et al. Enhanced Axial Resolution of Wide-Field Two-Photon Excitation Microscopy by Line Scanning Using a Digital Micromirror Device. Micromachines. Mar. 9, 2017;8(3):85.
Raginsky et al., Compressed sensing performance bounds under Poisson noise. IEEE Transactions on Signal Processing. Aug. 2010;58(8):3990-4002.
Raginsky et al., Performance Bounds for Expander-Based Compressed Sensing in Poisson Noise. IEEE Transactions on Signal Processing. Sep. 2011;59(9):4139-4153.
Rodriguez et al., Resolution analysis in computational imaging with patterned illumination and bucket detection. Opt Lett. Jul. 1, 2014;39(13):3888-91.
Rodriguez et al., Resolution analysis in computational imaging with patterned illumination and single-pixel detection. Proceedings of SPIE, The International Society for Optical Engineering. Second International Conference on Applications of Optics and Photonics. Vo. 9286, 7 pages, (2014).
Rowlands et al., Wide-field three-photon excitation in biological samples. Light: Science & Applications. May 2017;6(5):e16255.
Sie et al., Fast and improved bioimaging via temporal focusing multiphoton excitation microscopy with binary digital-micromirror-device holography. J Biomed Opt. Nov. 2018;23(11):1-8.
Willett et al., Poisson Compressed Sensing. Defense Applications of Signal Processing. 6 pages. 2011.
Zhang et al., Hadamard single-pixel imaging versus Fourier single-pixel imaging. Opt Express. Aug. 7, 2017;25(16):19619-19639.
Zhang et al., Wavelets Ridgelets and curvelets for poisson noise removal. IEEE Transactions on Image Processing. 2008;17(7):1093-1108.
Zhu et al., Simultaneous spatial and temporal focusing of femtosecond pulses. Opt Express. Mar. 21, 2005;13(6):2153-9.
International Search Report and Written Opinion for Application No. PCT/US2019/015272, dated Apr. 25, 2019, 12 pages.
Choi et al.. Depth resolved hyperspectral imaging spectrometer based on structured light illumination and Fourier transform interferometry. Biomedical optics express. Oct. 1, 2014;5(10):3494-507.

* cited by examiner

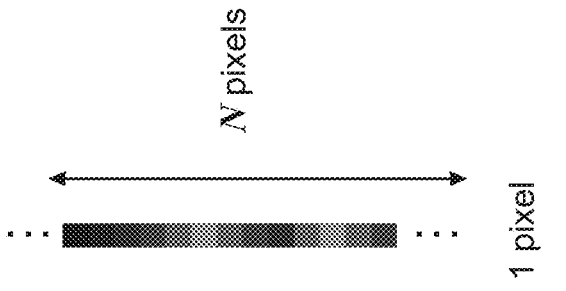
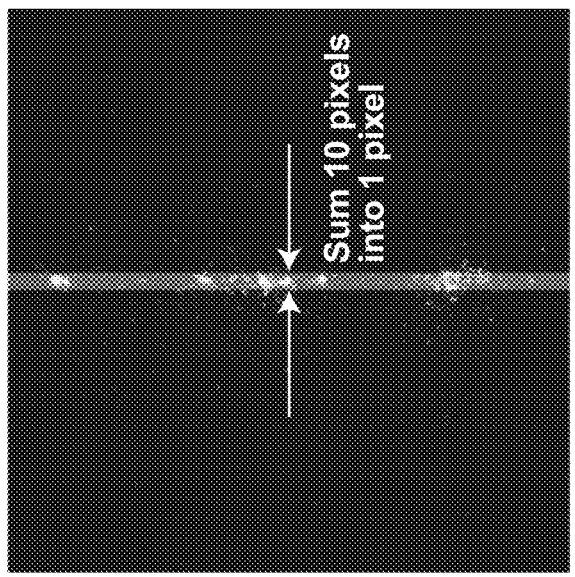
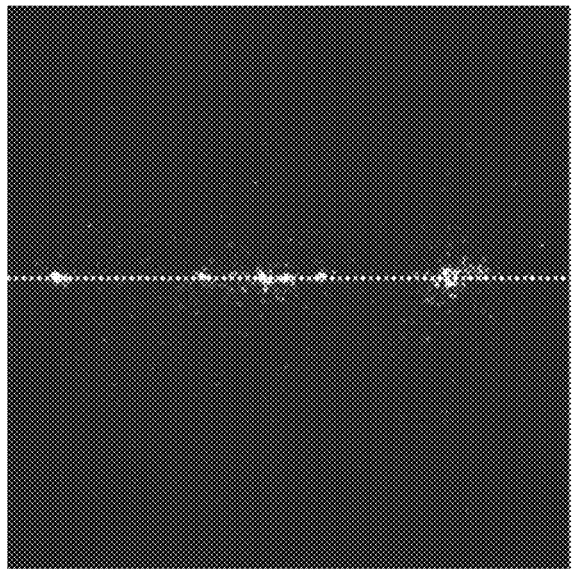
FIG. 3A
FIG. 3B
FIG. 3C

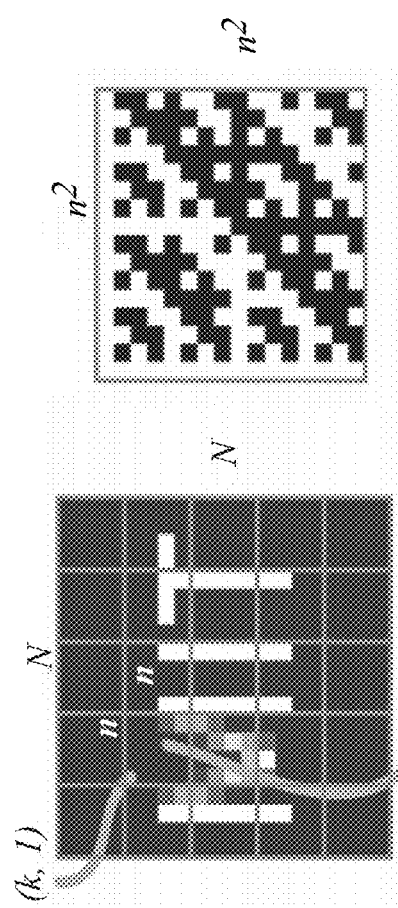
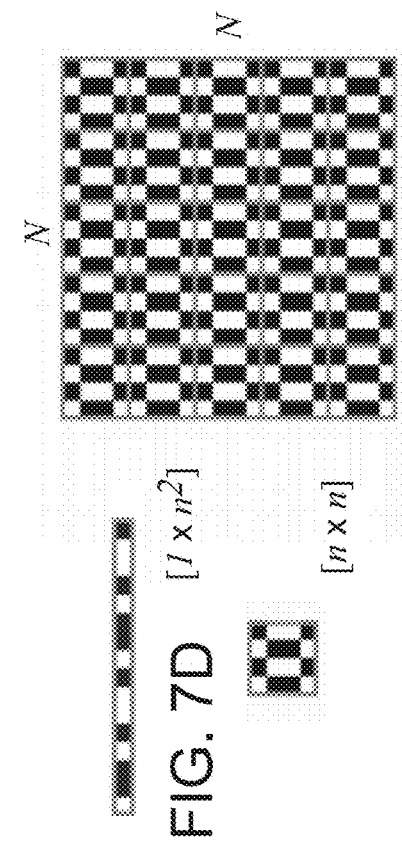
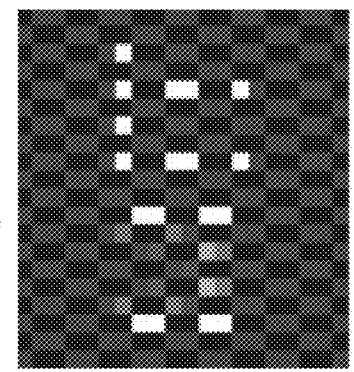
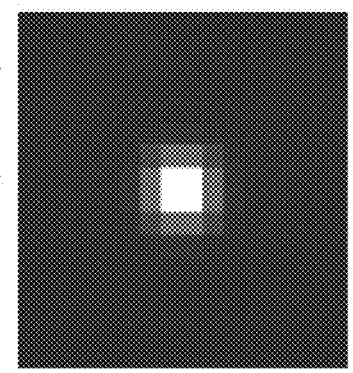
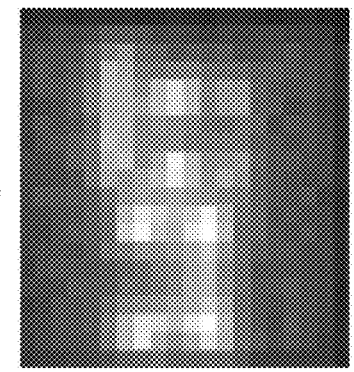
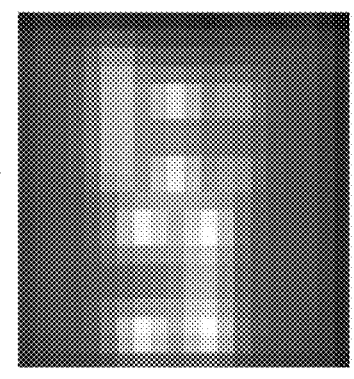
FIG. 7A  FIG. 7B  FIG. 7C  FIG. 7D  FIG. 7E
FIG. 7F  FIG. 7G  FIG. 7H  FIG. 7I $\hat{X}_{p,q}(n/2, n/2)$ $[n \times n]$ $[1 \times n^2]$ $n^2$
$n^2$

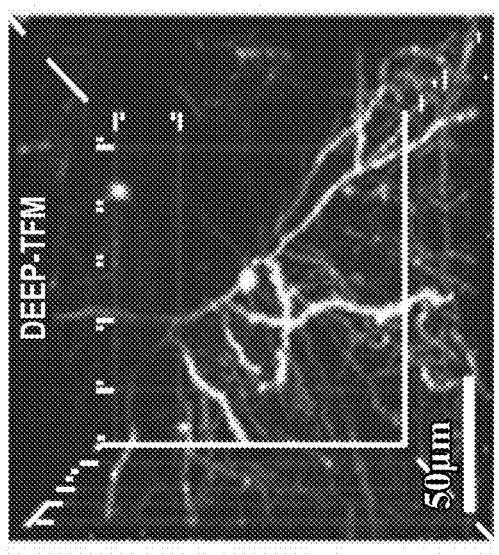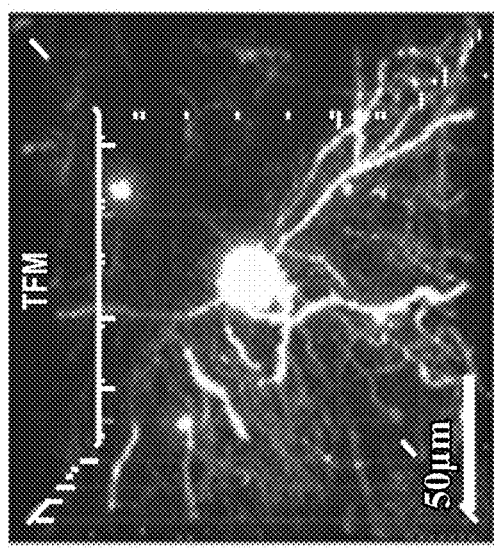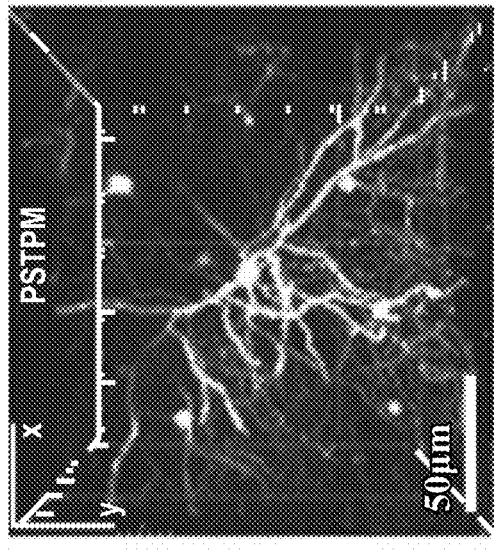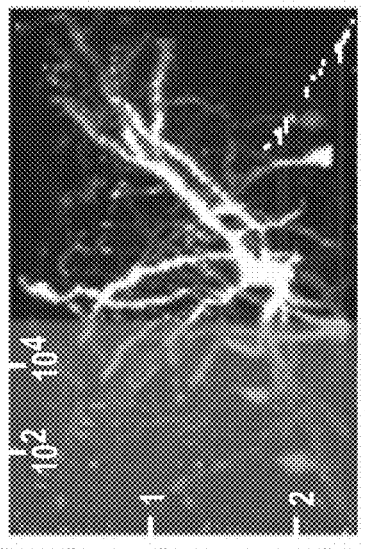

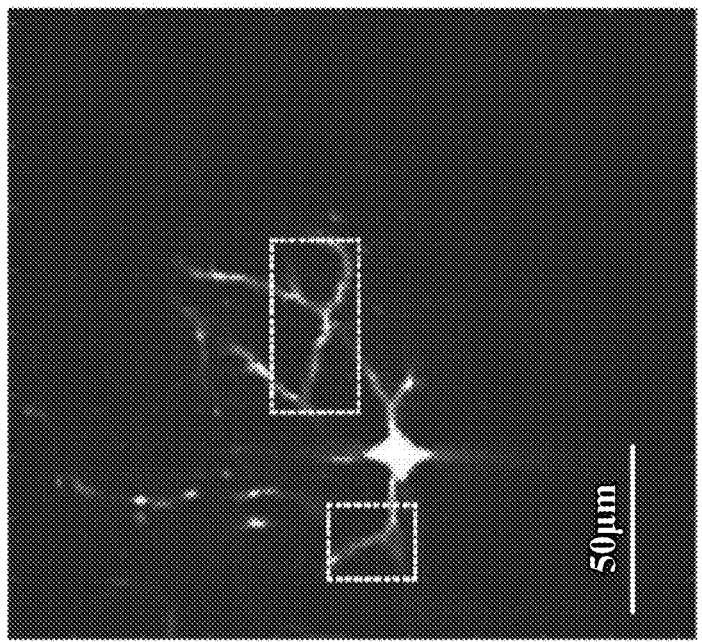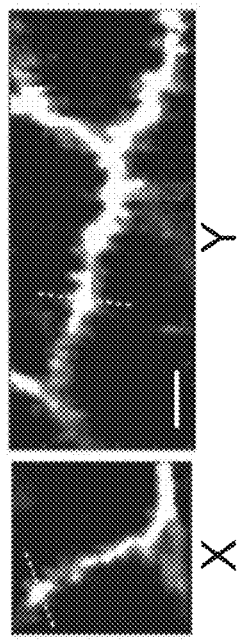
FIG. 23A
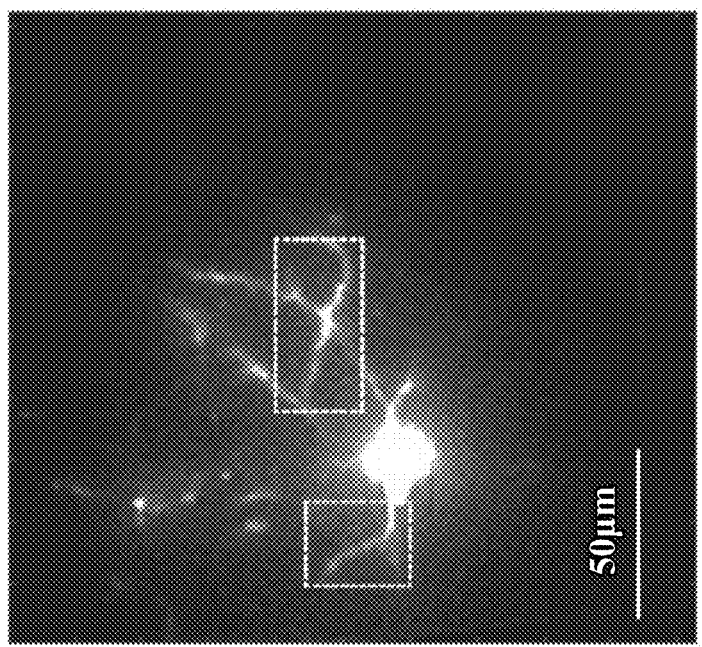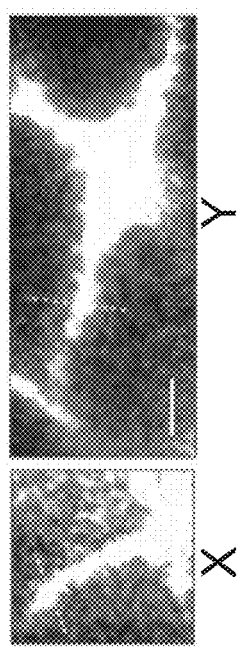
FIG. 23B

```
┌─────────────────────────────────────────────────────────────┐
│ Illuminate a sample with one or more spatially and temporally focused line beams of light │
│ to cause light emission or light scattering from a plane at a selected depth at least more │
│ than one scattering length deep (preferably at least two scattering lengths deep) within the │
│ sample.                                                      │
│ 2802                                                         │
└─────────────────────────────────────────────────────────────┘
                              ↓
┌─────────────────────────────────────────────────────────────┐
│ Acquire a first image including scattered or emitted light from the sample illuminated by │
│ the one or more scanning beams                               │
│ 2804                                                         │
└─────────────────────────────────────────────────────────────┘
                              ↓
┌─────────────────────────────────────────────────────────────┐
│ Encode the one or more spatially and temporally focused line beams with structured │
│ illumination by passing the one or more line beams through a grid or arbitrary pattern │
│ generator                                                    │
│ 2806                                                         │
└─────────────────────────────────────────────────────────────┘
                              ↓
┌─────────────────────────────────────────────────────────────┐
│ Illuminate the sample with the one or more spatially and temporally focused line beams │
│ of light including encoded structured illumination to cause light emission or scattering │
│ from the plane at the selected depth within the sample       │
│ 2808                                                         │
└─────────────────────────────────────────────────────────────┘
                              ↓
┌─────────────────────────────────────────────────────────────┐
│ Acquire a second image including scattered or emitted light from the sample illuminated │
│ by the one or more line beams including encoded structured illumination │
│ 2810                                                         │
└─────────────────────────────────────────────────────────────┘
                              ↓
┌─────────────────────────────────────────────────────────────┐
│ Extract low spatial frequency information from the first image and high spatial frequency │
│ information from the second image                            │
│ 2812                                                         │
└─────────────────────────────────────────────────────────────┘
                              ↓
┌─────────────────────────────────────────────────────────────┐
│ Combine at least the low spatial frequency information and the high spatial frequency │
│ information to reconstruct at least multiphoton image data related to the object at the │
│ selected depth                                               │
│ 2814                                                         │
└─────────────────────────────────────────────────────────────┘
                              ↓
┌─────────────────────────────────────────────────────────────┐
│ Assemble a plurality of reconstructed images acquired from different illumination angles │
│ to provide a reconstructed image having an isotropic lateral point spread function. │
│ 2816                                                         │
└─────────────────────────────────────────────────────────────┘

SYSTEMS AND METHODS TO REDUCE SCATTERING IN TEMPORAL FOCUSING MULTIPHOTON MICROSCOPY

CROSS REFERENCE TO RELATED APPLICATIONS

This application is a continuation of International Patent Application No. PCT/US2019/015272, filed Jan. 25, 2019, which claims priority to U.S. Provisional Application No. 62/622,692, filed Jan. 26, 2018, the entire contents of each application being incorporated herein by reference. This application is also related to U.S. patent application Ser. No. 16/258,307, filed Jan. 25, 2019, the entire contents of which is incorporated herein by reference.

BACKGROUND OF THE INVENTION

Since its invention, multiphoton fluorescence microscopy has become a standard imaging technique used to study biological systems in part due to its relative simplicity and intrinsic optical sectioning. Examples of multiphoton fluorescence microscopic systems are described in International Patent Publication No. WO 2006/127967, filed May 25, 2006 by P. T. C. So et al., the entire content of which is incorporated herein by reference. For a multiphoton fluorescence microscope, the effective excitation point spread function (PSF) is proportional to the square of the light intensity. This optical sectioning capability has allowed such microscopes to uncover significant new structural and functional information in biological systems in diverse areas such as early cancer detection, brain activity, and cell signaling. Despite its utility, however, conventional multiphoton microscopy is slow because the diffraction-limited size of the laser beam that scans over a region of interest. The imaging speed is limited by the speed of raster scanning due to the signal-to-noise ratio requirements for a single pixel. This limited imaging speed hinders the study of fast dynamics of biological events, such as neuronal activity, that occur at a faster time scale than the raster rate of the scanning components.

Widefield temporal focusing microscopy (TFM) was developed over the last decade to overcome this limitation. While a point scanning method achieves local excitation by spatially focusing light, temporal focusing manipulates the femtosecond pulse duration, which is compressed only in the focal plane. Outside the focal plane, the stretched pulse duration reduces beam intensity, which correspondingly lowers the multiphoton excitation efficiency and results in fewer photons originating from out-of-focus locations. Another distinction of temporal focusing is the use of a camera or pixelated detector while the point-scanning method generally uses a photomultiplier tube. Point-scanning typically collects emission photons using a photomultiplier tube (PMT) regardless of the location of the originating scattering event and assigns the detected photons to one pixel. Conversely, temporal focusing allows for recording of images using a pixelated camera instead of just a single pixel at a time. However, scattered photons can contribute to photons counted in adjacent pixels resulting in degradation of the image. This degradation limits the use of temporal focusing in deep tissue imaging applications.

SUMMARY OF THE INVENTION

Systems and methods described herein provide improved imaging of deep tissue samples using line-scanning and wide-field techniques at high acquisition speeds. In various embodiments, the systems and methods employ multiphoton imaging systems and methods including temporal focusing and fluorescence imaging. In some embodiments, the systems and methods enable imaging deep inside scattering tissue at high speeds by line-scanning or projection of structured excitation patterns into a selected depth within the material being imaged and reconstructing an image from information acquired from the detected images to limit the influence of scattering. Advantageously, the present systems and methods can provide line-scanning or wide-field multiphoton microscopy imaging at high image acquisition speeds while maintaining optical sectioning in thick samples.

The systems of the present application employ a computer system having a system controller or data processor, an image processor, one or more memories that store processing instructions, image data, sample data, etc. The active components connected to the computer system include one or more detection or pixelated cameras, light sources, lens actuation, a sample translation device that can translate the sample in one, two or three orthogonal directions, a spatial light modulator, a digital micromirror device, a diffractive optical element, one or more mirrors, and a grating or filter device that separates a light beam into one or more spectral components. A display can be used to selectively display two- or three-dimensional images of processed data.

The systems and methods described herein can be used to image sections at different depths within tissue samples using illumination wavelengths with the infrared range, for example. For certain embodiments, an illumination pattern defined, for example, by a Hadamard matrix or by one or more scan lines can be used to optically section a tissue sample of an organ such as a mouse brain using a fluorophore inserted into the tissue to target selected features. A reconstruction method can be used as described herein to process the detected image data to form images of the fluorescence distribution in the tissue.

In particular, image data is acquired at each "scan" location or projected illumination pattern. The image data can then be reconstructed based upon the prior knowledge of the projected patterns.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A-F illustrate stages of an exemplary reconstruction scheme for scattered photon reassignment in accordance with various embodiments described herein.

FIG. 7A illustrates an example imaging field of view (FOV) divided into pixel groups for modulation in accordance with various embodiments described herein.

FIG. 7B illustrates an exemplary Hadamard matrix used as a basis set for modulation in various embodiments described herein.

FIGS. 7C and 7D illustrate a representative row of the matrix in FIG. 7B and its transformation into a two-dimensional matrix.

FIG. 7E illustrates a modulation pattern created by replicating the matrix of FIG. 7D over all pixel groups.

FIG. 7F illustrates the modulation pattern of FIG. 7E as applied to the image in FIG. 7A.

FIG. 7G illustrates the scattering point spread function (PSF) for the test illustration.

FIGS. 7H and 7I shows the resulting scattered image and the detected scattered image including noise from the imaging device according to various embodiments described herein.

FIGS. 21A-21F illustrate simulated volumetric images obtained using conventional techniques and systems and methods described herein.

FIGS. 23A and 23B illustrate unreconstructed and reconstructed in vivo images using an imaging device.

FIG. 28 illustrates a flowchart for a method of performing HiLo line scanning temporal focusing microscopy according to various embodiments described herein.

DETAILED DESCRIPTION OF THE INVENTION

Systems and methods described herein provide improved multiphoton microscopic imaging methods that overcome limitations due to emission scattering. As compared to conventional point-scanning methods, the systems and methods described herein provide faster data acquisition without sacrificing signal-to-noise ratio in the final image. Systems and methods described herein spatially encode illuminated regions using structured illumination to illuminate a sample and decode spatial information in the sample from the resulting images. In some embodiments described herein, multiline angular scanning temporal focusing (masTF) can be used to increase imaging speed and reduce scattering using photon reassignment techniques. In some embodiments described herein, arbitrary pattern projecting wide-field temporal focusing (APP-WFTF) can be used to encode sections of the thick sample with arbitrary patterns to enable subsequent reconstruction. In some embodiments herein, De-scattering with Excitation Patterning—temporal focusing microscopy (DEEP-TFM) is employed that uses temporally focused, patterned excitation followed by wide-field detection with computational imaging. DEEP can be used in combination with multi-photon (e.g., two-photon, three-photon, or higher number of photons) temporal focusing (TFM) to enable imaging at multiple scattering depths within tissue. These techniques provide images of a sample at high throughput with high signal-to-noise ratio at high resolution.

Examples of temporal focusing microscopes that are compatible with embodiments of some systems and methods described herein can be found in the published article entitled "Improvement of axial resolution and contrast in temporally focused widefield two-photon microscopy with structured light illumination" by H. Choi, E. Y. S. Yew, B.

Hallacoglu, S. Fantini, C. Sheppard, and P. T. C. So, *Biomedical Optics Express*, vol. 4, no. 7, p. 995-1005, Jul. 1, 2013, "Wide-field three-photon excitation in biological samples" by Christopher Rowlands et al., *Light: Science and Applications*, vol. 6, e16255, May 5, 2017, and in "Scattering reduction by structured light illumination in line-scanning temporal focusing microscopy" by Y. Xue, K. P. Berry, J. R. Boivin, D. Wadduwage, E. Nedivi, and P. T. C. So, *Biomed. Opt. Express*, vol. 9, no. 11, p. 5654-5666, Nov. 1, 2018, the entire contents of the above publications being incorporated herein by reference in their entireties.

Figure 2A:
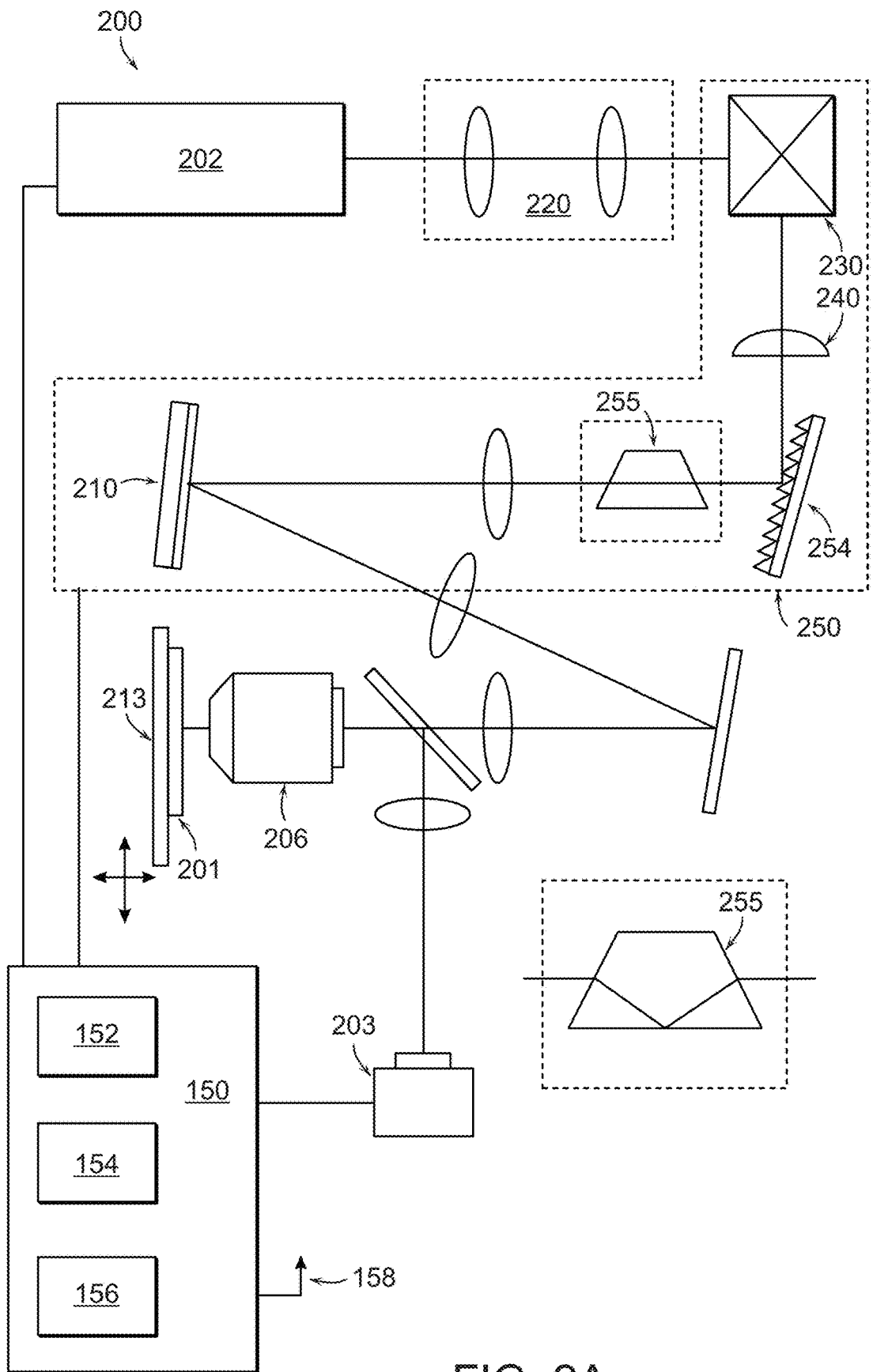
FIG. 2A illustrates a temporal focusing microscopy system in accordance with certain embodiments described herein.

A temporal focusing microscopy system 200 with reduced scattering is illustrated in FIG. 2 according to various embodiments. The system 200 can include an excitation source 202, a structured illumination system 250, an imaging device 203, and a computing device 150. The system 200 can also include beam shaping optics 220 and an objective 206. Light from the excitation source 202 passes through the beam shaping optics 220 and the structured illumination system 250. The structured illumination system 250 modulates light into illumination lines and scans the lines across a sample 201. Emitted or scattered light from the sample 201 is transmitted to a camera 203 connected to the computing system 150. For each scanning step, the imaging device 203 can record an intermediate image. The sample 201 can be moved using a translation stage 213 that moves in one- or two-dimensions to reposition the sample 201 between acquisitions of subsequent intermediate images. As a result, the system 200 can reconstruct information from the sample 201 at high speed and with high SNR by operating on the intermediate images received at the imaging device 203.

Because scattered photons arise from scatterers nearby the object of interest, signal photons and scattered photons are recorded at the same time at nearby detection elements of the imaging device 203. This effect causes an apparent "broadening" of structural features of the sample on the imaging device and reduces resolution and contrast in the final image. Systems and methods described herein can account for this broadening effect and improve image resolution.

The structured illumination system 250 can couple multiphoton illumination and structured illumination onto a sample. In various embodiments described herein, the structured illumination system 250 can modulate light into illumination lines. For example, the structured illumination system 250 can include a scan line motion actuator such as a raster scanner 230. The raster scanner 230 can scan the light in one-dimension in some embodiments. In some embodiments, the raster scanner 230 can include a scanning mirror or an array of controlled mirror elements to scan one or more lines of illumination onto the sample. The structured illumination system 250 can include a cylindrical lens 240. In some embodiments, the cylindrical lens 240 can be positioned to focus the light in the same direction as the scanning direction of the raster scanner 230 without modulation in the other dimension. In such embodiments, the light forms a single illumination line. The illumination line can be projected onto a grating 254. In some embodiments, the grating 254 can stretch the duration of the pulse, which is a key component for temporal focusing applications. As described in greater detail below, the scanning direction (i.e., the long axis of the illumination line) can be rotated using a rotation element 255. The single line of light can be split into multiple lines using phase modulation components 210.

Figure 1A:
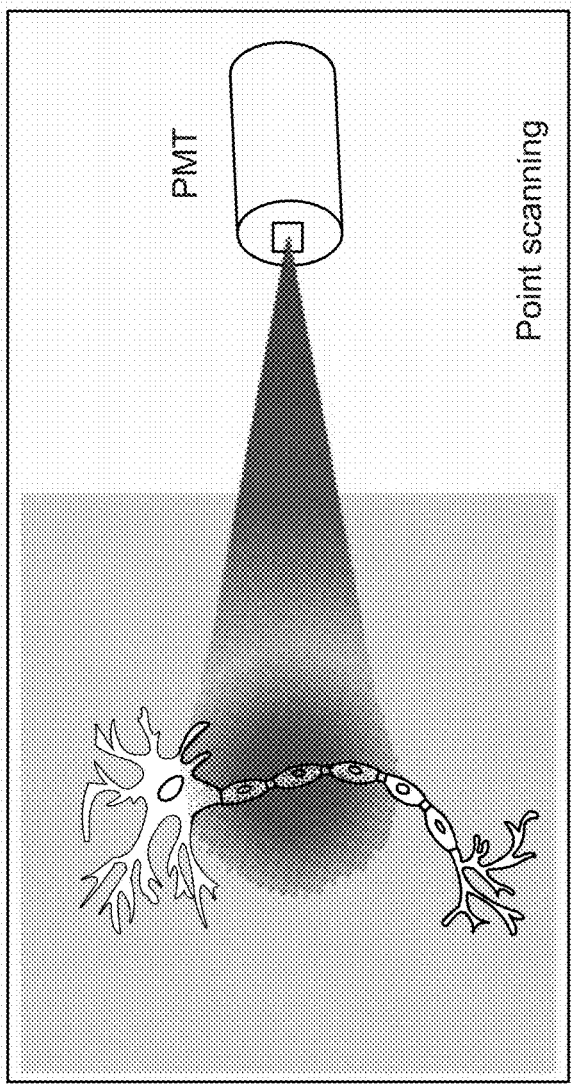
FIGS. 1A and 1B illustrate point scanning versus line scanning according to various embodiments of the present invention.
Figure 1B:
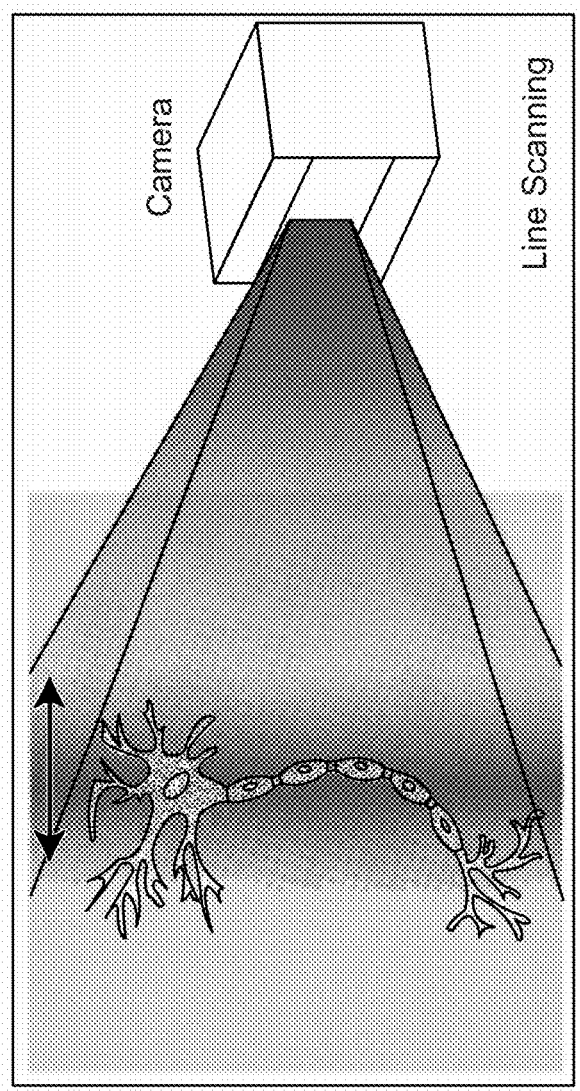

In typical approaches to point-scanning microscopy, the laser spot is rastered or scanned over the entire sample to induce scattering or emission of fluorescence photons from the sample as shown in FIG. 1A. Because the laser spot is focused at the sample to produce high intensities, the diffraction limited spot size is small and, thus, the time to raster the spot over the whole sample can be significant and can lead to slow acquisition of data. The structured illumination system 250 can employ line-scanning temporal focusing techniques as shown in FIG. 1B. By rastering lines of light across the sample, the entire sample can be covered in less time leading to faster data acquisition. In some embodiments described herein, data acquisition can be up to ten times faster than conventional point-scanning techniques. While point-scanning microscopy typically uses a photomultiplier tube (PMT) to receive light from the sample, line-scanning techniques can use an extended imaging device having a plurality of light detection elements to simultaneously capture light from the entire illuminated portion of the sample and to allow for element-wise analysis in post-processing.

Theoretically, line-scanning temporal focusing two-photon microscopy has the same theoretical spatial resolution limit as point scanning two-photon microscopy. Scattered photons can reduce signal intensity and effectively add background noise. Point-scanning techniques that use a PMT do not account for the presence of scattering photons as all photons that reach the detector are summed into a single point signal. Moreover, the presence of unwanted scattered photons can reduce the resolution and signal-to-noise ratio (SNR) of line-scanning temporal focusing techniques as compared to the point scanning approach. In various embodiments described herein, the imaging device collects scattered photons from the sample at a plurality of light detection elements and performs an element-wise reassignment of photons in a direction perpendicular to the scanning direction.

The structured illumination system 250 can include phase modulation components 210 or other diffractive optical elements (DOE) to divide a single line into multiple illumination lines. Thus, the structured illumination system couples a plurality of scanning lines onto the sample. The use of multiple illumination lines can improve imaging speed while maintaining high spatial resolution. Imaging while using multiple scanning illumination lines can provide quasi-wide-field imaging. In some embodiments, the multiple illumination lines are parallel. Multiline projection effectively parallelizes the imaging process to improve overall imaging speed compared to single line-scanning temporal focusing. Diffractive optical elements can provide high diffraction efficiency, and this efficiency can enable better equalization of the intensities of light in each illumination line. In other embodiments, the structured illumination system 250 can include a spatial light modulator (SLM) 210 instead of DOEs. The SLM 210 can provide flexible modulation of the number of scanning lines and other parameters such as line spacing. In some embodiments, line spacing is selected so as to avoid cross-talk when lines are too dense (i.e., too closely spaced). In some embodiments, line spacing is selected based upon a desired acquisition speed by increasing the number of lines (i.e., avoiding making the lines too sparse).

In some embodiments, the number of illumination lines or the line spacing can be selected based on considerations such as a thermal damage threshold of the sample or an excitation saturation or photobleaching threshold of the sample (e.g., for one- or two-photon excitation). For example, the choice of fluorophore in the sample can assist the selection of the number of lines or line spacing. For bright fluorophores, low excitation intensity can be enough to achieve a high SNR image. Because the total power is typically fixed, the structured illumination system 250 can be set to parallelize or divide the optical power among more illumination lines that are more densely spaced (i.e., line spacing is smaller).

The structured illumination system 250 can be positioned such that the SLM 210 is located in the Fourier plane of the imaging plane (i.e., the sample plane). When the SLM 210 is placed in the Fourier plane, the phase shifting of the illumination light induced by the SLM 210 can scan the multiple lines in the image plane. Thus, the SLM 210 can act as a raster scanner in some embodiments where the refresh rate of the SLM is high enough. In such a design, an independent raster scanner 230 is not required. An important advantage is thus realized because the design is made more compact. In some embodiments, the refresh rate of the SLM 210 can be up to 1 kHz. In some embodiments that use other phase modulation components such as a DOE, the DOE 210 and raster scanner 230 can be placed at conjugate Fourier planes with respect to one another. The scanning speed of a system 200 including a DOE 210 and raster scanner 230 can be in a range from 1-30 kHz.

The computing device 150 can receive modulated images of the illuminated sample 201 from the imaging device 203. In some embodiments, the computing device 150 can include one or more processors 152, a memory 154, a controller 156, and a network connection 158. The processor 152 can include one or more central computing units (CPUs) and/or one or more specialized image processing units such as graphical processing units (GPUs). In some embodiments, the processor 152 can be configured to process images received from the imaging device and generate reconstructed images of the sample. As described above, the modulated image can include both real signal information and noise information caused by background scattering. Systems and methods taught herein can reduce the impact of background-scattered photons by reassigning the background-scattered photons in the perpendicular direction back to the excitation line to reconstruct a scattering-free image. This is accomplished through a reconstruction process. In the reconstruction, a preliminary step is to estimate the full-width at half-maximum (FWHM) of the scattered light. In some embodiments, an intermediate image is selected for this measurement that has good SNR. For example, an image including some can be selected as the intermediate image. The FWHM of the emission fluorescence from the line is measured in a direction perpendicular to the line direction in the intermediate image. In various embodiments, the FWHM of the emission fluorescence can vary depending upon the depth of imaging within the sample 201. In some embodiments, the sample will be too sparse or dim at certain depths to properly measure the FWHM. In such an instance, the FWHM can be estimated using measurements from adjacent depths.

Figure 3F:
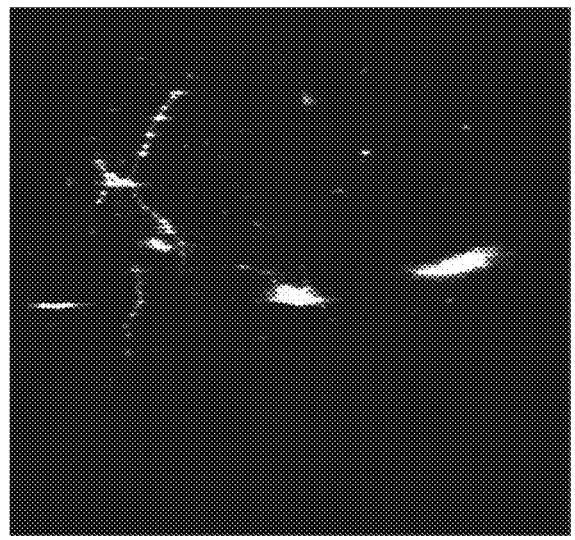
Figure 3E:
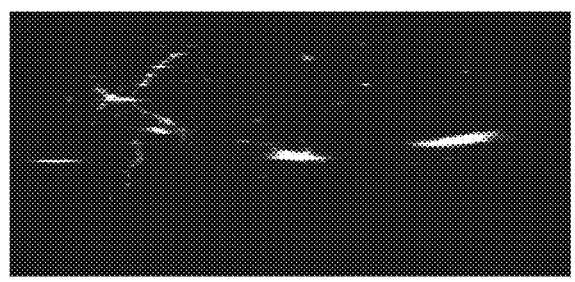
Figure 3D:
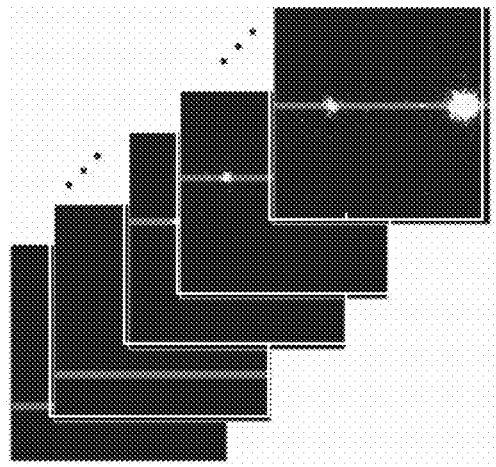

FIGS. 3A-3F illustrate stages of an exemplary reconstruction scheme for scattered photon reassignment in accordance with various embodiments described herein. In this exemplary scheme, the detection elements in the imaging device 203 are pixels in a camera. For example, the imaging device 203 can be a two-dimensional pixelated imaging device such as a charge-coupled device (CCD) or complementary metal-oxide-semiconductor (CMOS) pixelated imaging device. In the first stage, the reconstruction process identifies the center pixels of each illumination line captured in the modulated image (FIG. 3A). Then, pixels adjacent to each illumination line that lie within the FWHM of the emission fluorescence can be reassigned back to the nearest center pixel (FIG. 3B) to produce a single data column that is one-pixel wide (FIG. 3C). The reconstruction process can be repeated for each acquired modulated image as the illumination light is scanned across the sample (FIG. 3D). A preliminary reconstructed image can be formed by concatenating together each one-pixel-wide column (FIG. 3C) derived from an intermediate image in order of acquisition in the direction of scanning (FIG. 3E). In some embodiments, the scan step length can be less than or greater than the pixel size. For example, the scan step length for the acquisition in FIGS. 3A-3E was equivalent to two pixels. In some embodiments, the final image (FIG. 3F) can be reconstructed by linear interpolation from the column-by-column stitched image (FIG. 3E). This process can be repeated along a plurality of angular scanning directions. After obtaining a number of reconstructed images corresponding to different angular scanning directions, the reconstructed images along the different orientations can be overlapped (with proper weighting) to generate an isotropic reconstructed image.

Figure 4B:
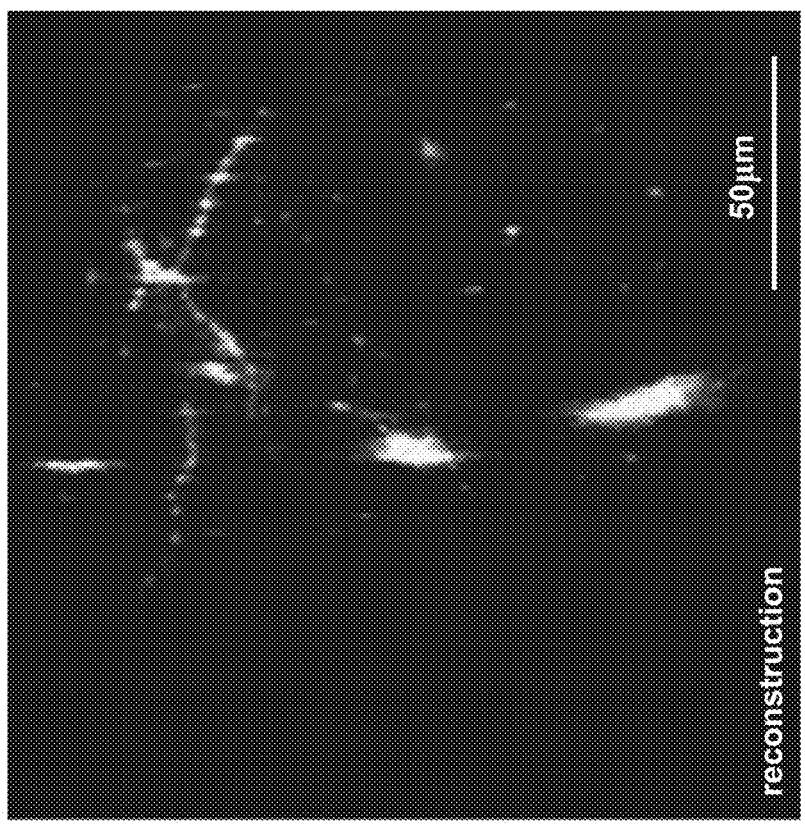
FIGS. 4A and 4B illustrate unreconstructed and reconstructed in vivo images using a CMOS imaging camera.
Figure 4A:
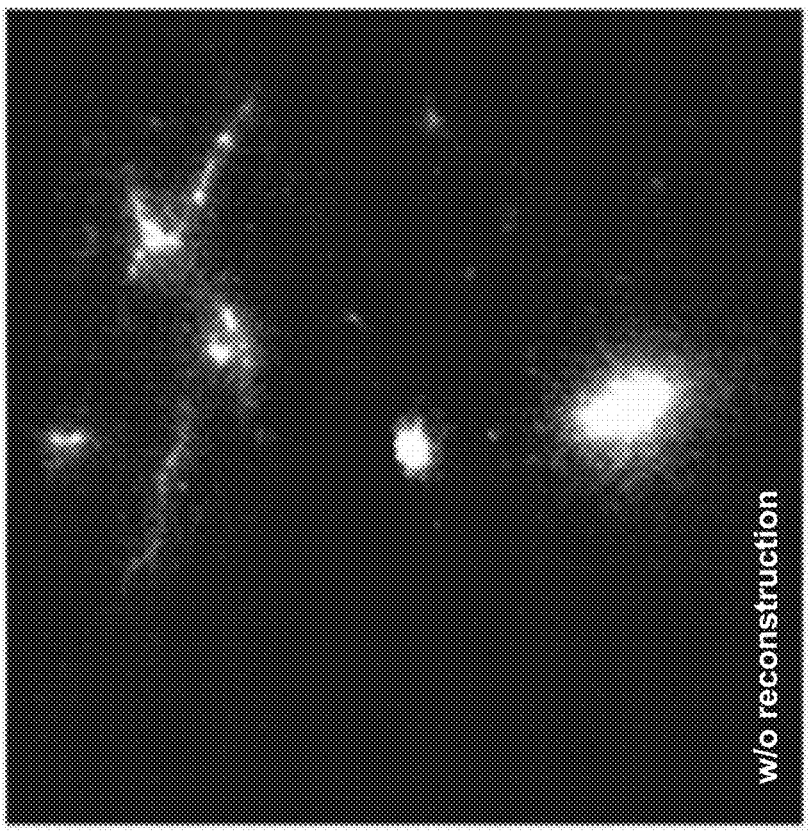
Figure 4C:
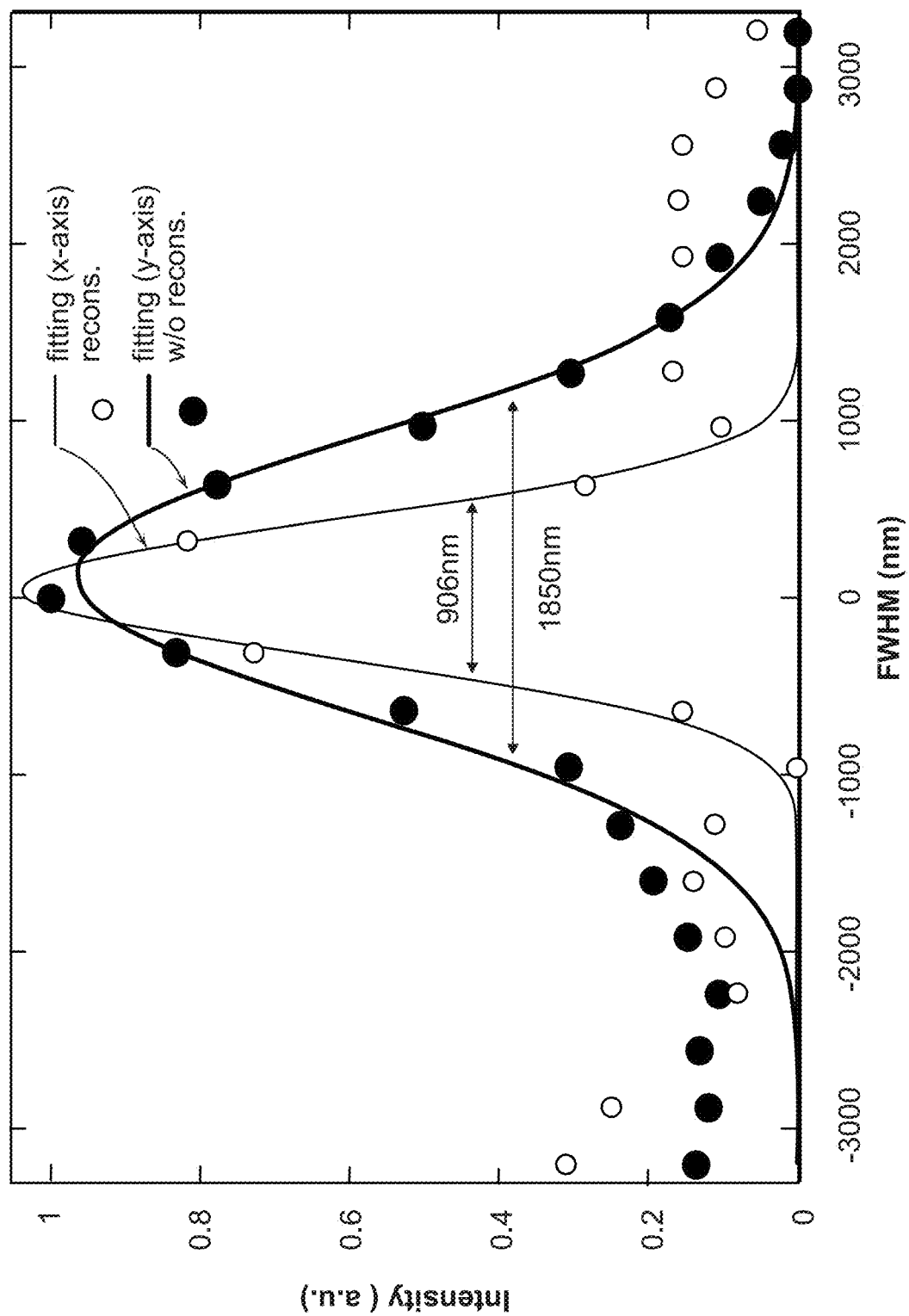
FIG. 4C graphically illustrates the improved full width half maximum obtained by reconstruction.
Figure 10A:
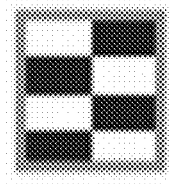
FIGS. 10A-10C illustrate the transformation of a structured illumination pattern of an arbitrary pixel group in accordance with various embodiments described herein.
Figure 10B:

FIGS. 4A and 4B illustrate unreconstructed and reconstructed in vivo images, respectively, of neurons in a neuronal cortex subjected to a cell-fill protocol with yellow fluorescent protein (YFP) and imaged using the techniques described herein. The imaging device was an ultrafast sCMOS camera (HiCAM, Lambert Instruments, Groningen, Netherlands). Each intermediate image was exposed for 4 ms. To generate a single plane image, 250 intermediate images were collected. FIG. 4A illustrates the sum of these 250 intermediate images with background subtraction but without the reconstruction techniques described herein. As shown, the image is washed out due to scattering caused by brain tissue. FIG. 4B illustrates a reconstructed plane image. To create this image, the line scanning direction was along the x-axis and, thus, the reconstruction direction is also along the x-axis. Note that the PSF for this image is asymmetric with respect to the x- and y-axes because the reconstruction is one-dimensional. For the reconstructed image in FIG. 4B, 10 pixels (~3.2 um) was used as the scattered FWHM in the reconstruction (e.g., see FIG. 3B). As described above, photons from the adjacent 10 pixels are summed back to the center pixel of the scanning line. For each intermediate image produced as the illumination lines are scanned across the sample, we can reconstruct the pixels where the scanning line illuminates. In some embodiments, the scan step size can be equal to the measured or estimated PSF. For example, the scan step size for the images shown in FIGS. 4A and 4B was two pixels or about 640 nm, which is the same as the PSF. FIG. 4C illustrates the lateral full-width half-maximum of features enhanced by reconstruction (x-axis, e.g., scanning axis) and features not enhanced by reconstruction (y-axis). The FWHM is significantly improved by the reconstruction technique as the effect of scattering is curtailed. For example, the cross-sectional dimension of a dendrite is more than two-fold smaller in the x-axis than in the y-axis. The reconstruction techniques described herein result in the ability to resolve finer structures in the image.

The reconstruction technique can operate to ameliorate scattered photons in a direction perpendicular to the illumination line and parallel to the scanning direction. In some embodiments, the structured illumination system 250 can rotate the illumination lines through various angles during acquisition of intermediate images. By rotating the illumination lines, a single field of view (e.g., a slice of the sample) can be reconstructed in multiple directions to provide a final image having an isotropic lateral PSF. For example, pixels from reconstructed images obtained using illumination lines that scan along different directions can be stitched together to achieve the final reconstructed image.

Figure 2B:
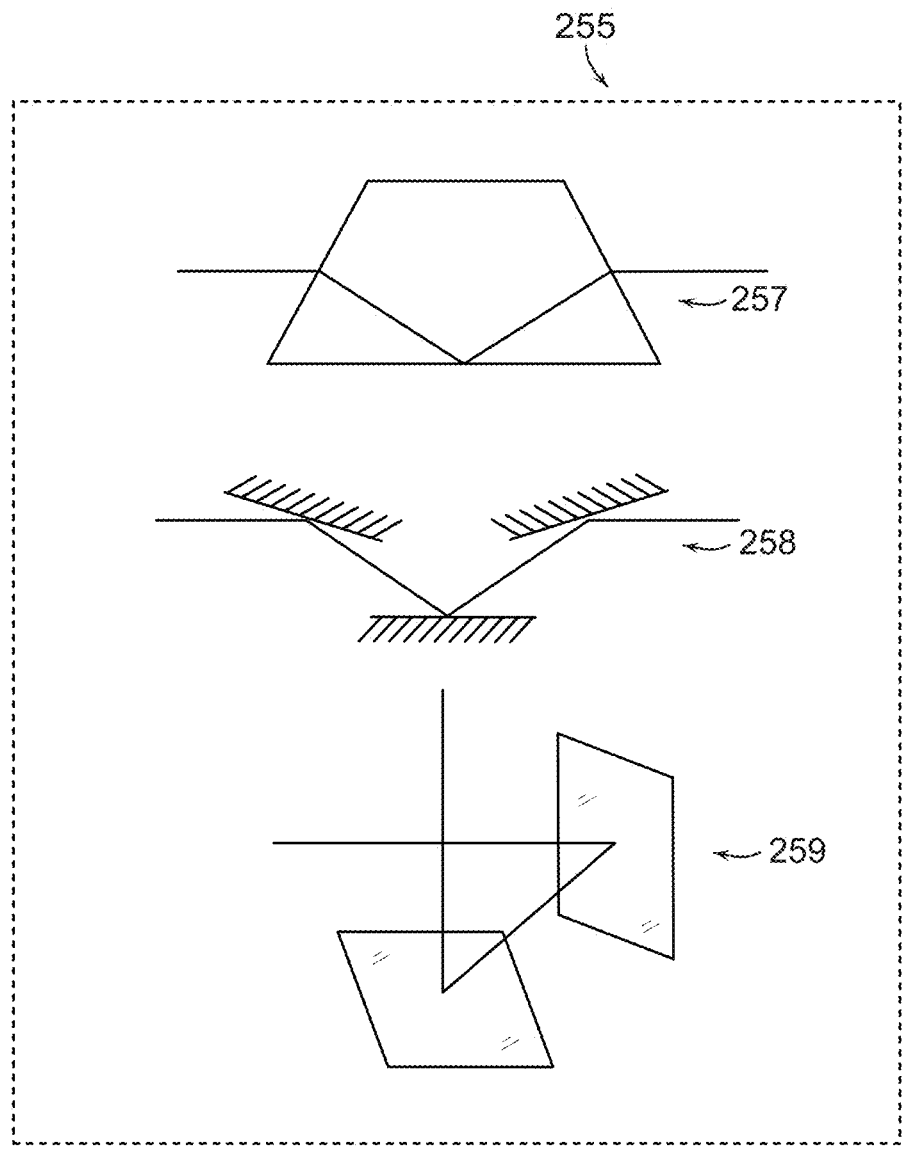
FIG. 2B illustrates examples of rotation elements for use with some embodiments of temporal focusing microscopy systems as described herein.

In some embodiments, the structured illumination system 250 can include a rotation element 255. Several varieties of rotation elements 255 are illustrated in FIG. 2B. In various embodiments, the rotation element 255 can be a Dove prism 257 or a pair of mirrors. The Dove prism 257 can invert the signal and can rotate the output beam by an angle of $2\alpha$ for each rotation of the prism through an angle of $\alpha$. In some embodiments, the Dove prism 257 can add phase dispersion to the femtosecond laser pulse that can decrease two-photon excitation efficiency at the sample. Use of the pair of mirrors as the rotation element 255 can reduce the effect of phase dispersion at the cost of a more complicated optical path design. Use of three mirrors 258 as the rotation element 255 can rotate the output beam by an angle of $-2\alpha$ for each rotation of the prism through an angle of $\alpha$. In some embodiments, the use of two mirrors 259 placed orthogonally as the rotation element 255 can rotate the output beam by $\pi/2$ for orthogonal scanning, as a subset of angular scanning.

By rotating the illumination light, the scanned illumination lines are rotated through different angles with respect to the imaging plane. In some embodiments, the rotation element 255 can rotate the illumination lines at multiple angles (i.e. $[0, \pi/3, 2\pi/3]$ or $[0, \pi/2]$) to acquire multiple sets of intermediate images at different angles. Rotating the scanned illumination lines can help achieve an isotropic point spread function. The resulting intermediate images can enable reconstruction of a final image without the effects of scattering. In such an embodiment, the reconstruction process wherein pixels are reassigned can be repeated for each series of intermediate images obtained using scanned lines that are rotated through angles. In some embodiments, rotation of the illumination lines can be combined with multiple line projection to provide for scattering-free images at high resolution, high throughput, and high SNR in deep tissue.

Rotating the temporally focused multiple scanning lines is equivalent to rotating the conjugate back focal plane of the microscope. In some embodiments, the rotation element 255 is positioned on the common path of the illumination light and the returning emitted or scattered light from the sample. In these embodiments, the emitted or scattered light from the sample can be descanned and detected by the fixed pixels of the imaging device 203. An advantage of the descanned design is the large variety of imaging devices or detectors that may be used. In the descanned design, the position of the image (whether a single or multiple lines) does not change even as the illumination lines scan and rotate across the whole FOV. As a result, the imaging device 203 can be a camera or one-dimensional detector array such as a linear array of multianode PMTs. In some embodiments, the imaging device 203 can include a two-dimensional array of multianode PMTs. Multianode PMTs can have greater photon sensitivity and faster imaging speed than a camera in some embodiments. Thus, use of the descanned design can improve imaging speed and lead to higher SNR at the price of a more complicated system design. In some embodiments, the descanned design can utilize a second Dove prism coated at the fluorescence wavelength in the detection path that is synchronized with the Dove prism 255 located in the illumination path. In an alternative embodiment, a pair of broadband coated mirrors can be used instead of the Dove prism. In some embodiments, the imaging device 203 can acquire images and transfer the images to the computing device 150 at a sufficient speed to acquire an image for each excitation pattern.

In some embodiments, the rotation element 255 can be positioned only on the path of the illumination light as shown in FIG. 2. In these embodiments, the emitted or scattered light from the sample rotates on the imaging device 203. In some embodiments, the use of a single rotation element 255 can provide a simpler and more robust design.

Figure 23D:
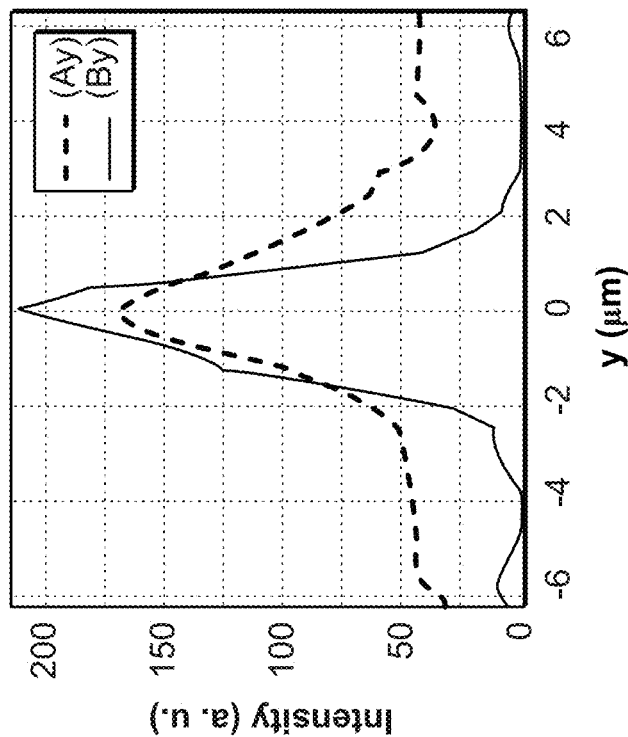
FIGS. 23C and 23D graphically illustrate the improved signal-to-noise ratio obtained by reconstruction.
Figure 23C:
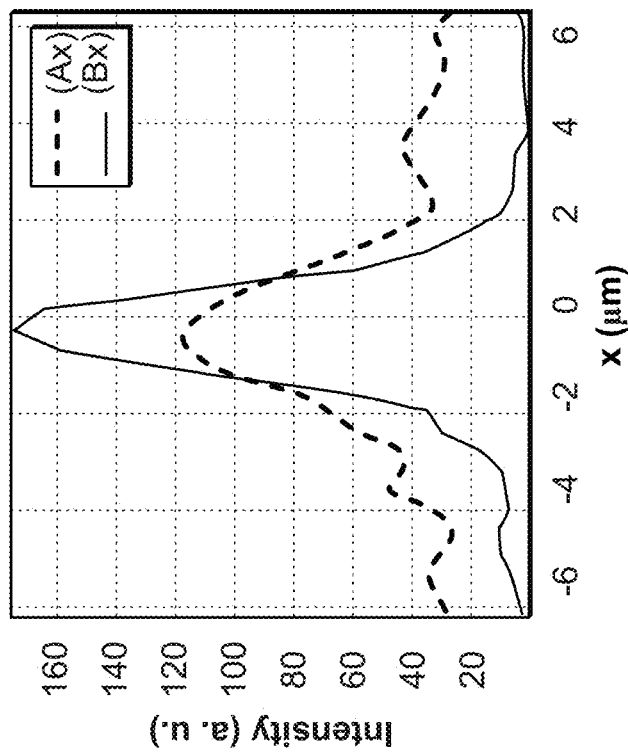

FIGS. 23A and 23B illustrate unreconstructed and reconstructed in vivo images, respectively, of neurons in a neuronal cortex subjected to a cell-fill protocol with yellow fluorescent protein (YFP) and imaged using the system 200 including a rotating element 225. The imaging device 203 was an ultrafast EMCCD camera (HNu512, Nuvu Cameras, Montreal, Canada). Each intermediate image was exposed for 16 ms. Four lines were scanned in parallel. To generate a single plane image, 128 intermediate images were collected. FIG. 23A illustrates the sum of these 128 intermediate images with background subtraction but without the reconstruction techniques described herein. As shown, the image is washed out due to scattering caused by brain tissue. FIG. 23B illustrates a reconstructed plane image. To create this image, the line scanning direction was along the x-axis and, thus, the reconstruction direction is also along the x-axis. The same process was applied to y-axis as well. For the reconstructed image in FIG. 23B, various pixels (7-50 pixels, corresponding to 2.8-20 um) related to pixel intensity were used as the scattered FWHM in the reconstruction (e.g., see FIG. 3B). As described above, photons from the adjacent few pixels are summed back to the center pixel of the scanning line. For each intermediate image produced as the illumination lines are scanned across the sample, we can reconstruct the pixels where the scanning line illuminates. In some embodiments, the scan step size can be equal to the measured or estimated PSF. For example, the scan step size for the images shown in FIGS. 23A and 23B was one pixel or about 400 nm, which is the same as the PSF. FIGS. 23C and 23D illustrate the lateral full-width half-maximum of features enhanced by reconstruction (corresponding to FIG. 23B) and features not enhanced by reconstruction (corresponding to FIG. 23A) in both the x-axis and the y-axis. The SNR is significantly improved by the reconstruction technique as the effect of scattering is curtailed. In some embodiments, the imaging device could be an ultrafast sCMOS camera (e.g., HiCAM, Lambert Instruments, Groningen, Netherlands) that enables a very short exposure time of 1 ms at the cost of higher readout noise, which can further improve the imaging speed. The reconstruction techniques described herein result in the ability to resolve finer structures in the image.

While line-scanning approaches can increase image acquisition speed (particularly for multiple lines) over typical point-scanning methods, the use of wide-field illumination (i.e., illumination of the entire slice of the sample at one time) can speed up acquisition still further. However, images obtained using wide-field methods can be noisy because of multiple scattering of the emission photons within the sample. In particular, the excitation light can be at a relatively long wavelength that can propagate through a scattering medium such as biological tissue without much disturbance to the light. However, the emission light wavelength is typically shorter as compared to the excitation light wavelength in temporal focusing multi-photon processes. Thus, the emission light that the microscope is trying to detect is strongly scattered as it propagates out of the medium. Systems and methods described herein can overcome image degradation due to emission light scattering in wide-field microscopes.

In accordance with some embodiments of this disclosure, a modified temporal focusing microscope (TFM) can project arbitrary excitation patterns onto the focal plane using a digital mirror device (DMD). Emission light from the modulated excitation is then detected by a camera. By using near-infrared (NIR) wavelengths for imaging, the excitation patterns maintain their fidelity despite traveling through scattering medium. However, the emission photons are scattered by tissues and the strength of scattering is strongly depth dependent. In particular, this assumption holds for most biological tissue. In practice, TFM images are minimally affected by scattering at or near the surface; as the imaging depth increases, scattering gradually degrades high-frequency information in the images. However, low frequencies in the images are retained for most depths even with wide-field detection. Single pixel detection approaches discard this low frequency information, and hence require a large number of excitation patterns. Systems and methods herein can then combine the information about the excitation patterns (through a calibration process) with the acquired images to computationally reconstructed a de-scattered image. In some embodiments, multiple patterned excitations (and images) are needed to de-scatter a single field of view (FOV). In some embodiments, the number of patterns and images depends on the loss of high-frequency information due to scattering, and hence on the imaging depth.

Figure 5A:
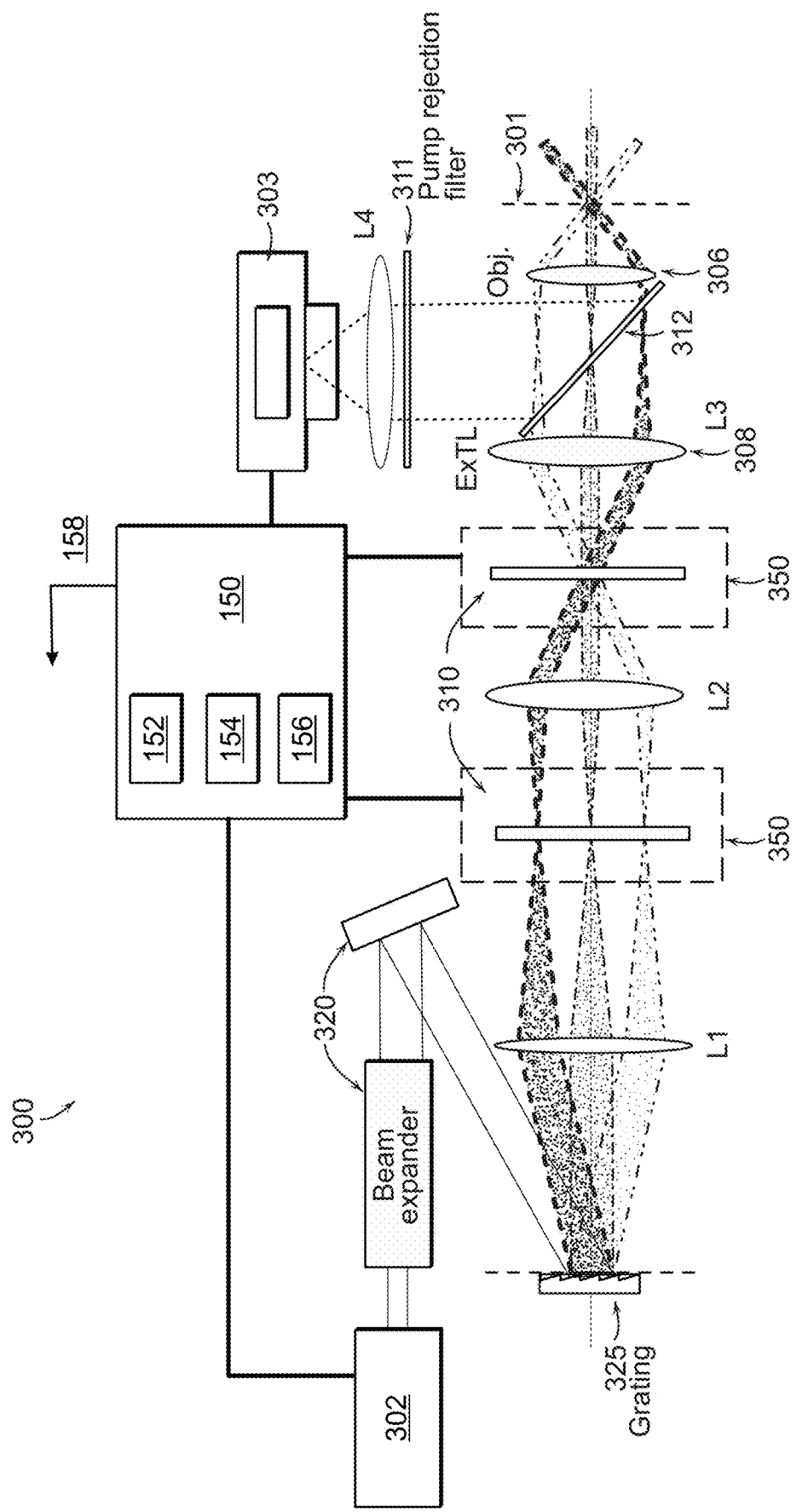
FIGS. 5A and 5B illustrate widefield temporal focusing microscopy systems in accordance with various embodiments described herein.
Figure 5B:
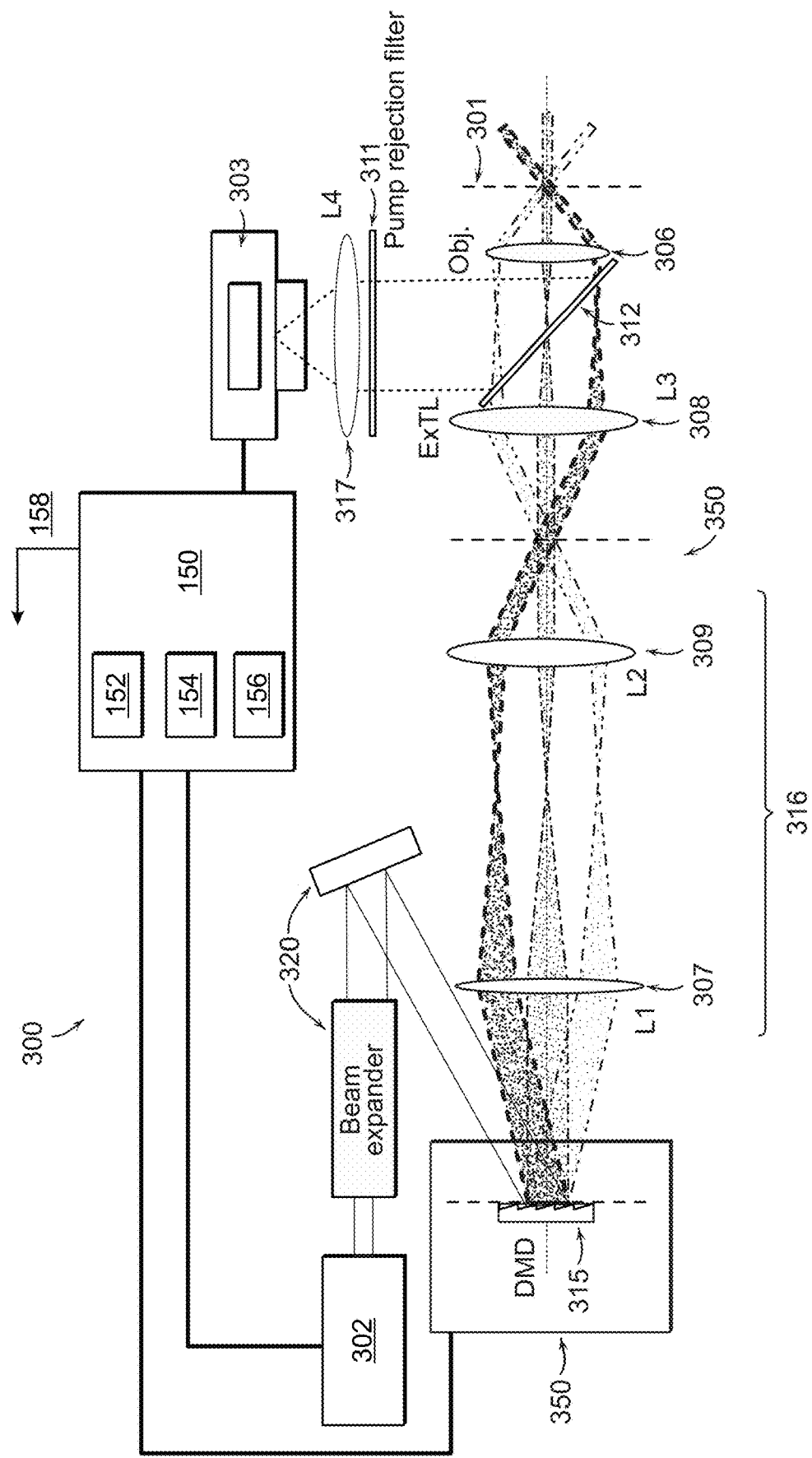

FIGS. 5A and 5B illustrate alternative embodiments of temporal focusing microscopy systems 300 with reducing scattering using structured illumination. The systems 300 can include an excitation source 302, one or more beam-shaping or beam-steering optics 320, a structured illumination system 350, an imaging device 303, a computing device 150, a dichroic mirror 312, and an objective 306. The wide-field temporal microscopy systems 300 can acquire depth-selective images of a sample with reduced emission scattering by encoding an arbitrary pattern into the illumination light before illuminating the sample and decoding the resulting image of the sample received at the imaging device.

The excitation source 302 can include a pulsed laser in some embodiments. For example, the pulsed laser can provide femtosecond pulses (e.g., 100-fs temporal pulse width) at near-IR wavelengths (e.g., 800 nm). In various embodiments, the repetition rate of the pulsed laser can be in a range from 1 kHz to 10 MHz. The pulsed laser can emit illumination that is coupled to the sample and enables two-photon imaging of the sample. In some embodiments, the objective 306 can have a magnification of between 5× and 50×. In an exemplary embodiment, the objective 306 can have a magnification of 20×. The objective can have a numerical aperture of 1.0 in some embodiments.

The one or more beam-shaping or beam-steering optics 320 can expand the beam size in various embodiments. For example, the beam-shaping optics 320 can include a beam expander. The beam-steering optics 320 can direct the excitation light output to a diffractive optical element (DOE) 325 in some embodiments. For example, the diffractive optical element 325 can include a grating. The DOE 325 can diffract the beam with a specific diffraction angle for each color of excitation light so that the pulse width is broad at all points other than at the DOE 325 plane and the conjugate image plane or planes of the DOE 325. In some embodiments, the system 300 can include a 4-f lens system following the DOE 325. In some embodiments, the 4-f lens system can control the size of the field of view (FOV) at the sample plane.

In some embodiments, the 4-f lens system can include two lenses wherein a structured illumination system 350 is placed at the Fourier plane of the lens system as shown in one embodiment in FIG. 5A. The structured illumination system 250 can couple multiphoton illumination and structured illumination onto a sample. In some embodiments, the structured illumination system 350 can include a spatial light modulator (SLM) 310. In an alternative embodiment, the structured illumination system 350 can be placed at a focal plane before the 4-f lens system. In some embodiments, the structured illumination system 350 can receive pattern information from a computing device 150 communicatively coupled with the structured illumination system 350. In some embodiments, the structured illumination system 350 can include a data processor with pattern information. In either embodiment, the pattern information can be pre-stored or can be adaptively generated based upon updated imaging conditions. The structured illumination system 350 modulates the distribution of excitation light according to the selected pattern as the light passes through the system. As described below, image information for the object can be reconstructed by post-processing from stacks of modulated raw images using the known excitation/illumination patterns as a priori information.

In some embodiments as shown in FIG. 5B, the structured illumination system 350 can include an amplitude based pattern generator placed at the image plane. For example, the structured illumination system can include a digital micromirror device (DMD) 315. In some embodiments, the amplitude-based pattern generator can act as a diffractive element and pattern generator simultaneously. For example, because the DMD 315 can comprise grid patterns of millions of micron sized mirrors, it can behave like a two-dimensional diffractive element. Each mirror in the DMD 315 can be tilted to two positions corresponding to "on" or "off" for each corresponding pixel. In some embodiments, the DMD 315 can include the V-7000 (Vialux), LightCrafter (Texas Instruments), or LightCrafter 9000 (Texas Instruments), all of which work well at visible wavelengths. In preferred embodiments, the DMD 315 can have a pitch in the low micrometer range as such devices can typically handle greater amounts of optical power. For example, the pitch of elements in the DMD 315 can be in a range from between 5 μm and 15 μm. In some embodiments, the DMD 315 can have a refresh rate of between 1 and 30 kHz.

In accordance with some embodiments, arbitrary pattern images can be generated using software implemented by the computing device 150. For example, patterns can be generated in Matlab by using the 'rand' function to produce 0 or 1 for each pixel. In some embodiments, patterns of 1024-by-1024 pixels that are resized by a factor of 8 can be used. This implementation defines a unit block of 8-by-8 pixels at the DMD 315, which corresponds to 60.8 μm for the length of one side. The corresponding size of the unit block at the sample plane is 0.83 μm, which can be close to the effective diffraction limit of the system in some implementations $[\lambda/(2NA2)]$. In this embodiment, the total number of patterns for each imaging session will be 256 to provide a complete basis set. In other embodiments, patterns of 1600-by-1600 pixels at the DMD 315 can be used to enlarge the field-of-view of the system 300 while employing a magnifying lens setup as described below in front of the imaging device 303. The exposure time of the imaging device 303 can be adjusted in some embodiments in the range of 100-500 ms per pattern depending upon the signal intensity of a given specimen. The EM gain of the camera can be set to be 3-100 depending on the signal intensity of a given specimen in some embodiments. In some embodiments, the imaging device 303 can acquire images and transfer the images to the computing device 150 at a sufficient speed to acquire an image for each excitation pattern.

The system 300 can include a second 4-f lens system in some embodiments. The second 4-f lens system can include a tube lens 308 and a high numerical aperture (NA) objective lens 306 to form patterned temporally-focused illumination light at a sample plane 301.

For each projected pattern, an image can be obtained using the imaging device 303. The imaging device 303 can include a plurality of detection elements in various embodiments. For example, the imaging device 303 can include a camera having an array of pixels preferably with 5 million or more pixel elements that can be individually addressed. The imaging device 303 can be a two-dimensional pixelated imaging device such as a charge-coupled device (CCD) or complementary metal-oxide-semiconductor (CMOS) pixelated imaging device. In some embodiments, the imaging device 303 can include a one-dimensional or two-dimensional array of multianode PMTs. The system 300 can include a filter 311 to reject light at the excitation wavelength in some embodiments. The images can be sent to the computing device 150 for further processing in some embodiments. For example, an image for each pattern can be saved in memory 154 or a database in the computing device 150 for post-processing.

The computing device 150 can be configured to control pattern projection of the structured illumination system 350, image acquisition using the imaging device 303, image storage, and/or image processing. For example, the computing device 150 can be configured to execute instructions to select a structured illumination pattern. For example, the structured illumination pattern can be selected based on a row of a Hadamard matrix in some embodiments. The computing device 150 can execute instructions to configure the structured illumination system 350 to modulate light from the light source 303 using the selected structured illumination pattern. The modulated light is used to illuminate the sample. For example, the computing device 150 can send the structured illumination pattern to the structured illumination system 350 for local configuration by the structured illumination system 350 or the computing device 150 can directly control the structured illumination system 350 to cause the structured illumination pattern to modulate the light.

The computing device 150 can execute instructions to receive image data corresponding to light emitted or scattered from the sample and received at the plurality of light detection elements of the imaging device 303. The computing device 150 can execute instructions to generate a reconstructed image of the sample by performing a processing operation on the received image data.

In some embodiments, the computing device 150 can execute instructions to receive intermediate image data corresponding to light emitted or scattered from the sample and received at the plurality of detection elements of the imaging device to form an intermediate image. The computing device 150 can execute instructions to collect additional intermediate images wherein each additional intermediate image corresponds to a different structured illumination pattern. The computing device 150 can reconstruct at least a portion of a depth-selective image of the sample by performing an element-wise reassignment or demodulation operation on the intermediate images using the known structure illumination patterns as a priori information as described in greater detail below.

In some embodiments, the excitation source 302 can include a regenerative amplifier (for example, the Legend Elite, Coherent, Santa Clara, Calif., USA) to produce an ultrafast pulsed laser beam with 800 nm center wavelength, 120 fs pulse width, 10 kHz repetition rate, and ~8 mm beam diameter ($1/e^2$). Beam shaping optics 320 such as a beam expander can magnify the beam to ~32 mm and direct the beam to the DMD 315 (DLP LightCrafter 9000 EVM, Texas Instruments, Tex., USA). DMD 315 can be used as a diffractive element and pattern generator simultaneously in some embodiments. In some embodiments, the beam can be diffracted from the DMD 315 with an effective grating period of ~190 lines/mm with an incident angle of 26.4°. Arbitrary patterns can be uploaded onto the DMD 315 using a control program such as the DLP LCR 9000 GUI provided by Texas Instruments. After the DMD 315, the beam can pass through a 4f-lens system 316 including two planoconvex lenses 307, 309. The first lens 307 can have a focal length f=250 mm (LA1461, Thorlabs, Newton, N.J., USA) and the second lens 309 can have a focal length f=125 mm (AC254-125-B-ML, Thorlabs, Newton, N.J., USA). The 4f-lens system 316 projects and magnifies the image of the DMD 315. The images formed by the 4f-lens system (e.g., $L_1$ and $L_2$) are relayed onto the sample plane 301 through the tube lens 308 (f=300 mm; AC508-300-B-ML, Thorlabs) and the objective lens 306 (water immersion 20×/1.0, Zeiss, Jena, Germany). In some embodiments, the system magnification is about 73× based on the focal lengths of tube lenses and the effective focal length of the objective lens. The geometric dispersion of the system can ensure that the pulse width is broad enough to minimize multiphoton excitation except for at the sample plane 301. In some embodiments, the location of objective 306 can be controlled using a positioner or translation stage. For example, an objective piezo positioner (MIPOS-500, Piezosystem Jena, Jena, Germany) can be used.

The two-photon excitation fluorescence from the sample plane 301 is collected by the objective lens 306 in an epi detection geometry and reflected by a dichroic filter 312 (Di03-R635-t3, Semrock, Rochester, N.Y., USA) towards the imaging device 303. A tube lens 317 (f=200 mm; PAC064, Newport, Irvine, Calif., USA) images the fluorescence signals onto the imaging device 303. In some embodiments, the imaging device 303 can include an EMCCD camera (iXon+, Andor, Belfast, Northern Ireland). For multicolor detection, three combinations of filter sets can be used; a blue channel centered at 460 nm (Semrock FF01-460/60-25 and Chroma E530SP-SPC), a green channel centered at 535 nm (Chroma ET535/70M and Chroma ET680SP-2P8), and a red channel centered at 605 nm (Chroma ET605/70M and Chroma E700SP-2P). In some embodiments, an achromatic doublet lens pair (1:2, MAP1050100-A, Thorlabs) can be used to expand the image size onto the camera. This arrangement can be particularly useful when the DMD 315 having 1024×1024 pixels is used for pattern generation. For patterns of even larger pixel size (1600×1600), a 1:1 achromatic doublet lens pair (MAP107575-A, Thorlabs) can be used to ensure the image fits onto the imaging device 303.

Data from the imaging device 303 can be transferred to the computing device 150 using a control program provided by the imaging device 303 manufacturer (e.g., Andor Solis, Andor, Belfast, Northern Ireland) or by control software implemented by the processor 152 of the computing device (e.g., control software implemented using LabVIEW 2015, National Instruments, Austin, Tex., USA).

The approach in systems 300 is to use a combination of wide-field temporal focusing (WFTF) and arbitrary pattern projection generated using the structured illumination system 350 (e.g., by a spatial light modulator (SLM) or a digital micromirror device (DMD)). Patterns can modulate spatial information at a focal plane deep in sample. Thus, spatial features of the object can be demodulated upon wide-field detection despite the presence of emission light scattering. Since scattering is more severe at deeper points in the sample, more patterns are required to obtain additional spatial information at deeper points. However, each pattern must be exposed to the sample for enough time to form an image, and a large number of patterns may lead to longer imaging times that can induce photodamage in the sample. To reduce the total imaging time, a pattern can be formed using multiple, identical sub-patterns which are termed herein as a pixel group. To further reduce the imaging time, systems and methods herein can exploit the sparsity of certain biological targets such as neurons by making compressed measurements as described in greater detail below. Post-processing of these images using demodulation can recover scattering-free images from wide-field excitation. An example encoded microscopy concept is described in "Encoded multisite two-photon microscopy" by M. Ducros et al., *Proceedings of the National Academy of Science*, vol. 110, no. 32, 13138-13143, August 2013, the contents of this publication being incorporated herein by reference in its entirety.

Figure 6:
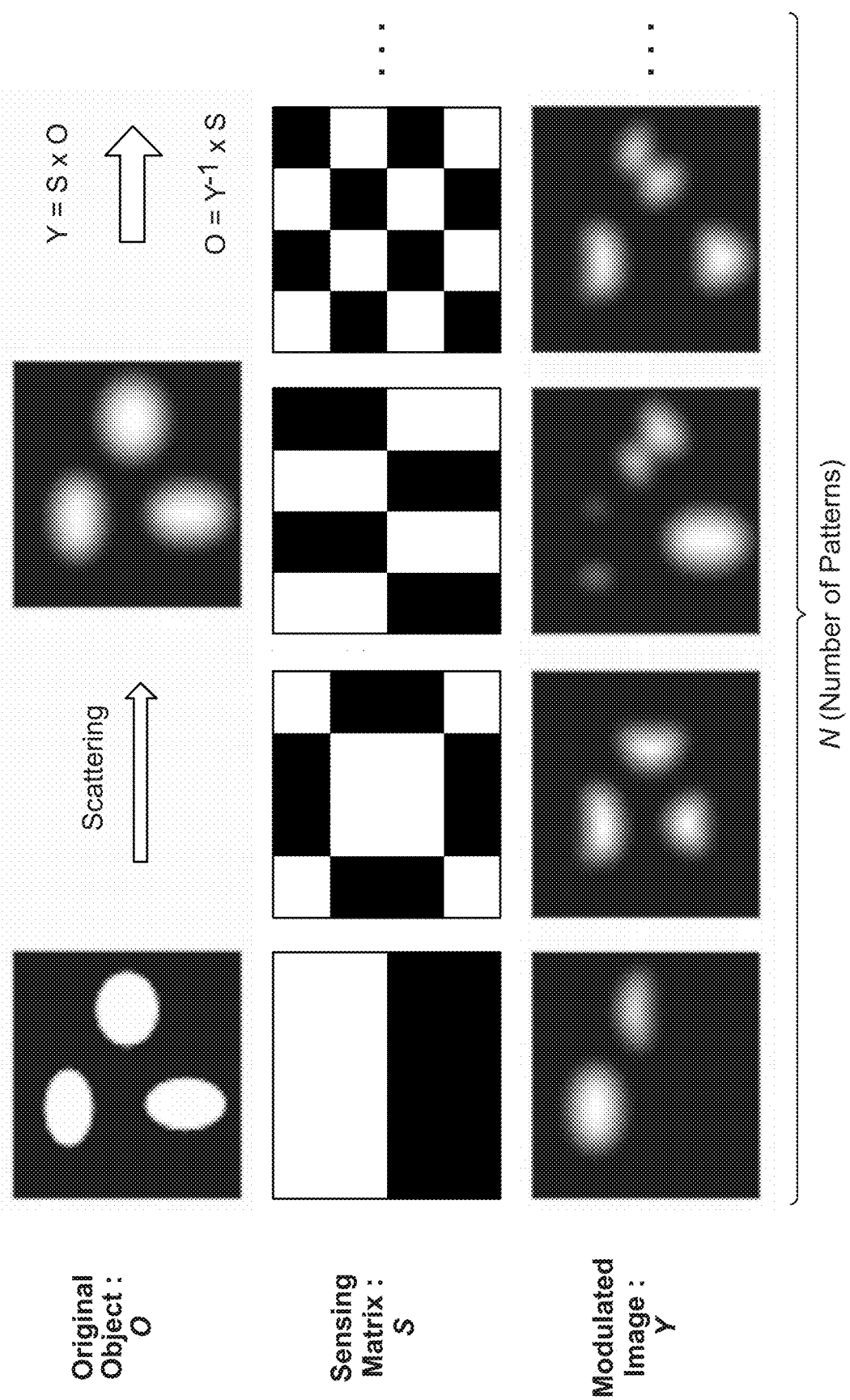
FIG. 6 illustrates a scheme for arbitrary pattern projection in wide-field temporal focusing microscopy to overcome image degradation caused by emission scattering in accordance with various embodiments described herein.

FIG. 6 shows a schematic diagram illustrating the principles behind systems and methods described herein. With plane wide-field illumination, emission scattering degrades image quality. The scattering strength increases exponentially with depth in the sample and significantly limits imaging depth compared to conventional point-scanning multiphoton microscopy techniques. Eventually, a complete loss of contrast occurs beyond a certain depth because strong scattering makes the features in the image indistinguishable from noise. The projection of random patterns composed of periodic on/off modulations in two-dimension (e.g., a Hadamard pattern) can partially excite the sources of emission in the sample. By varying the spatial frequency in the modulated on/off patterns, systems and methods described herein can identify the location of the emission source in the sample plane by collecting the scattered photons on the sensor of the imaging device. A similar approach has been shown using a single pixel camera as described in U.S. Patent Publication 20110025870, the entire contents of which is incorporated herein by reference. The setup described in that publication is limited to a one-photon excitation regime and provides no depth resolution of the sample. Conversely, systems and methods described herein can provide deep imaging with depth sectioning capabilities.

A mathematical model is provided of the process to generate modulated images for a FOV in the focal plane of the microscope. The following table provides a list of important symbols used in this section for convenient reference:

| Symbol | Type | Size | |
|---|---|---|---|
| X | Matrix | [N × N] | Imaged field of view (FOV) |
| N | Scalar | — | Imaged field of view size in pixels |
| n | Scalar | — | Pixel group size in pixels |
| m | Scalar | — | Matrix parameter of the Hadamard matrix of size $2^m \times 2^m$ |
| $x_{(k,l)}$ | Matrix | [n × n] | An arbitrary pixel group from the partitioned FOV; starting pixel (k, l) |
| $h_m$ | Matrix | $[2^m \times 2^m] = [n^2 \times n^2]$ | Hadamard matrix used to generate encoding patterns. |
| $h_{m,r}$ | Vector | $[1 \times n^2]$ | $r^{th}$ row of $h_m$ |
| $\mathbf{h}_{m,r}$ | Matrix | [n × n] | Reshaped version of $h_{m,r}$ used for projections |
| $H_{m,r}$ | Matrix | [N × N] | The full illumination pattern generated by replicating $\mathbf{h}_{m,r}$ on to all the pixel groups. |
| $Y_r$ | Matrix | [N × N] | Modulated FOV; from $r^{th}$ modulation pattern |
| sPSF | Matrix | [N × N] | Scattering point spread function |
| $Y_{r,s}$ | Matrix | [N × N] | Scattered $Y_r$ |
| mPSF | Matrix | [N × N] | Microscope's point spread function |
| $\hat{Y}_r$ | Matrix | [N × N] | Final detected image; from $r^{th}$ modulation pattern |
| $\hat{X}$ | Matrix | [N × N] | The estimation of X |
| $\hat{y}_{k,l,r}$ | Scalar | — | Macro pixel intensity of arbitrary pixel group of $\hat{Y}_r$; pixel group's starting pixel (k, l) |
| $\hat{X}_{k,l}$ | Matrix | [n × n] | The estimation of the pixel group $x_{k,l}$ |
| $\hat{x}_{k,l}$ | Vector | $[1 \times n^2]$ | Vectored version of $\hat{X}_{k,l}$ |
| $\hat{y}_{k,l}$ | Vector | $[1 \times n^2]$ | Vector containing $\hat{y}_{k,l,r}$ s for all r |
| $\tilde{X}_{(p,q)}$ | Matrix | [n × n] | An arbitrary virtual pixel group from $\hat{X}$; starting pixel (p, q) |
| $\bar{h}_{p,q,m,r}$ | Matrix | [n × n] | A circular shifted version of $\mathbf{h}_{m,r}$; circular shift is based on (p, q) |
| $\bar{h}_{p,q,m}$ | Matrix | $[2^m \times 2^m] = [:$ | A column-rearranged version of $h_m$; the column arrangement is based on (p, q) |

In some embodiments, systems and methods described herein encode spatial information using multiple modulation patterns replicated in the partitioned field of view. Let the imaged focal field of view be represented as X(i,j). For simplicity, assume X contains N×N pixels. Here, i, j ∈ {1, 2, . . . , N}, are, respectively, the row and the column pixel indices. Let the FOV be partitioned into (N/n)×(N/n) pixel groups where each pixel group contains n×n pixels (see FIG. 7A). The pixel group size, n, is determined by the severity or magnitude of scattering and can be treated as a known prior. Additionally, in order to satisfy the conditions of the basis used to generate modulation patterns (such as the Hadamard basis), n is further constrained as:

$$n = 2^{m/2}; \quad m \in \{0, 2, 4, \ldots\} \qquad [1]$$

In some embodiments, these constraints may be relaxed to a certain extent by selecting appropriate pixel groups that aren't exact squares or/and by selecting another appropriate basis.

Next, let $x_{k,l}$ denote an arbitrary pixel group whose starting pixels are k, l∈{1, n+1, 2n+1, ... }. Then, by simple pixel indexing:

$$x_{k,l}=X(k:k+n-1,l:l+n-1) \quad [2]$$

Define, $h_m$ as the $[2^m \times 2^m]$ (same as $[n^2 \times n^2]$) sized Hadamard matrix (FIG. 7B). Each row of $h_m$ is used to generate an encoding pattern. Consider an arbitrary $r^{th}$ row, $h_{m,r}$ $[1 \times n^2]$ sized $h_{m,r}$ (FIG. 7C) is reshaped to the [n×n] sized two-dimensional (2D) pattern $h_{m,r}$ (FIG. 7D). Then the [N×N] sized full illumination pattern, $H_{m,r}$ is formed by replicating $h_{m,r}$ onto all the pixel groups (FIG. 7E):

$$H_{m,r}(i,j)=h_{m,r}(i\%n,j\%n) \quad [3]$$

Here, % denotes the modulo operation (i.e., a % b is the remainder of a/b). The illumination pattern $H_{m,r}$ is then projected to modulate the focal FOV as shown in FIG. 7F. The modulated FOV can be expressed as:

$$Y_r(i,j)=X(i,j) \times H_{m,r}(i,j)$$

In a real-world microscopy setup, $Y_r$ is subjected to scattering. Let, sPSF(i, j) denote the scattering point spread function (FIG. 7G). The scattered $Y_{r,s}$ (FIG. 7H) can be expressed as $$Y_{r,s}=Y_r \otimes sPSF \quad [4]$$

Here '⊗' denotes the 2D convolution operation. Finally, $Y_{r,s}$ is transmitted through the microscope's optics and is received at the detector of the imaging device. Let, mPSF(i, j) be the point spread function of the microscope. Then, the detected image (FIG. 7I) can be expressed as $$\hat{Y}_r \sim Poisson(Y_{r,s} \otimes mPSF) \quad [5]$$

Here, ~Poisson(•) denotes an instance drawn from the multivariate Poisson distribution, which includes scattering functions that capture the effect of noise added by the imaging device. An ensemble of $n^2$ such images, $(\hat{Y}_1, \hat{Y}_2, \ldots, \hat{Y}_{n^2})$, can be recorded, each image corresponding to a row of $h_m$. To estimate X from $(\hat{Y}_1, \hat{Y}_2, \ldots, \hat{Y}_{n^2})$, a demodulation technique can be used.

In embodiments of systems and methods of the present application, noise-limited demodulation is possible for all pixels despite scattering and fixed partitioning of pixel groups. In some embodiments, a robust demodulation technique can be used that uses the ensemble of recorded images $(\hat{Y}_1, \hat{Y}_2, \ldots, \hat{Y}_{n^2})$ to estimate the imaged FOV, X. Let $\hat{X}$ be the estimate.

First, each pixel group can be treated as a macro pixel by summing the values of all of the pixels in the pixel group:

$$\hat{y}_{k,l,r}=\sum_{i=k}^{k+n-1}\sum_{j=l}^{l+n-1}\hat{Y}_r(i,j) \quad [6]$$

For an arbitrary pixel group $\hat{x}_{k,l}$ and an arbitrary pattern $H_{m,r}$, the macro pixel value $\hat{y}_{k,l,r}$, can be approximated as:

$$\hat{y}_{k,l,r}=\sum_{i=k}^{k+n-1}\sum_{j=l}^{l+n-1}H_{m,r}(i,j)\hat{X}(i,j) \quad [7]$$

Using the pixel group notation, the expression is modified as:

$$\hat{y}_{k,l,r}=\sum_{i=1}^{n}\sum_{j=1}^{n}h_{m,r}(i,j)\hat{x}_{k,l}(i,j) \quad [8]$$

Let $\hat{x}_{k,l}$ and $h_{m,r}$ be the $[1 \times n^2]$ sized vectored versions of [n×n] sized $\hat{x}_{k,l}$ and $h_{m,r}$. Then, $$\hat{y}_{k,l,r}=h_{m,r}\hat{x}_{k,l}^T \quad [9]$$

Here '$a^T$' denotes the transpose of a. Let $\hat{y}_{k,l}=(\hat{y}_{k,l,1}, \hat{y}_{k,l,2}, \ldots, \hat{y}_{k,l,n^2})$ be the vector containing values of the macro pixel for all the patterns. Then we can write the matrix equation $$\hat{y}_{k,l}^T=h_m\hat{x}_{k,l}^T \quad [10]$$

Here, $h_m$ is the full Hadamard matrix. By definition $h_m$ is invertible and, hence, $\hat{x}_{k,l}^T$ is given by:

$$\hat{x}_{k,l}^T=h_m^{-1}\cdot\hat{y}_{k,l}^T \quad [11]$$

Figure 8B:
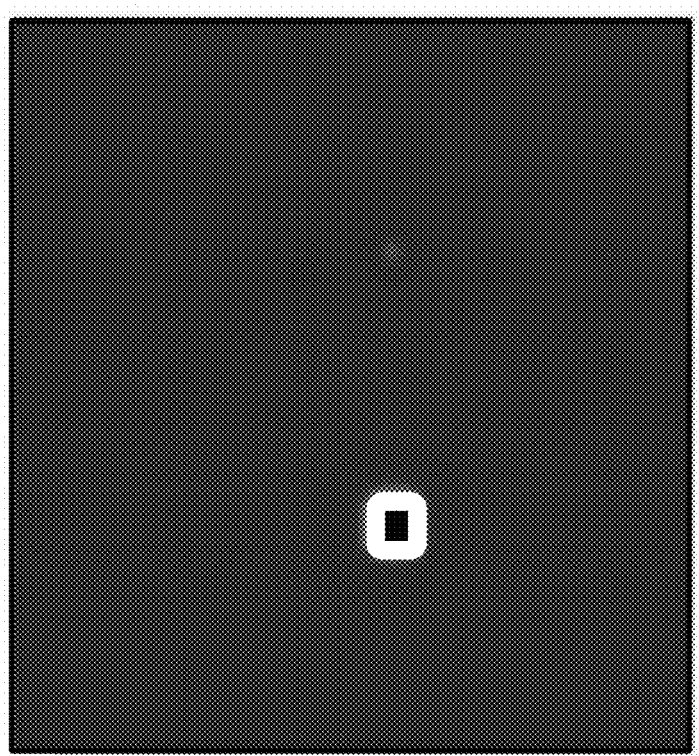
FIGS. 8A-8D illustrate simulated original, scattered, and reconstructed images using techniques described herein.
Figure 8A:
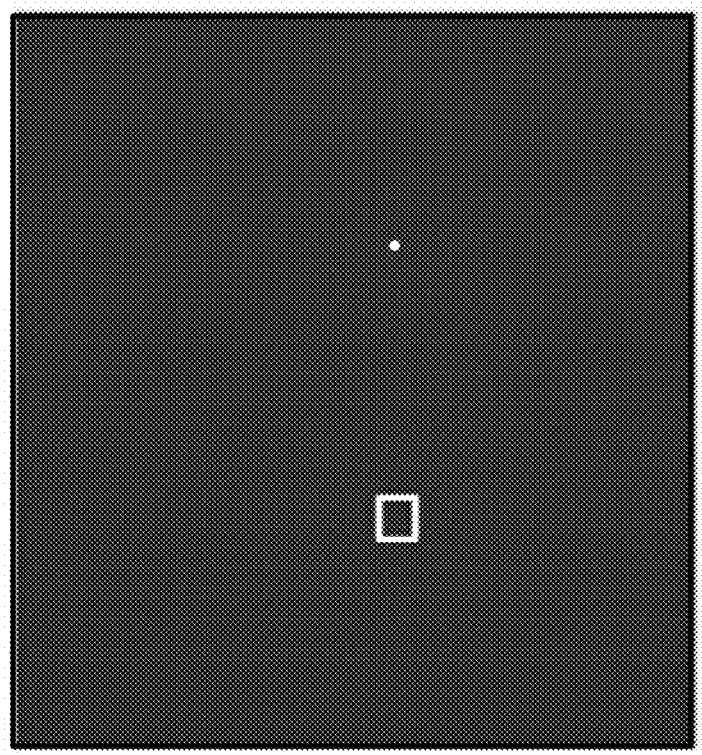
Figure 8D:
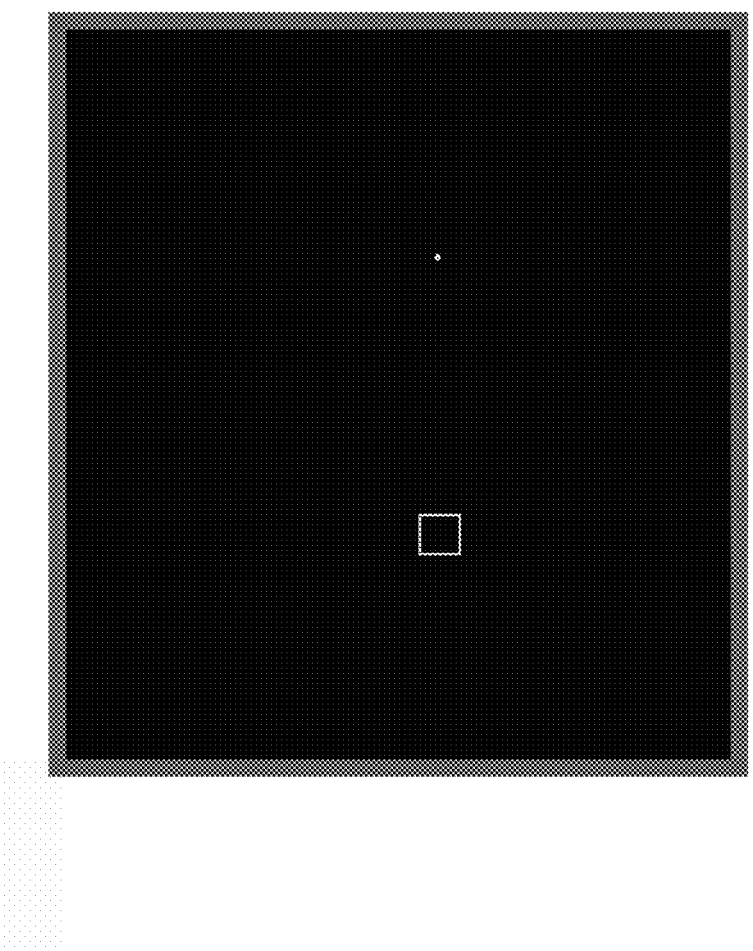
Figure 8C:
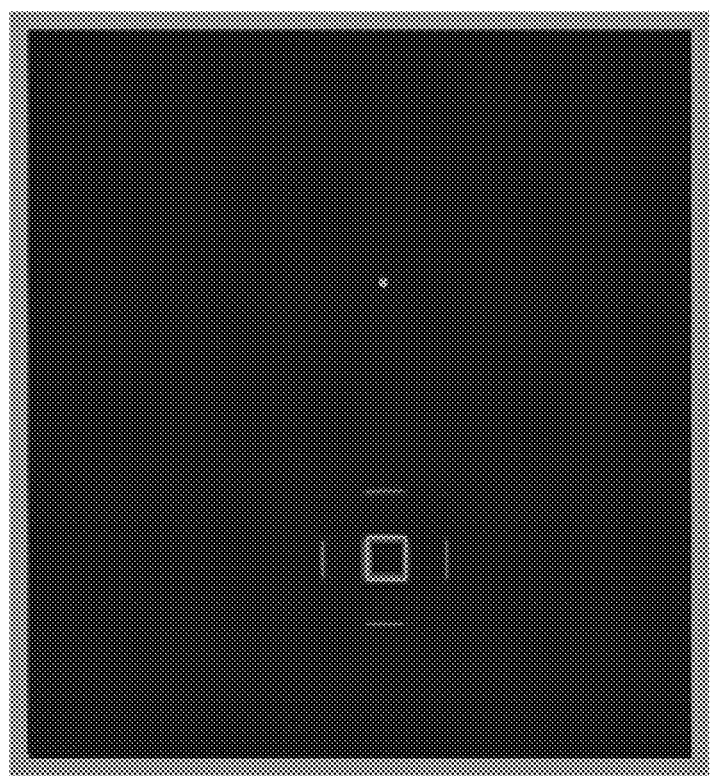
Figure 9A:
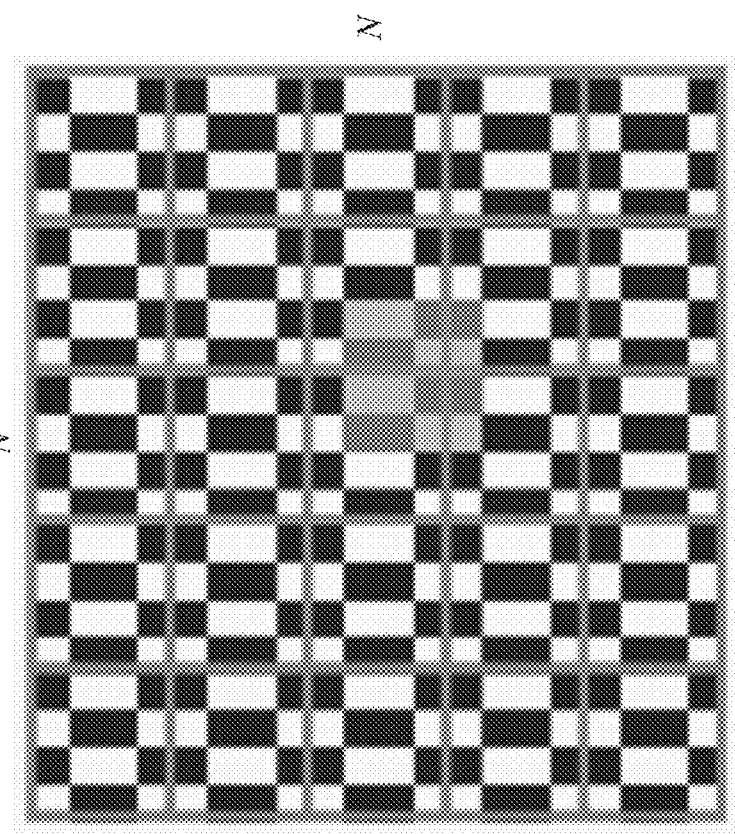
FIG. 9A illustrates a ground truth test image overlaid with encoding patterning pixel groups and an arbitrary pixel group for decoding.
Figure 9B:
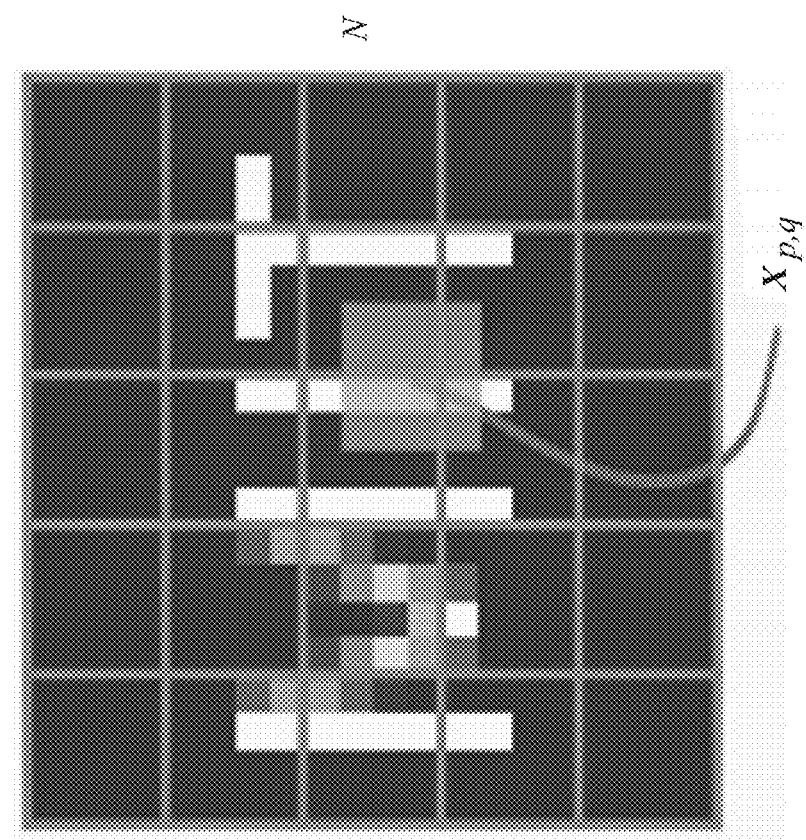
FIG. 9B illustrates a representative structured light pattern.
Figure 9C:
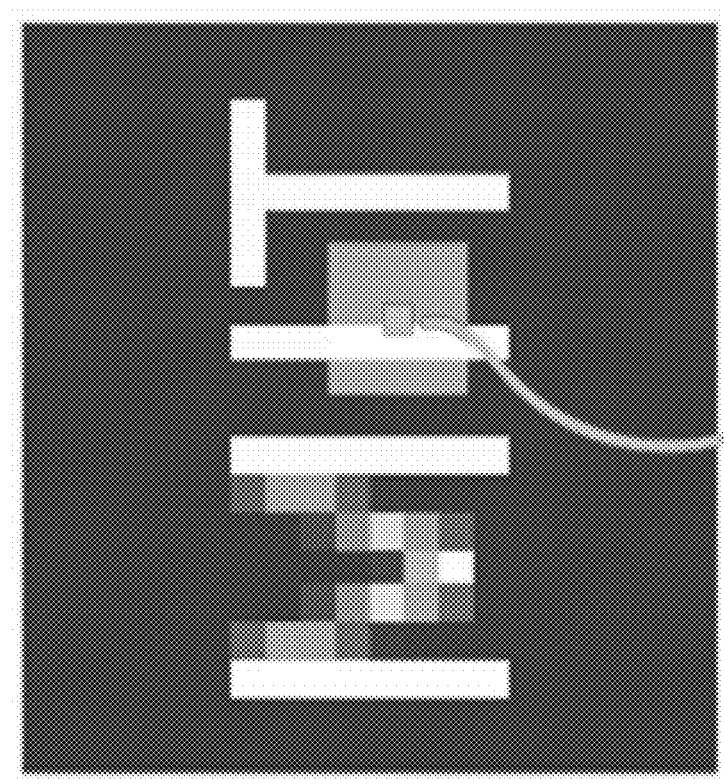
FIGS. 9C and 9D illustrate scattered and reconstructed images of the test image in FIG. 9A using techniques described herein.
Figure 9D:
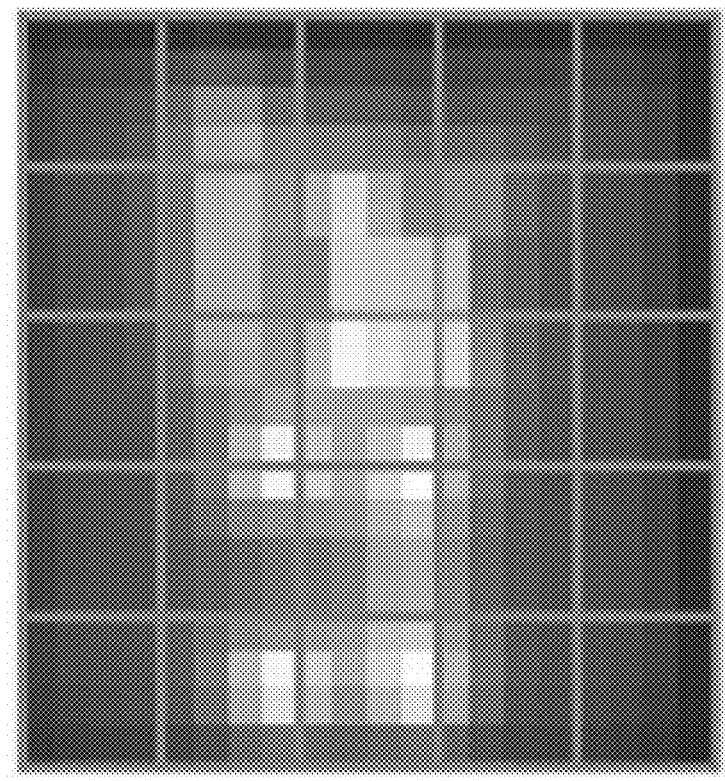

In the presence of scattering, $\hat{y}_{k,l}$ contains leaked photons from adjacent pixel groups. Thus, the reconstruction from Equation 11 (either by matrix inversion or by using any other reconstruction algorithm) is very inaccurate near the edges of the pixel groups. This phenomenon is well illustrated in FIGS. 8A-8C. FIG. 8A illustrates a simulated image with a square at the edge of a pixel group and a dot at the middle of a pixel group. FIG. 8B illustrates the scattered image with no reconstruction applied, and FIG. 8C illustrates a reconstructed image using Equation 11 wherein the original partitioning for the pixel group is maintained. As is shown, the reconstructed square includes artifacts. However, near the middle of the pixel group (i.e., the dot), the reconstruction is very accurate. Given that m (and, therefore, the pixel group size n) is preferably chosen so that no photons from neighboring pixel groups can leak to the middle pixel, the value of the middle pixel of the pixel group can be estimated to the noise limited accuracy using Equation 11.

Given this insight, consider a same [n×n] sized arbitrary virtual pixel group, $\hat{x}_{p,q}$, that spans across the boundaries of the original pixel group partitions (see the shaded pixel group in FIGS. 9A-9D):

$$\hat{x}_{p,q}=\hat{X}(p:p+n-1,q:q+n-1) \quad [12]$$

Here p, q∈(1, 2, ..., N) are the indices of the starting pixel of the pixel group. The same mathematics developed above can be developed for such a pixel group with the exception of the $h_{m,r}$ (and its downstream versions). By the definition of the pixel group, the equivalent $\bar{h}_{p,q,m,r}$ takes the following form (compare the shaded pixel group in FIG. 9B and the pixel group pattern shown in FIG. 10A);

$$\bar{h}_{p,q,m,r}(i,j)=H_{m,r}(p+i-1,q+j-1) \quad [13]$$

By substituting from Equation 3, $$H_{m,r}(p+i-1,q+j-1)=h_{m,r}((p+i-1)\%n,(q+j-1)\%n) \Rightarrow$$
$$\bar{h}_{p,q,m,r}(i,j)=h_{m,r}((p+i-1)\%n,(q+j-1)\%n) \quad [14]$$

Figure 10C:
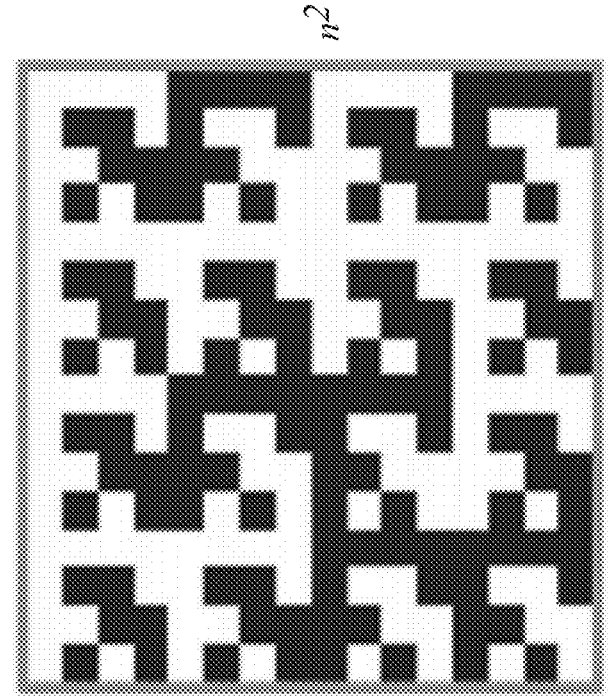

Thus, it can be seen that $\bar{h}_{p,q,m,r}$ is simply a circularly shifted version of $h_{m,r}$. In turn, $\bar{h}_{p,q,m}$, the equivalent of the full Hadamard matrix, $h_m$, is simply a columns-rearranged version of $h_m$ (FIG. 10C). It can be shown that $\bar{h}_{p,q,m}$ contains all the important properties of $h_m$. Thus, the equivalent of Equation 11 can be written as:

$$\hat{x}_{p,q}^T=\bar{h}_{p,q,m}^{-1}\cdot\hat{y}_{p,q}^T \quad [15]$$

Importantly, solving this inverse problem gives a noise limited estimate for the middle pixel of the pixel group, i.e. $\hat{x}_{p,q}(n/2, n/2)$, and hence, using Equation 12, for $\hat{X}(p+n/2-1, q+n/2-1)$. Because p, q were arbitrarily selected, this result means that any arbitrary pixel in the image can be estimated to a noise limited accuracy despite scattering and fixed partitioning of the FOV. As an example, FIG. 8D illustrates an estimated image of FIG. 8B using arbitrary partitioning in accordance with Equation 15. The image is improved over the version shown in FIG. 8C using reconstruction on the fixed partitioning.

Figure 11B:
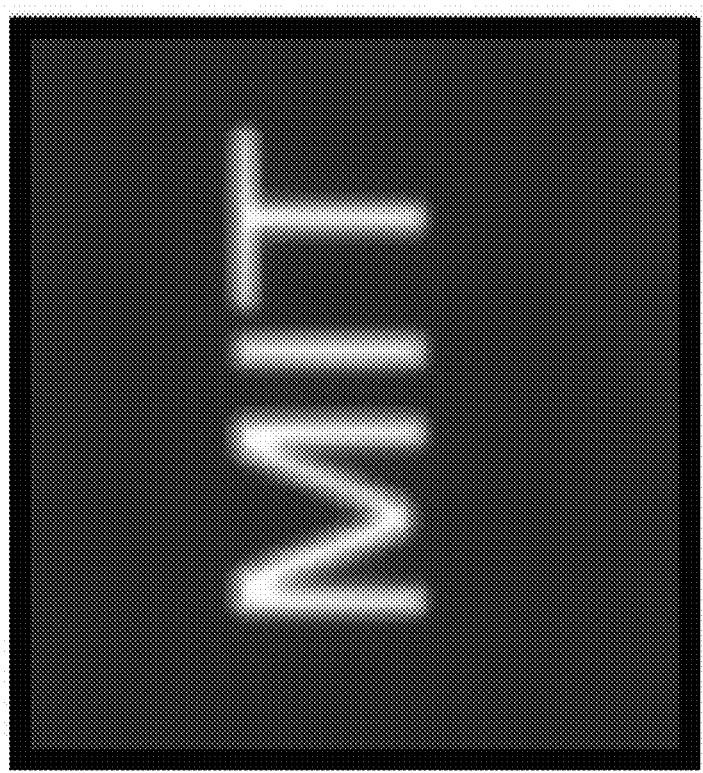
FIGS. 11A-11D illustrate simulated original, scattered, and reconstructed images through a 100 µm thick scattering layer using systems and methods described herein.
Figure 11A:
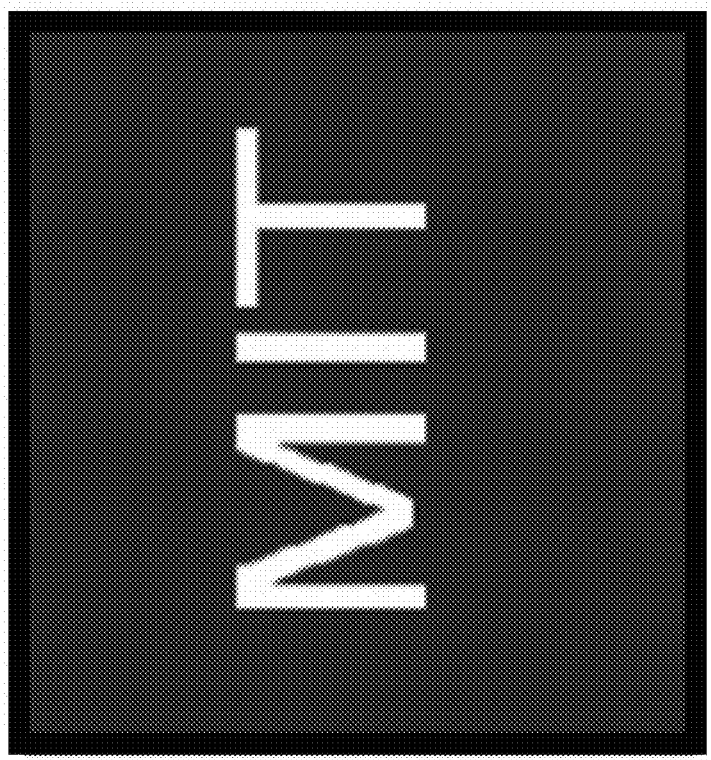
Figure 11C:
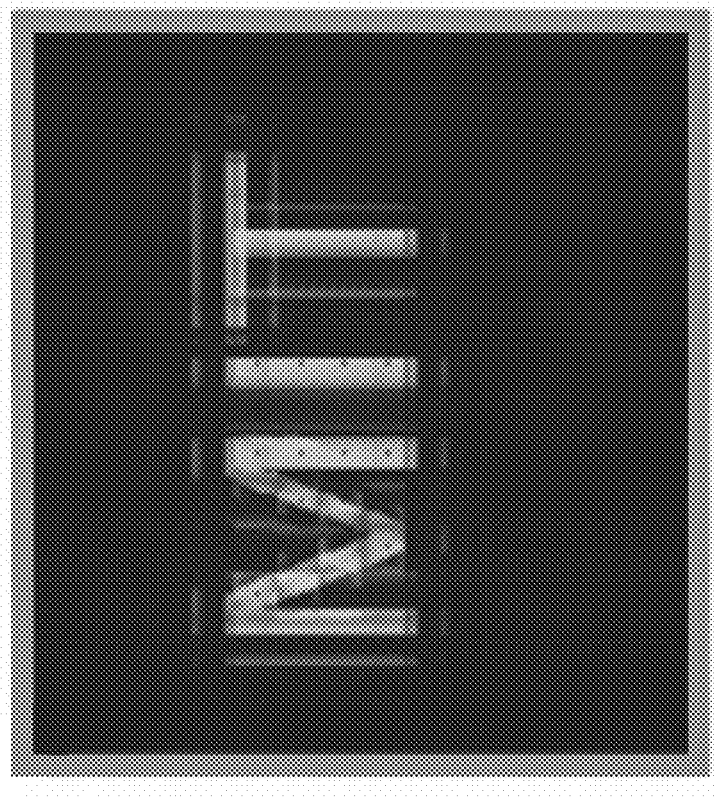
Figure 11D:
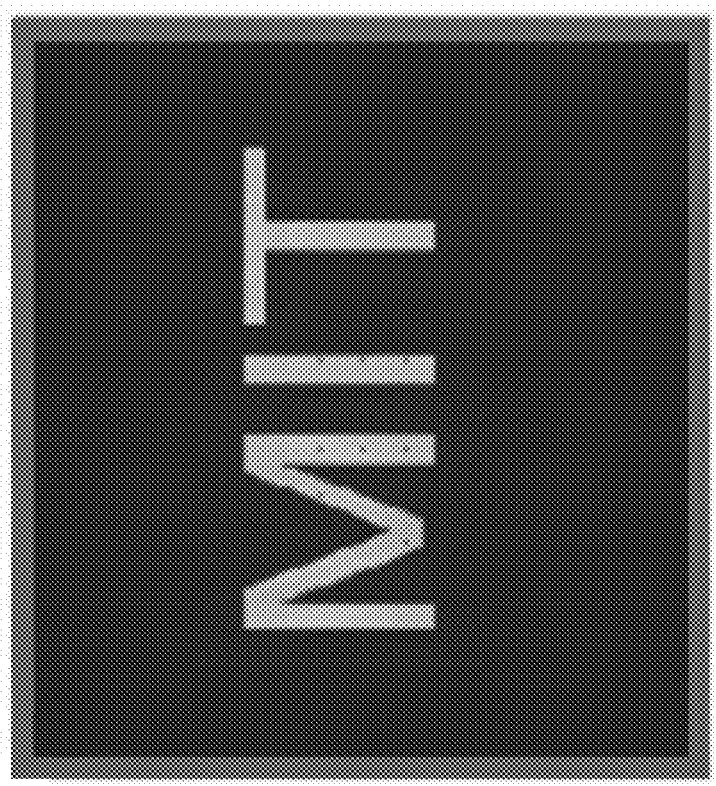
Figure 12B:
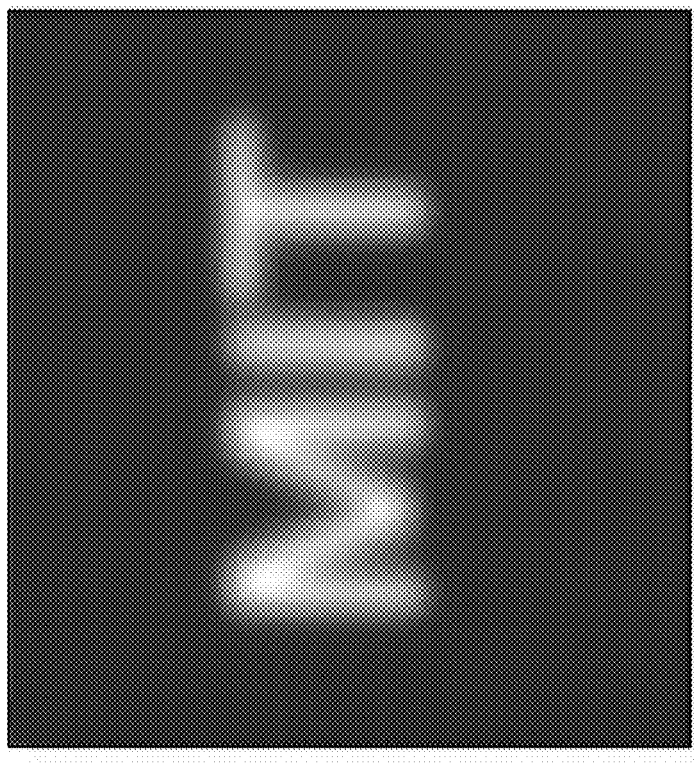
FIGS. 12A-12D illustrate simulated original, scattered, and reconstructed images through a 200 µm thick scattering layer using systems and methods described herein.
Figure 12A:
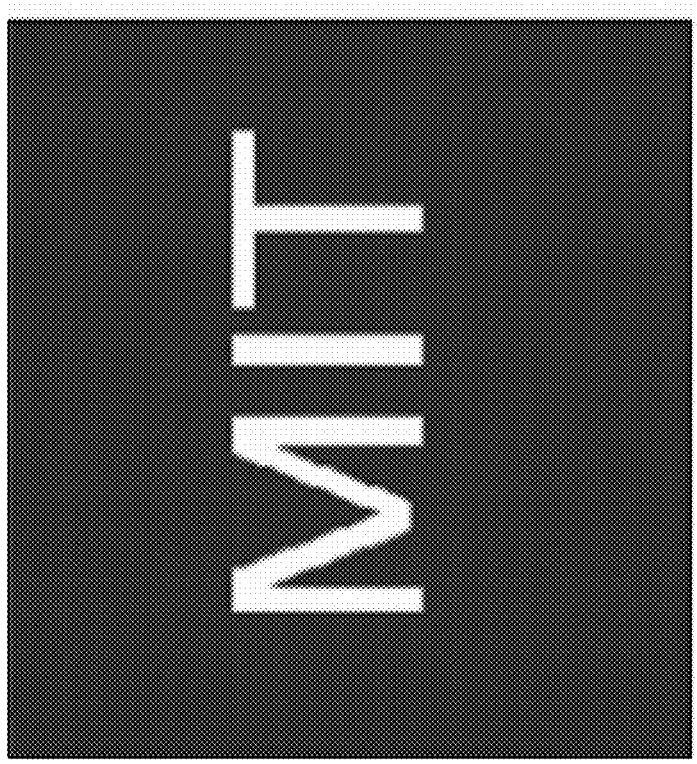
Figure 12C:
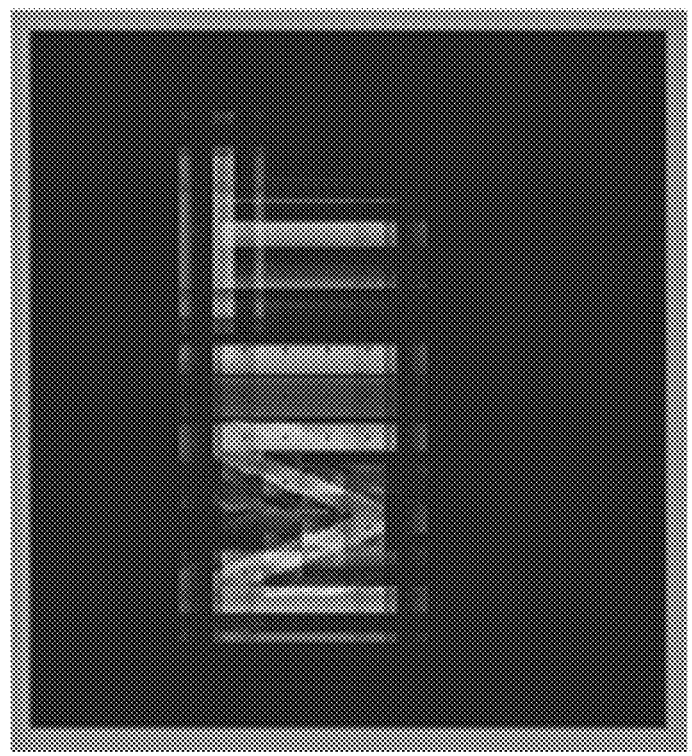
Figure 12D:
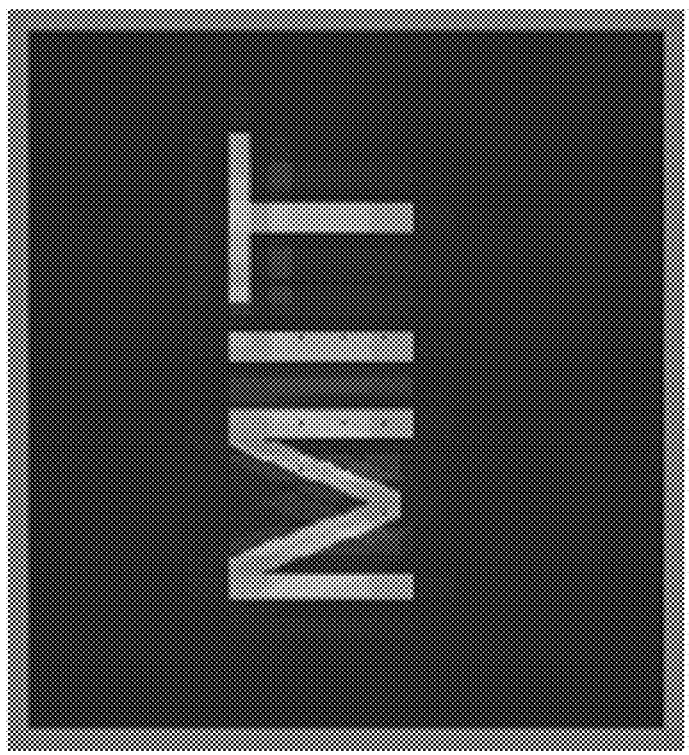

FIGS. 11A-11D and 12A-12D show estimates of the effect of the reconstruction technique described herein using Equation 11 and Equation 15 for two simulated scattering layers. The set of FIGS. 11A-11D illustrate the effect on imaging of a 100 μm thick scattering layer while FIGS. 12A-12D illustrate the effect on imaging of a 200 μm thick scattering layer. FIGS. 11A and 12A illustrate simulated original images to be reconstructed while FIGS. 11B and 12B illustrate the simulated scattered images of FIGS. 11A and 12A, respectively, through their relative scattering layers. FIGS. 11C and 12C illustrate the estimated images of FIGS. 11B and 12B using Equation 11, i.e., fixed original partitioning. FIGS. 11D and 12D illustrate the estimated images of FIGS. 11B and 12B using Equation 15, i.e., arbitrary virtual partitioning.

Decomposing the imaging FOV into multiple virtual blocks followed by performing a local (e.g., 16×16) pixel Hadamard scan on each block can overcome limitations associated with the frame rate of single-pixel cameras, which is set by the number of illumination patterns needed for the image acquisition and is traditionally governed by the Nyquist rate. The local Hadamard scan can be followed by the measurement of the net fluorescence associated with each block on a binned group of camera pixels. The parallel nature of this architecture enables >80 frames per second acquisition rate independent of the FOV.

In some embodiments, additional denoising can be applied to the images before or after reconstruction. Image denoising works on the principle that the images contain sparse structures and the noise is drawn from a well characterized distribution. As an example, most images are sparse in the wavelet basis and most detected images contain noise drawn from the Poisson distribution. Therefore, once a sparse representation of an image and its noise distribution are identified, one could solve Equation 11 or Equation 15 as a convex optimization problem along with an additional regularization term such as the L1 norm. Alternatively, one could perform image denoising on the original intermediate images acquired by the imaging device prior to applying the reconstruction techniques of the systems and methods disclosed herein. In some embodiments, in order to make the maximum use of object structures that span multiple pixel groups considered herein, one could start with a sparse representation of the image (such as a wavelet representation) and perform an equivalent global optimization of Equation 11 or Equation 15).

The systems and methods described herein can employ a compressive sensing scheme to improve data acquisition speed further without significantly impacting image resolution. In some embodiments, a compressed-sensing-aided temporal focusing approach can help overcome depth limitations on wide-field temporal focusing and push the previous limits on wide-field imaging depth. In a compressive sensing framework, an N dimensional sparse signal, $x \in R^N$, can be decomposed as a sparse vector $a \in R^N$ in a basis W as:

$$x = Wa \quad [16]$$

According to compressive sensing theory, perfect reconstruction is possible by measuring M incoherent projections ($y_k$, k=1, ..., M) of x with a sensing matrix φ:

$$y = \phi x \quad [17]$$

In exemplary embodiments, $\phi_k$ (a row of matrix φ) can be an illumination pattern that can be generated by the structured illumination device.

Figure 13:
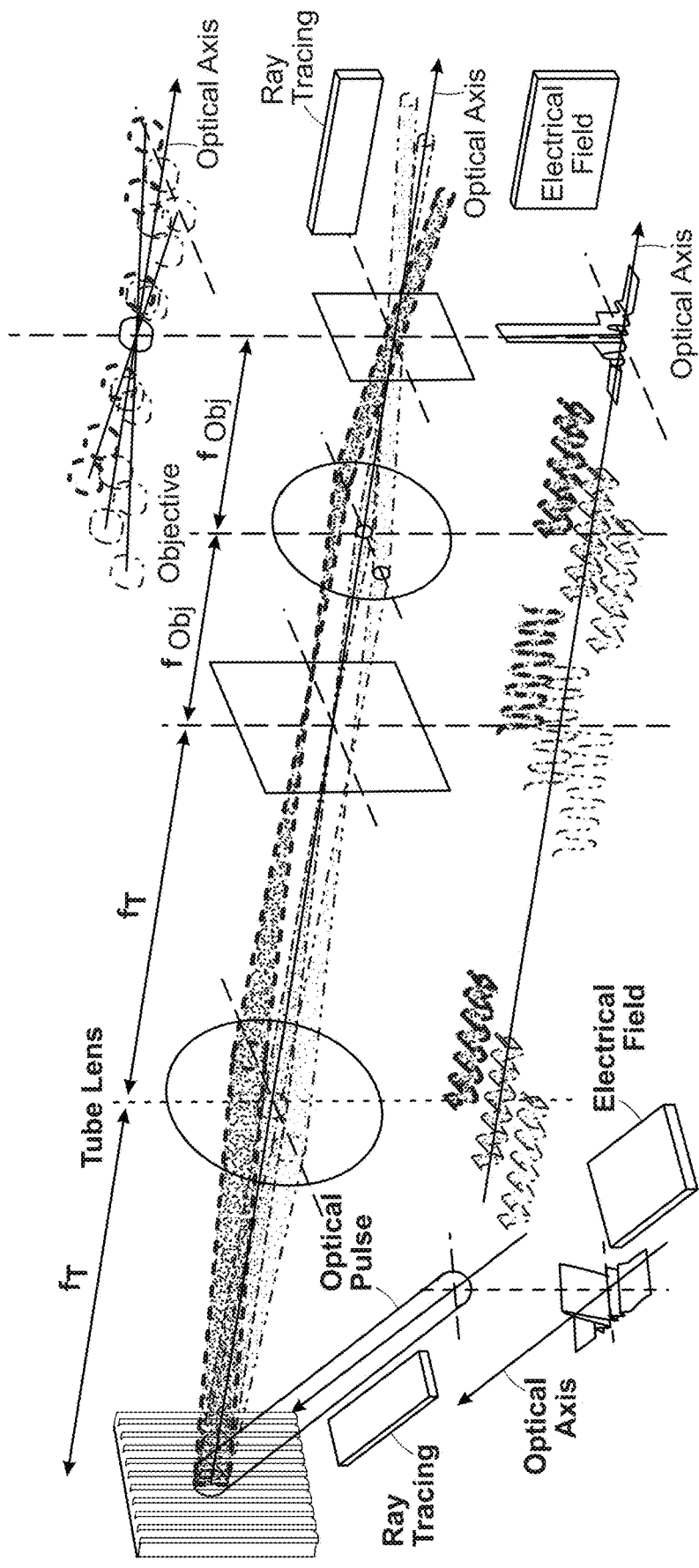
FIG. 13 illustrates an exemplary optical setup that is compatible with compressive-sensing-based temporal focusing microscopy as described herein.
Figure 14:
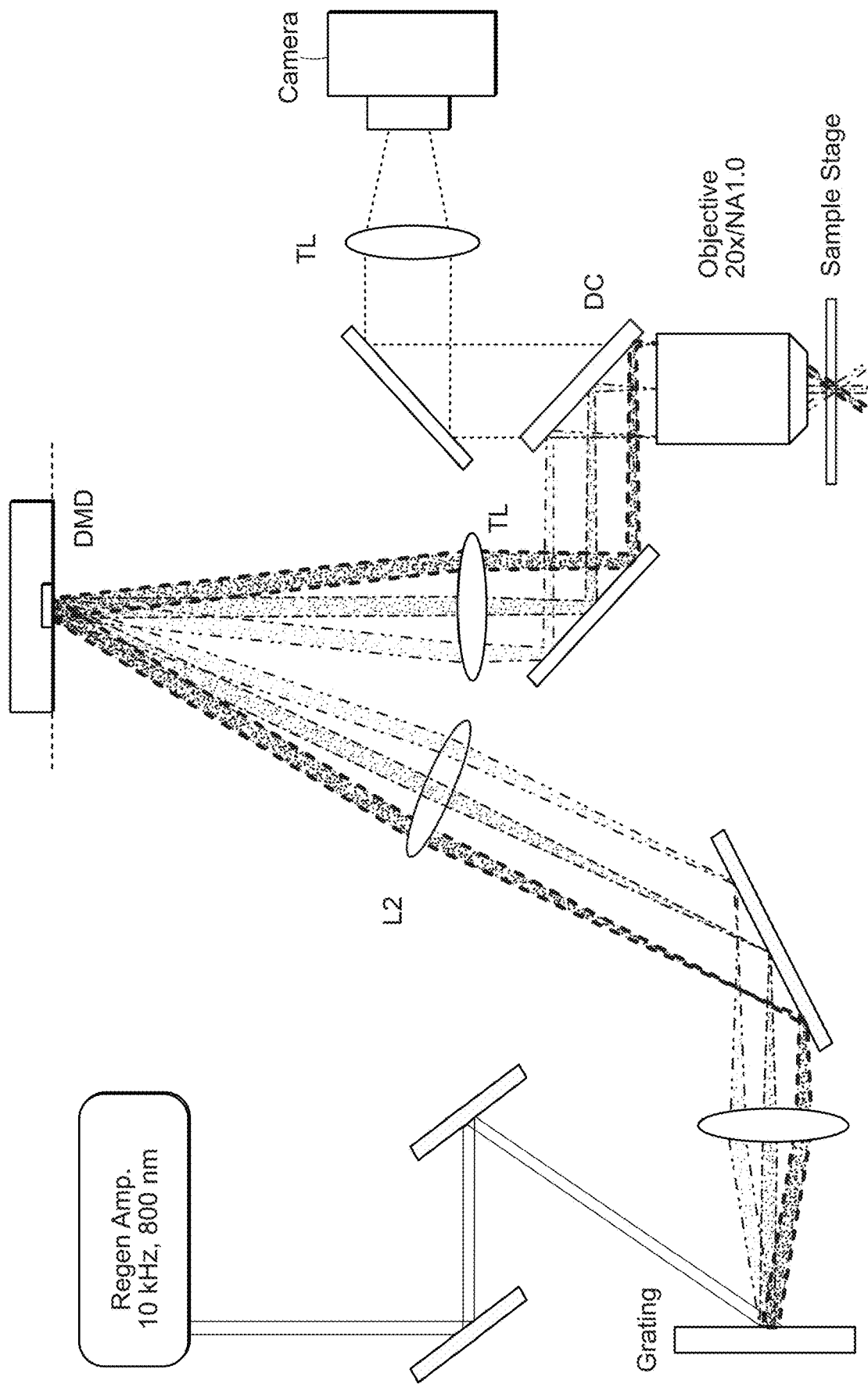
FIG. 14 illustrates an exemplary optical setup that is compatible with compressive-sensing-based temporal focusing microscopy as described herein.

FIGS. 13 and 14 show exemplary optical setups that are compatible with compressive-sensing-based temporal focusing microscopy as described herein.

Figure 15:
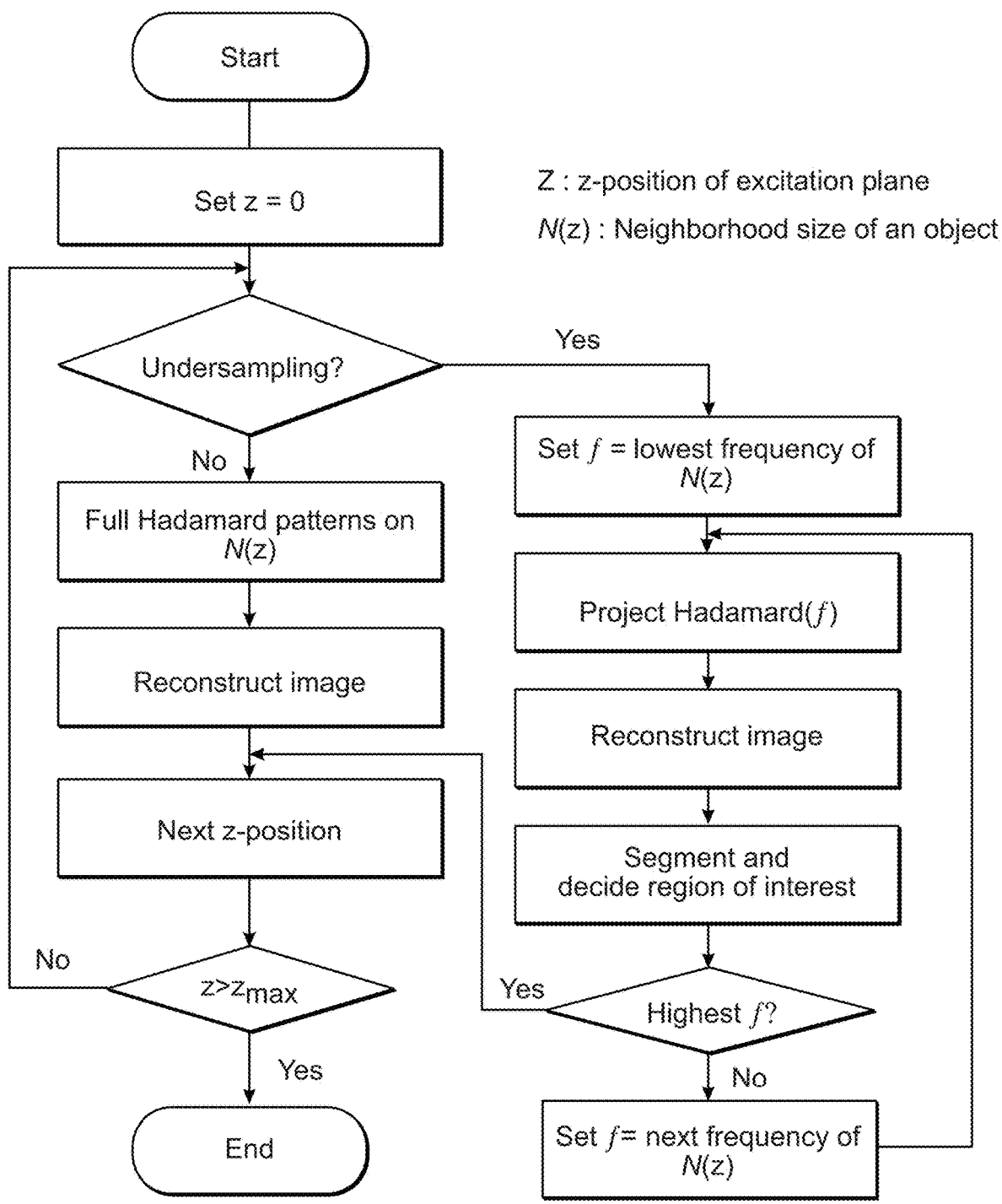
FIG. 15 presents a flowchart for various schemes for image acquisition along different pathways including traditional image reconstruction processes and reconstruction using a compressive sensing algorithm.

FIG. 15 presents a flowchart for various schemes for image acquisition along different pathways including traditional image reconstruction processes and reconstruction using a compressive sensing algorithm.

Figure 16B:
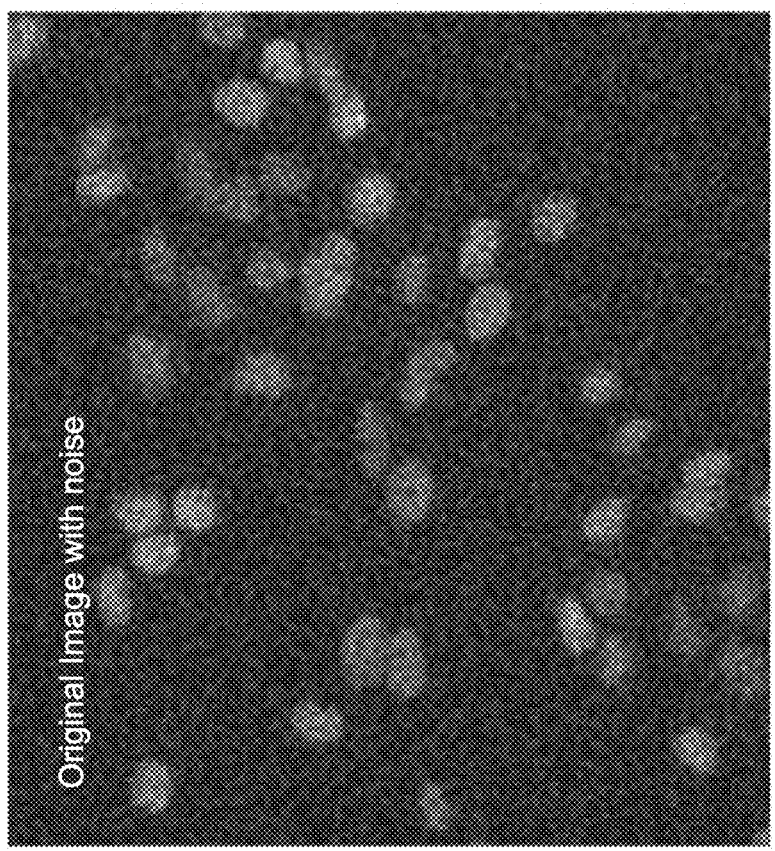
FIGS. 16A-16C illustrate a simulated reconstruction of sample data from a noisy image using Hadamard basis-modulated detector measurements.
Figure 16A:
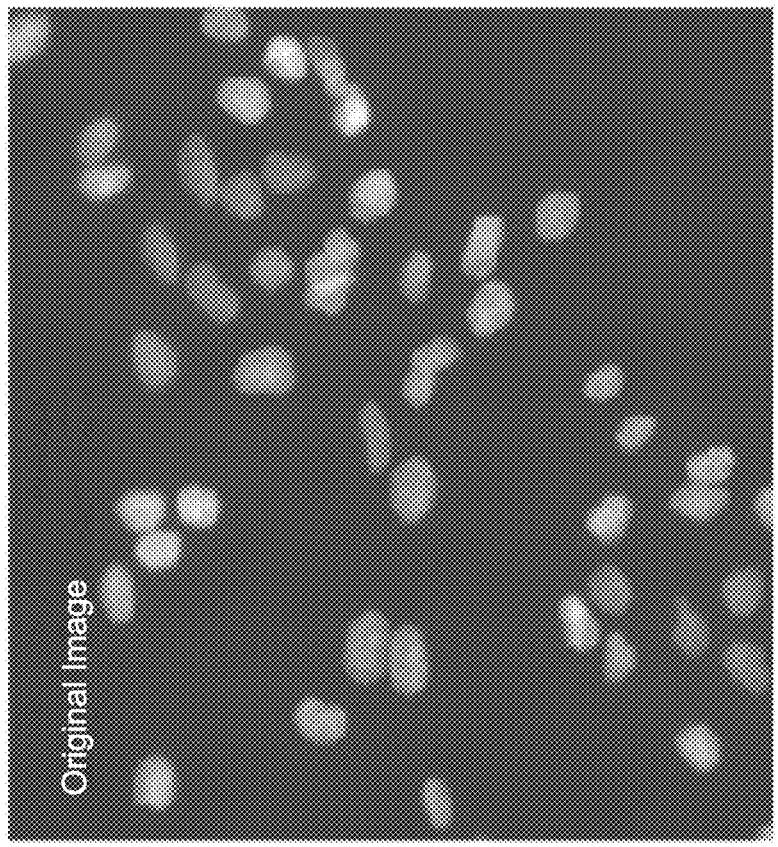
Figure 16C:
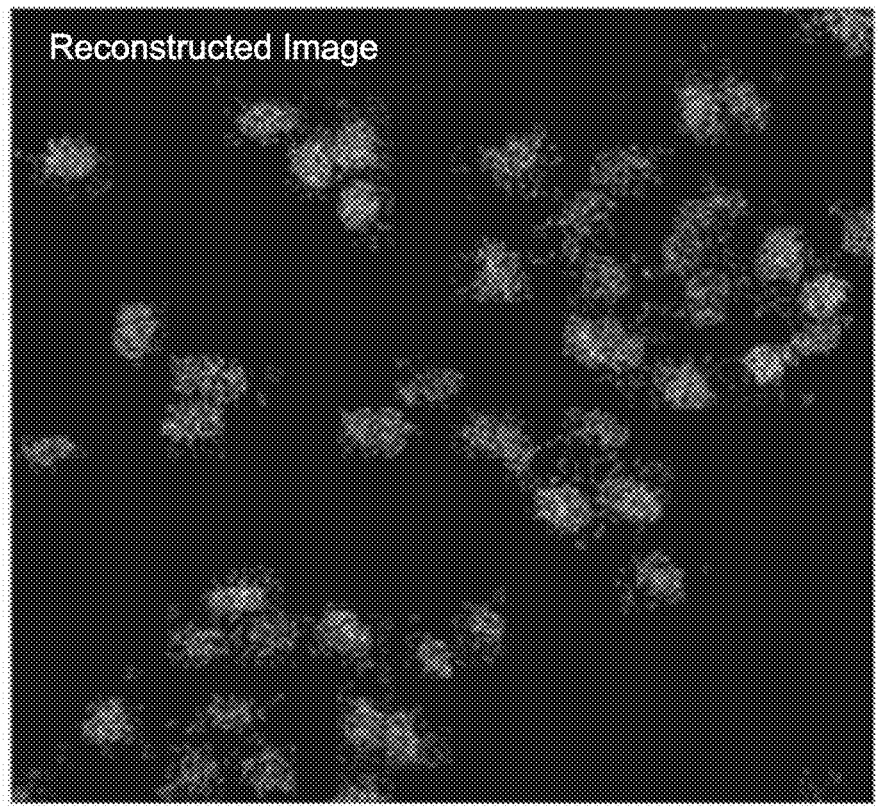

FIGS. 16A-16C illustrate a simulated reconstruction of sample data from a noisy image using Hadamard basis-modulated detector measurements. FIG. 16A illustrates the original image while FIG. 16B illustrates the original image with added noise as might be experienced in a real-world imaging situation. For example, the added noise can correspond to background and scattering noise that is found in a deep sample image. FIG. 16C illustrates the reconstructed image.

In various embodiments, arbitrary pattern projection temporal focusing microscopy methods can be combined with a compressive sensing framework to speed up image acquisition times even further. Because the modulation patterns used (e.g., derived from a Hadamard basis or random basis as described above) can be treated as incoherent measurement matrices, an incomplete sensing matrix can be used when the underlying image contains a sparse representation. In other words, one does not have to use all the patterns in such setting. Rather, a subset of patterns may be used for data acquisition and accurate reconstruction via the compressive sensing architecture. In some embodiments, the same algorithms for denoising mentioned above can be used for this purpose as well. Examples of algorithms and methodologies for denoising and compressed sensing that are suitable for use with the techniques described herein can be found in "Performance Bounds for Expander-Based Compressed Sensing in Poisson Noise" by M. Raginsky et al., *IEEE Transactions on Signal Processing*, vol. 59, no. 9, September 2011, "Wavelets, Ridgelets, and curvelets for Poisson noise removal" by B. Zhang et al., *IEEE Transactions on Image Processing*, vol. 17, no. 7, January 2008, and "Poisson Compressed Sensing" by R. Willett and M. Raginsky, available at http://willett.ece.wisc.edu/wp-uploads/2016/01/PCS.pdf, the entire content of all of these publications being incorporated herein by reference in their entireties. Compressive sensing approaches can be especially useful at larger imaging depths where the pixel group size has to be increased to cover the greater extent of scattering that is experienced at such depths. In such cases, the number of patterns needed is large, and the ability to use only a subset of them can be very useful to increase imaging speed. In some embodiments, the level of sparsity necessary to achieve the necessary level of accuracy in the reconstruction can be estimated.

Figure 17:
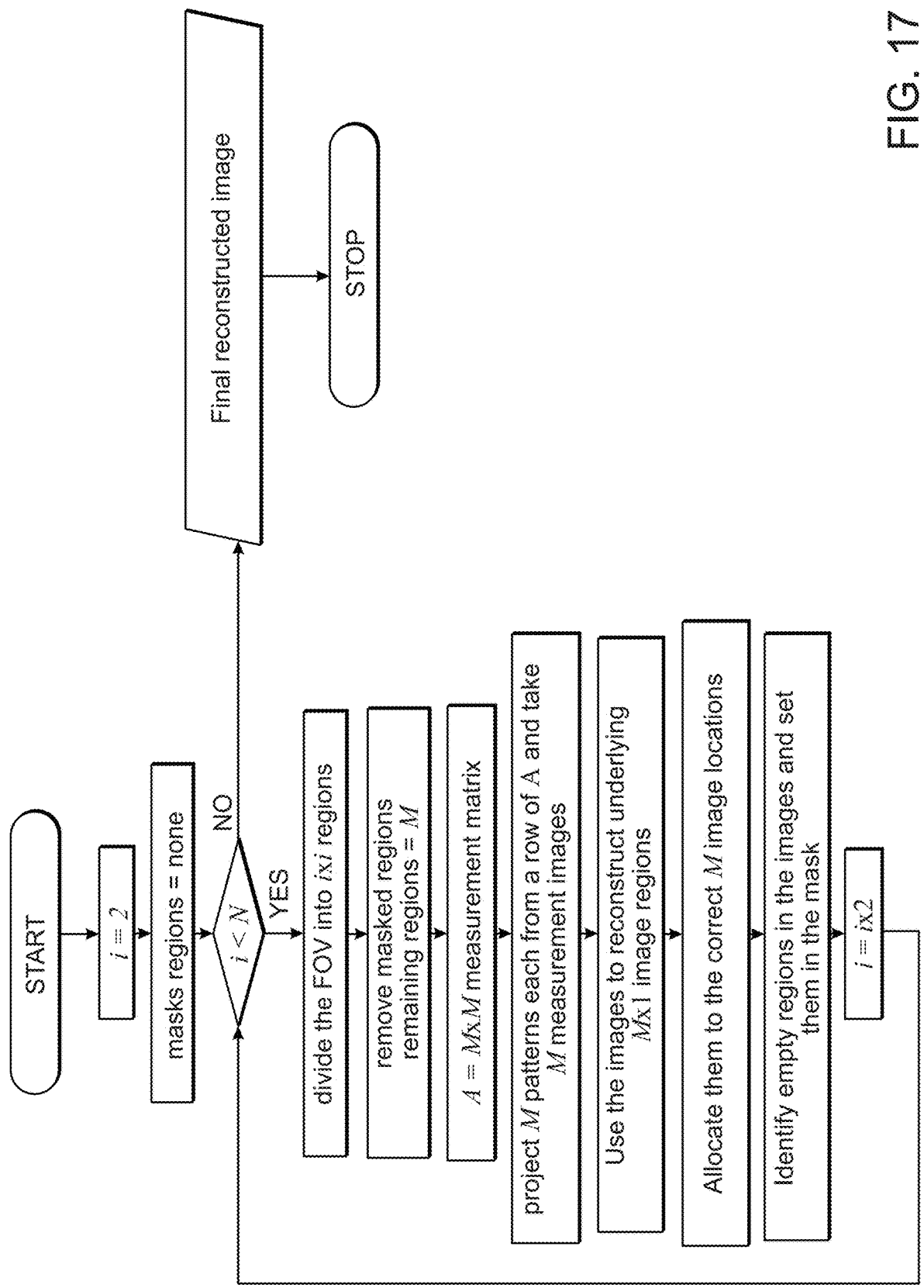
FIG. 17 illustrates a scheme for imaging using iterative selection of a subset of patterns from the pattern basis using compressive sensing techniques.

FIG. 17 illustrates a scheme for imaging using iterative selection of a subset of patterns from the pattern basis using compressive sensing techniques. Other strategies can also be utilized for compressive like reconstruction with a lower number of patterns than that in the full basis set. In some embodiments, systems and methods disclosed herein can use a small set of projected patterns and their associated recorded images to reconstruct an estimation of the underlying ground truth image. Based on this estimate, the next best set of patterns that may be projected can be calculated to provide a more refined image. This process can be repeated a number of times until an accurate image is reconstructed. This technique may be especially useful for deeper imaging planes where the scattering distortion is large.

Figure 18:
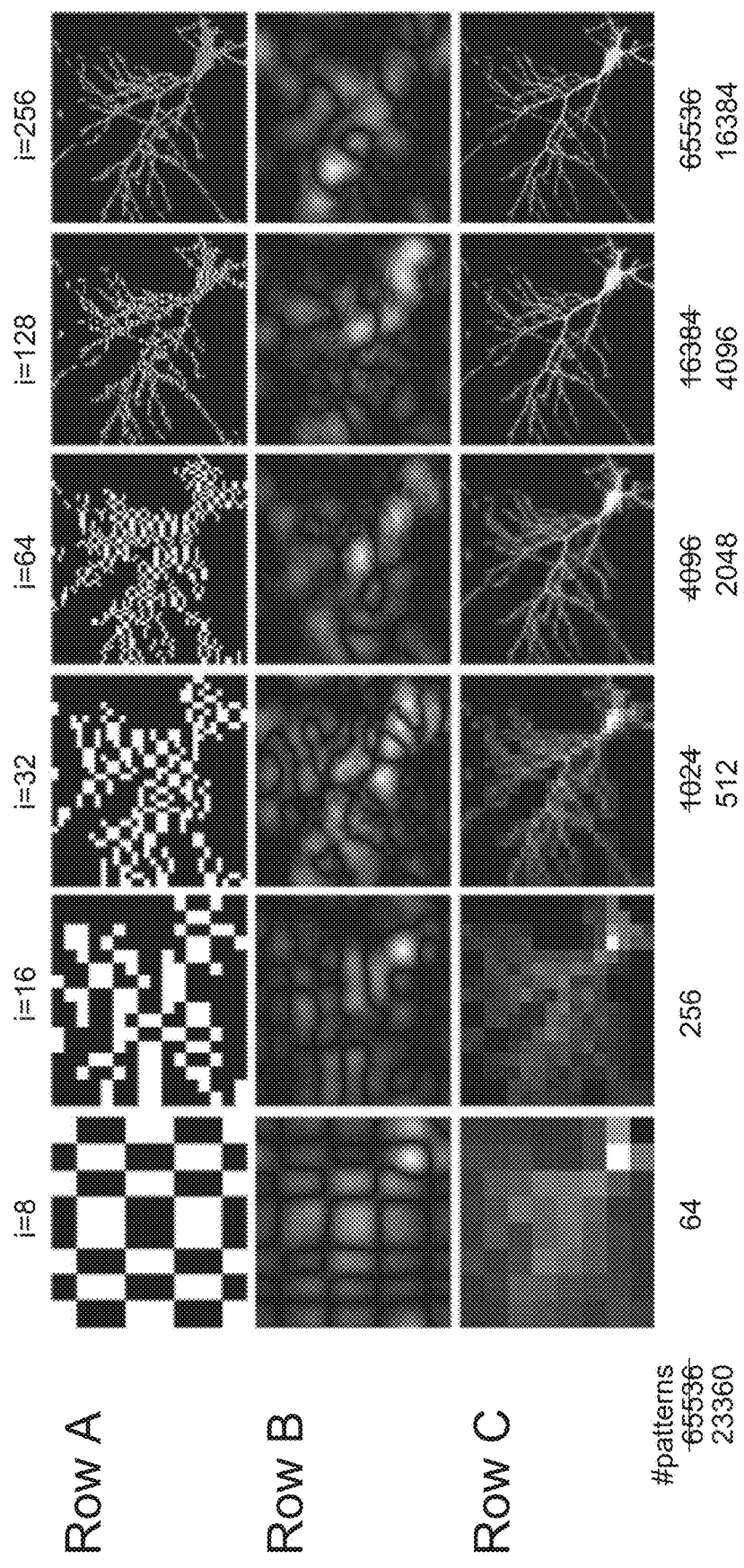
FIG. 18 shows the results of a reconstruction of a 256×256 image using compressive-sensing and arbitrary pattern projection methods as described herein.

Consider an imaging depth that is affected by scattering so completely that the entire area of the imaging device has to be treated like a single pixel group. In such a case, the number of patterns that are needed in the full basis set is equal to the number of pixels in the camera. As an example, for a camera with 256×256 pixels (i.e., at least 400,000 pixels), a total of 65536 patterns are needed. FIG. 18 shows the results of a reconstruction of a 256×256 image using this method. Row A shows a representative pattern projected at the $i^{th}$ iteration as described above and in FIG. 17. Row B shows the corresponding image recorded on the camera. Row C shows the estimated image at each iteration of the flow chart using reconstruction. Note that due to intermediate reconstruction estimations, only the object regions are refined in later iterations. As illustrated the total number of patterns used was 23360 instead of 65536. This represents a significant reduction in the number of patterns that need to be displayed without a concomitant loss in resolution in the final image.

Mathematically, the De-scattering with Excitation Patterning Temporal Focusing Microscopy (DEEP-TFM) imaging process can be modeled by the following equation.

$$Y_t(x,y) = sPSF(x,y) * \{(exPSF(x,y) * \tilde{H}_t(x,y)) \cdot X(x,y)\} \quad (18)$$

Here x, and y are spatial coordinates; t is the time; exPSF(x, y), and sPSF(x, y) are the excitation and scattering point spread functions; $\tilde{H}_t(x, y)$ is the $t^{th}$ modulation pattern projected by the DMD. X(x, y) is the object being imaged; $Y_t(x, y)$ is the $t^{th}$ image acquired on the camera. The operators * and · represent spatial convolution and pixel wise multiplication, respectively. More particularly:

$$x \in \{x' \in Z: -N_x/2 \leq x' \leq N_x/2-1\}$$

$$y \in \{y' \in Z: -N_y/2 \leq y' \leq N_y/2-1\}$$

$$t \in \{1, 2, \ldots, N_t\}$$

X(x, y): Imaged field-of-view of the sample
$\tilde{H}_t(x, y)$: $t^{th}$ spatial excitation modulation pattern
exPSF(x, y): Excitation point spread function, $\Sigma_x \Sigma_y$ exPSF(x, y)=1
sPSF(x, y): Scattering point spread function, $\Sigma_x \Sigma_y$ sPSF (x, y)=1
$Y_t(x, y)$: $t^{th}$ acquired image in no-noise conditions
·: Hadamard product
*: 2D convolution over x, y
$\mathcal{F}$ g (kx, ky): Spatial Fourier transform of g(x, y).
kx, ky: Respective frequencies in x, and y.

Re-writing Equation 18 in the spatial Fourier domain gives:

$$\mathcal{F} Y_t(kx,ky) = \mathcal{F} sPSF(kx,ky) \cdot \{(\mathcal{F} exPSF(kx,ky) \cdot \mathcal{F} \tilde{H}_t(kx,ky)) * \mathcal{F} X(kx,ky)\} \quad [19]$$

Assuming N pixels (both in the image, $Y_t$, and the object, X), the above equation has 2N unknowns (N in $\mathcal{F}$ X, and N in $\mathcal{F}$ sPSF). As written, each measurement (i.e. an image taken at time point t) appears to provide N equations. However, $\mathcal{F}$ sPSF acts as a low-pass filter, and for out-band frequencies (out of the frequency support of $\mathcal{F}$ sPSF), the right-hand side of Equation 19 is zero. Now, assume that $\mathcal{F}$ sPSF's frequency support has M pixels. Then, each measurement provides M independent equations. Thus, for the above system of equations to be solvable, we need $N_t > 2N/M$ measurements. For deep tissue imaging applications, the frequency support of $\mathcal{F}$ sPSF changes with imaging depth. As there's no scattering at the surface, at the surface M~N; we only need $N_t = O(1)$ measurements (here 'O(·)' represents the asymptotic 'big-O' notation). At deep locations within the tissue where there is no spatial information on the obtained images, M~1. We hence need $N_t = O(N)$ measurements. Please also note that because of the frequency domain convolution between $\mathcal{F} \tilde{H}_t$ and $\mathcal{F} X$ (Equation 19), out-band frequencies (of the frequency support of $\mathcal{F}$ sPSF) in X are still sampled on to $Y_t$ as long as $\mathcal{F} \tilde{H}$ captures all possible frequencies of X. It can be shown that a random pattern of $\tilde{H}$ satisfies this criterion (described below). Thus, an ensemble of O(2N/M) random patterns, $\{\tilde{H}_t\}$, can be used to fully measure X in DEEP-TFM. Upon such measurement, some systems and methods herein record an ensemble of $\{Y_t\}$ images corresponding to $\{\tilde{H}_t\}$; X can be reconstructed using $\{Y_t\}$ and $\{H_t\}$ by solving Equation 18 or its corresponding frequency domain representation, i.e., Equation 19.

In practice we make noisy measurements of Y(x, y, t).

$$\tilde{Y}(x,y,t) \sim \text{Poisson}(Y(x,y,t)) \quad [20]$$

Here, ~Poisson(•) represents that the observations are drawn from a Poisson distribution according to a scattering function in the form of a shot noise model.

The imaging task is twofold: designing the modulation patterns $\tilde{H}(x, y, t)$ so that Equation 20 constitutes a fully determined system and estimating X(x, y) from noisy observations $\tilde{Y}(x, y, t)$.

In some embodiments, the design criteria for $\tilde{H}$ can include the following considerations:
1. Select $\{\tilde{H}_t(x, y)\}$ such that $\forall(x, y), \tilde{H}(x, y) \in \{0,1\}$
2. Select $\{\tilde{H}_t(x, y)\}$ such that $\forall(x, y), \Sigma_t(2\tilde{H}_t(x, y)-1)=0$
3. Select $\{\tilde{H}_t(x, y)\}$ such that $\forall t$ and (kx, ky), $\mathcal{F} \tilde{H}_t(kx, ky) > 0$ Implementing the modulation patterns ($\{\tilde{H}_t\}$ in Equation 20) in some optical hardware has an important restriction. For certain embodiments such as those that use a digital micromirror device 315 for pattern projection, the elements of $\tilde{H}_t$ can only be binary entries, i.e. $\tilde{H}_t(x, y) \in \{0,1\}$ as embodied above in Design criterion 1. However, this condition causes Equation 19 to become noise unstable as described in greater detail in a journal article by Maxim Raginsky, et al. entitled "Compressed sensing performance bounds under Poisson noise." *IEEE Transactions on Signal Processing* 58.8 (2010): 3990-4002, the entire contents of which in incorporated herein by reference.

Therefore, $$\tilde{H}_t = (\tilde{H}_t+1)/2$$

$$\Rightarrow H_t(x,y) \in \{-1,+1\} \quad [21]$$

Substituting into Equation 20 gives:

$$2Y = sPSF*\{(exPSF*(H_t+1))\cdot X\}$$

$$\Rightarrow 2Y = sPSF*\{(exPSF*H_t)\cdot X+(exPSF*1)\cdot X\}$$

$$\Rightarrow 2Y = sPSF*\{(exPSF*H_t)\cdot X+X\}$$

$$\Rightarrow 2Y = sPSF*\{(exPSF*H_t)\cdot X\}+sPSF*X \quad [22]$$

Please note that we have dropped the (x, y) indexing and written the variables in their proper matrix form for convenience. Here 1 is the matrix with all 1 entries.

Summing Equation 22 over all $t \in \{1, 2, \ldots, N_t\}$ gives $$\Sigma_{\forall t} Y_t = sPSF*\{(exPSF*\Sigma_{\forall t}H_t)\cdot X+N_t X\} \quad [23]$$

Let's select $\{H_t\}$ such that $\Sigma_{\forall t} H_t = 0$ (Design criterion 2). Here 0 is the all 0 matrix of the same size as $H_t$. Then we can simplify Equation 23 as, $$\Sigma_{\forall t} Y_t = N_t(sPSF*X)$$

$$\bar{Y} = (\Sigma_{\forall t} Y_t)/N_t = (sPSF*X) \quad [24]$$

Here $\bar{Y}$ is the time average of $\{Y_t\}$. Substituting Equation 24 into Equation 22 gives $$2Y_t - \bar{Y} = sPSF*\{(exPSF*H_t)\cdot X\}$$

$$\acute{Y}_t = sPSF*\{(exPSF*H_t)\cdot X\} \quad [25]$$

Using the convolution theorem, Equation 25 as represented in the spatial frequency domain gives:

$$\mathcal{F}\acute{Y}_t = \mathcal{F}\text{sPSF} \cdot \{(\mathcal{F}\text{exPSF} \cdot \mathcal{F} H_t)^* \mathcal{F} X\} \quad [26]$$

While $\mathcal{F}$sPSF acts as a low-pass filter, high spatial frequencies in $\mathcal{F}X$ can still be captured by the convolution with $\mathcal{F}$exPSF·$\mathcal{F}H_t$, given that $\mathcal{F}H_t$ contains all possible frequencies as shown in FIGS. 19A-I (Design criterion 3).

Figure 19A:
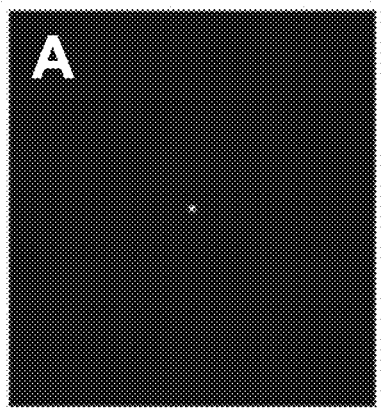
FIGS. 19A-19I illustrate the improvement provided by systems and method described herein over conventional systems when imaging objects containing high-frequency information.
Figure 19B:
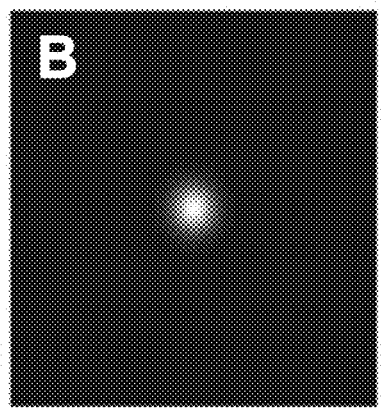
Figure 19C:
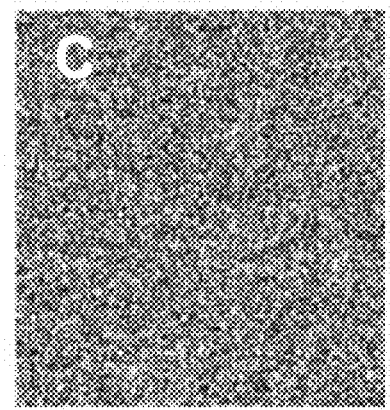
Figure 19D:
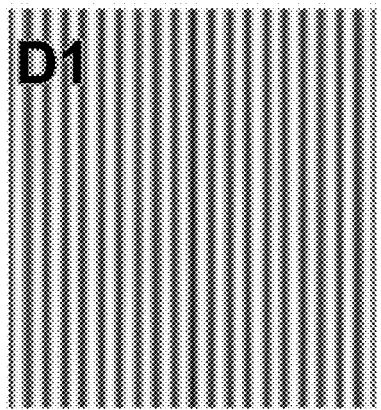
Figure 19E:
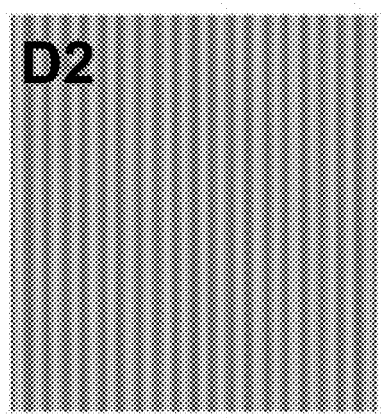
Figure 19F:
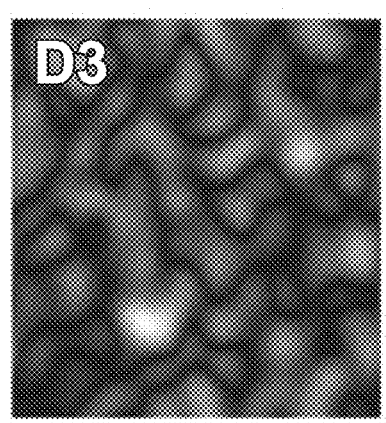
Figure 19G:
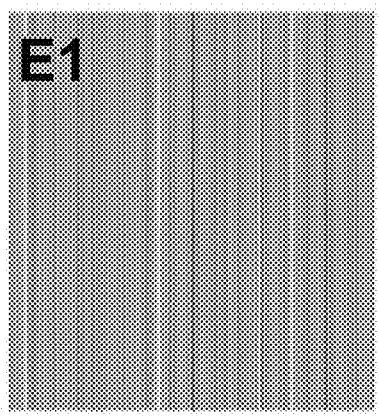
Figure 19H:
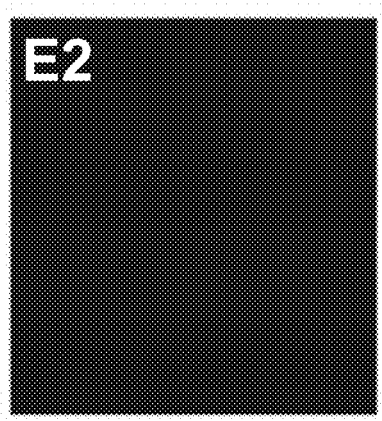
Figure 19I:
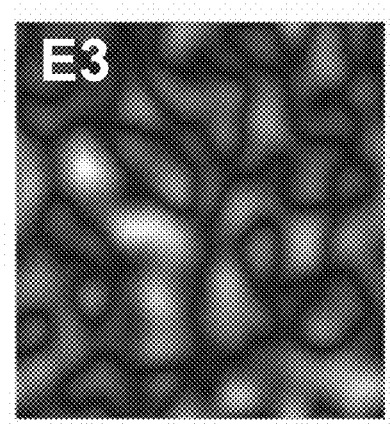

FIG. 19A represents an excitation point-spread function (PSF) while FIG. 19B represents a scattering PSF. FIG. 19C shows a representative modulation pattern. FIG. 19D illustrates a low-frequency object to be imaged and FIG. 19E illustrates the DC-subtracted image of the low-frequency object obtained with uniform illumination. FIG. 19F illustrates the DC-subtracted image of the low-frequency object with pattern modulated excitation. FIG. 19G illustrates a high-frequency object to be imaged and FIG. 19H illustrates the DC-subtracted image with uniform illumination. FIG. 19I illustrates the DC-subtracted image of the high-frequency object with pattern modulated excitation. The absence of signal in FIG. 19H shows that uniform illumination does not capture the spatial information of the object in FIG. 19G while the signal obtained in FIG. 19I shows that patterned illumination can capture this information.

Next, we write Equation 25 as a linear system. The convolution operation can be constructed as a matrix multiplication, where one of the inputs is converted into a Toeplitz matrix.

$$V_{\text{exPSF}*H_t} = C_{\text{exPSF}} V_{H_t} \quad [27]$$

Here, $C_{\text{exPSF}}$ is the equivalent 'convolutional matrix' of exPSF; $V_{H_t}$ is the column stacked version of $H_t$; $V_{\text{exPSF}*H_t}$ is the column stacked version 'exPSF*$H_t$'. Please note that $V_{H_t}$ and $V_{\text{exPSF}*H_t}$ are now $[N_y N_x \times 1]$ sized column vectors. Let, $D_{\text{exPSF}*H_t}$ be the diagonal matrix with the diagonal $V_{\text{exPSF}*i_t}$. Then the Equation 25 can be written as, $$V_{\acute{Y}_t} = C_{\text{sPSF}} D_{\text{exPSF}*i_t} V_X \quad [28]$$

Here, $C_{\text{sPSF}}$ is the equivalent 'convolutional matrix' of sPSF; $V_X$ is the column stacked version of X; $V_{\acute{Y}_t}$ is the column stacked version of $\acute{Y}_t$.

Similarly, the corresponding frequency domain form, i.e. Equation 26, can be written as, $$V_{\mathcal{F}\acute{Y}_t} = D_{\{(\mathcal{F}\text{exPSF} \circ \mathcal{F} H_t)^* \mathcal{F} X\}} V_{\mathcal{F}\text{sPSF}} \quad [29]$$

Expanding Equation 28 to include $N_t$ patterns gives, $$\begin{bmatrix} V_{\acute{Y}_1} \\ V_{\acute{Y}_2} \\ \vdots \\ V_{\acute{Y}_{N_t}} \end{bmatrix} = \begin{bmatrix} C_{\text{sPSF}} & 0 & 0 & 0 \\ 0 & C_{\text{sPSF}} & 0 & 0 \\ 0 & 0 & \ddots & 0 \\ 0 & 0 & 0 & C_{\text{sPSF}} \end{bmatrix} \begin{bmatrix} D_{\text{exPSF}*H_1} \\ D_{\text{exPSF}*H_2} \\ \vdots \\ D_{\text{exPSF}*H_{N_t}} \end{bmatrix} V_X \quad [30]$$

$$\begin{bmatrix} V_{\acute{Y}_1} \\ V_{\acute{Y}_2} \\ \vdots \\ V_{\acute{Y}_{N_t}} \end{bmatrix} = A_{\text{sPSF}} A_{\text{exPSF}*H} V_X$$

$$\begin{bmatrix} V_{\acute{Y}_1} \\ V_{\acute{Y}_2} \\ \vdots \\ V_{\acute{Y}_{N_t}} \end{bmatrix} = A_{\text{spatial}} V_X$$

Here, 0 is the all zero matrix of the same size as $C_{\text{sPSF}}$.

Similarly, the corresponding frequency domain form, i.e. Equation 29, can be written as, $$\begin{bmatrix} V_{\mathcal{F}\acute{Y}_1} \\ V_{\mathcal{F}\acute{Y}_2} \\ \vdots \\ V_{\mathcal{F}\acute{Y}_{N_t}} \end{bmatrix} = A_{\text{freq}} V_{\mathcal{F}\text{sPSF}} \quad [31]$$

Now, the Equations 30 and 31 are linear systems and can be used to solve for $V_X$ and $V_{\mathcal{F}\text{sPSF}}$ iteratively.

FIGS. 20A-20G show representative experimental results of DEEP-TFM imaging. A mixture of 4 μm and 10 μm beads was imaged through 2 mm of a scattering lipid solution (0.15%). Briefly, a mixture of 4 μm-sized and 10 μm-sized yellow-green fluorescent beads (FluoSpheres™ Sulfate Microspheres, 4.0 μm and FluoSpheres™ Polystyrene Microspheres, 10 μm, ThermoFisher Scientific, Mass., USA) was dropped in warm 1% agarose gel solution and stirred thoroughly. Then, 25 μl of the mixture was dropped in a pre-holed spacer (120 μm thick) onto a glass slide and a coverslip was placed on top of the spacer. The coverslip was sealed using clear nail varnish. The slide was left to cool down to solidify before image acquisition.

Figure 20A:
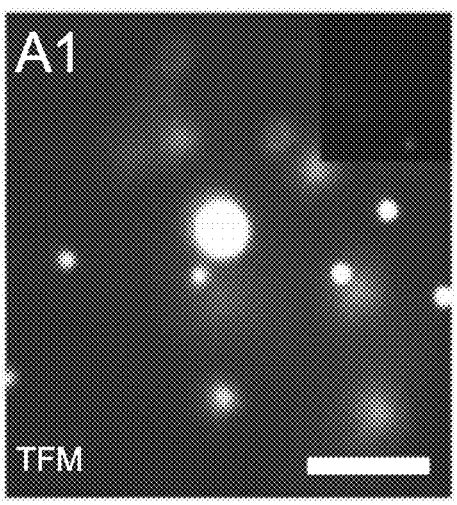
FIGS. 20A-20G illustrate comparative images obtained using systems and methods described herein and conventional systems.
Figure 20B:
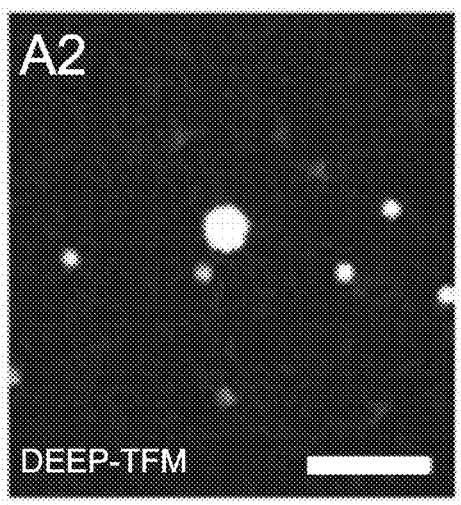

FIG. 20A shows a conventional TFM image; FIG. 20B shows the final DEEP-TFM image reconstructed with $N_t$=128 measurements. FIGS. 20A and 20B show the same field of view and the scale bars are 30 μm. Because light from all of the beads passes through the same thickness of the scattering medium, one would expect all 4 μm beads to show similar scattering behavior in FIG. 20A and in fact they do. Some beads simply are defocused in the TFM image as the thickness of the excitation plane of TFM is around 15 μm. However, in the DEEP-TFM image of FIG. 20B, many out-of-focus beads are not present in the image. Thus, in addition to de-scattering, DEEP-TFM also exhibits improved axial resolution over TFM.

Figure 20C:
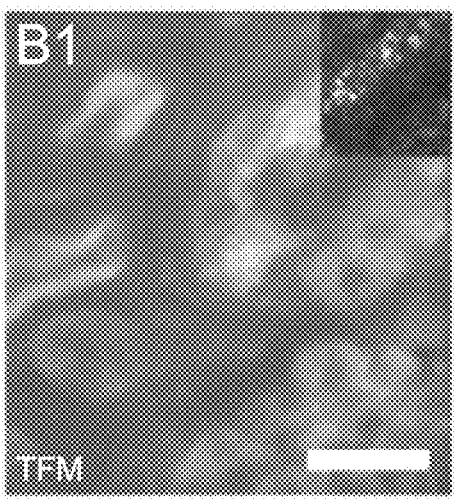
Figure 20D:
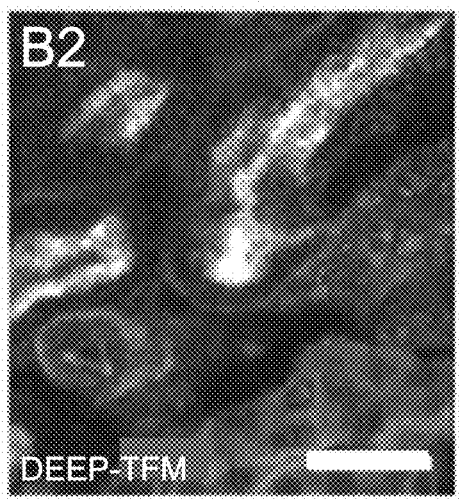

FIGS. 20C and 20D show images of the same field of view of a 16 μm thick mouse kidney section through 2 mm of a scattering lipid solution wherein FIG. 20C was obtained with TFM and FIG. 20D was obtained using DEEP-TFM. Scale bars are 30 μm. The prepared slide of sectioned mouse kidney (F24630, Invitrogen, Carlsbad, Calif., USA) contained a 16 μm cryostat section of mouse kidney stained with Alexa Fluor 488 wheat germ agglutinin, Alexa Fluor 568 phalloidin, and DAPI. A 0.15% lipid solution was used as the immersion medium to mimic the scattering environment since the sectioned mouse kidney is only 16 μm thick. The inset of FIG. 20C shows a representative image with patterned excitation (as raw data) before reconstruction. DEEP-TFM immediately improved image contrast and signal to background ratio (FIG. 20D).

Images were obtained of a 200 µm thick muscle tissue section stained for nucleus (blue channel, Hoechst 33342) and F-actin (red channel, Alexa Fluor 568 Phalloidin). The animal procedure (transcardial perfusion) was approved by the Massachusetts Institute of Technology Committee on Animal Care and meets the NIH guidelines for the care and use of vertebrate animals. Mice were deeply anesthetized with 1.25% avertin solution (350 mg/kg intraperitoneal) and transcardially perfused with phosphate buffered saline (PBS) containing 4% paraformaldehyde. After perfusion, thigh muscle was excised and post-fixed in 4% paraformaldehyde overnight. Muscle tissue was cryoprotected in 30% sucrose for 48 hours, embedded in Optical Cutting Temperature formulation (OCT, Tissue Tek), frozen at −20 degrees Celsius, and sliced at a thickness of 200 µm on a cryostat. Frozen sections were immersed in PBS for staining. Muscle slices were permeabilized in a solution of 1% Triton-X-100 in PBS for 20 minutes at room temperature with gentle shaking. Slices were then incubated in a working solution of the dyes (dissolved in PBS) for 20 minutes at room temperature with gentle shaking. Excess dye was removed by washing slices in PBS 3 times (6 minutes per wash, with gentle shaking at room temperature). Slices were then mounted on slides using Fluoromount-G or Vectashield as mounting media. Slides were coverslipped, and slides containing Vectashield as the mounting medium were sealed along the edges of the coverslip with clear nail polish. Slides were allowed to dry for at least 48 hours before imaging.

Figure 20E:
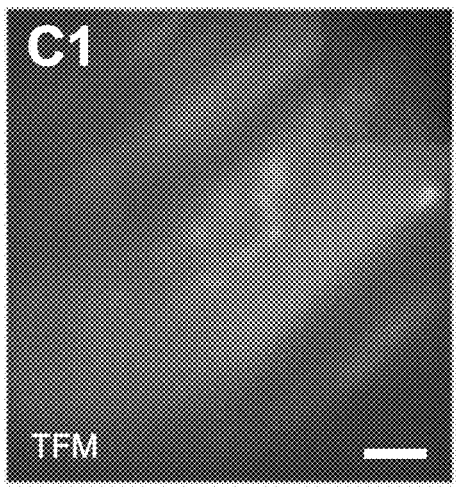
Figure 20F:
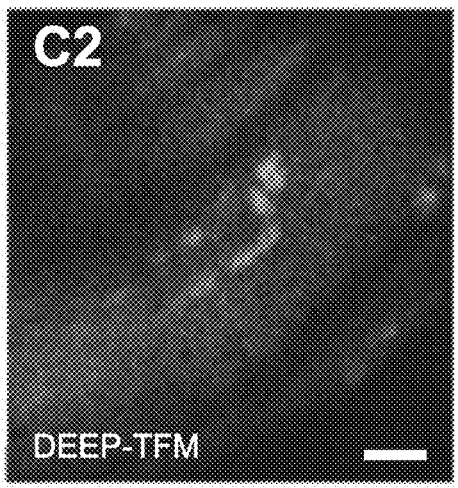
Figure 20G:
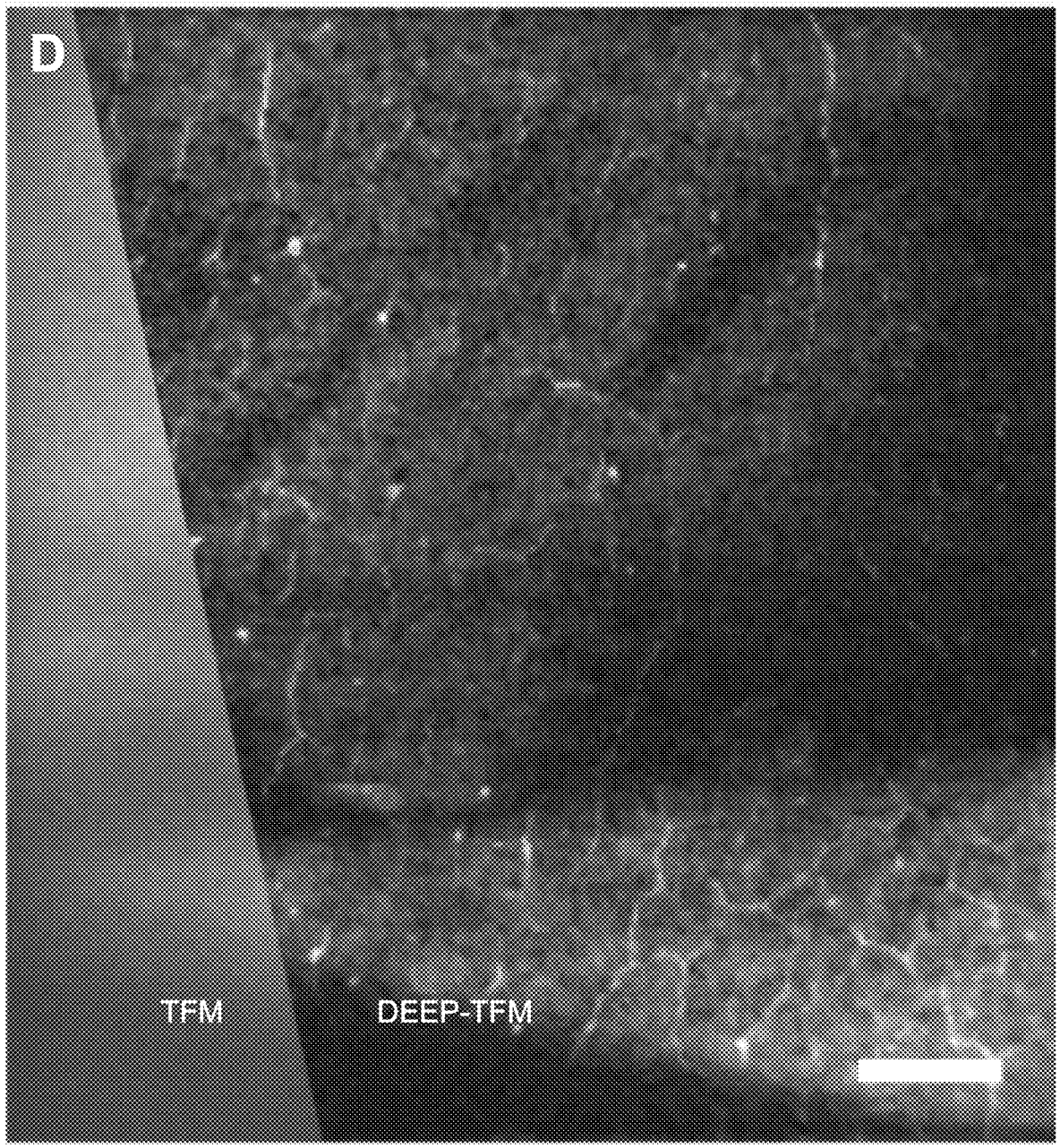

The FOV was nearly 150×150 µm² with 256×256 pixels. All DEEP-TFM reconstructions in FIGS. 20A-20F were performed with $N_t$=128 measurements. FIGS. 20E and 20F show representative TFM and DEEP-TFM images, respectively, of the same field of view from a 190 µm deep plane in the muscle tissue section. Scale bars are 20 µm. FIG. 20G shows a direct comparison of TFM and DEEP-TFM in the same F-actin image (at a 170 µm deep plane). As seen in FIGS. 20E-G, at deep imaging conditions, TFM loses a significant amount of high-frequency information as almost no high-resolution details are visible. Conversely, DEEP-TFM can reconstruct most fine details of the images.

Notably, DEEP-TFM and other systems and methods described herein are currently the only computational wide-field multiphoton imaging methods whose frame rate is independent of the size of the FOV. For example, millimeter-sized FOVs at diffraction limited resolution can be achieved with no sacrifice in speed. Systems and methods described herein uniquely provide flexible, depth-dependent imaging speeds wherein shallow imaging is almost single-shot while the deep imaging speed is depth-optimized. For instance, taken together, a speed-up of more than three orders of magnitude may be achieved over PSTPM for a volume of 256×256×156 px³ when the same acquisition time is used per measurement. In some embodiments, systems and methods described herein such as DEEP-TFM can employ modern compressive sensing theory with suitable image priors to achieve an additional ~10× speed up.

FIGS. 21A-21F illustrate simulated images obtained using conventional techniques and systems and methods described herein. The simulated two-photon image is of a whole neuron (256×256×156 voxels) in a live mouse. FIGS. 21A and 21B illustrate a top view (X-Y view) and a side view (X-Z view), respectively of a simulated image stack produced by a point scanning two-photon microscope (PSTPM). FIGS. 21C and 21D illustrate a top view (X-Y view) and a side view (X-Z view), respectively of a simulated image stack produced by a wide-field temporally focused two-photon microscope (TFM). FIGS. 21E and 21F illustrate a top view (X-Y view) and a side view (X-Z view), respectively of a simulated image stack produced by the system 300 (DEEP-TFM). The shaded plots in FIGS. 21B, 21D, and 21F show the number of measurements needed at each z-plane. PSTPM requires over 10 million measurements (i.e., one for each voxel). TFM requires only 156 measurements (i.e., one for each depth), but the image quality degrades as the imaging depth is increased. DEEP-TFM requires 8488 measurements but maintains similar image quality as PSTPM.

Femtosecond laser pulses with high pulse energy (~µJ–mJ) as used in TFM is what enables wide-field excitation. Depth resolution is achieved by controlling optical dispersion so that the pulse width rapidly broadens away from the focal plane resulting in low two-photon excitation efficiency out of plane. However, emitted photons, due their shorter wavelengths than excitation photos, are strongly scattered by the tissue. As a result of wide-field detection with an area detector, some scattered emission photons in TFM are assigned to incorrect pixels on the detector resulting in resolution degradation and signal-to-noise ratio reduction. As illustrated in FIGS. 21C and 21D, TFM images at shallower image planes include a background haze. As the imaging depth is increased, TFM images lose high-resolution information as discussed above in relation to FIGS. 19A-19I. By using arbitrary pattern projection or other patterning techniques described herein with respect to system 200 and system 300, background noise (haze) and loss of spatial information is sharply reduced.

Figure 22:
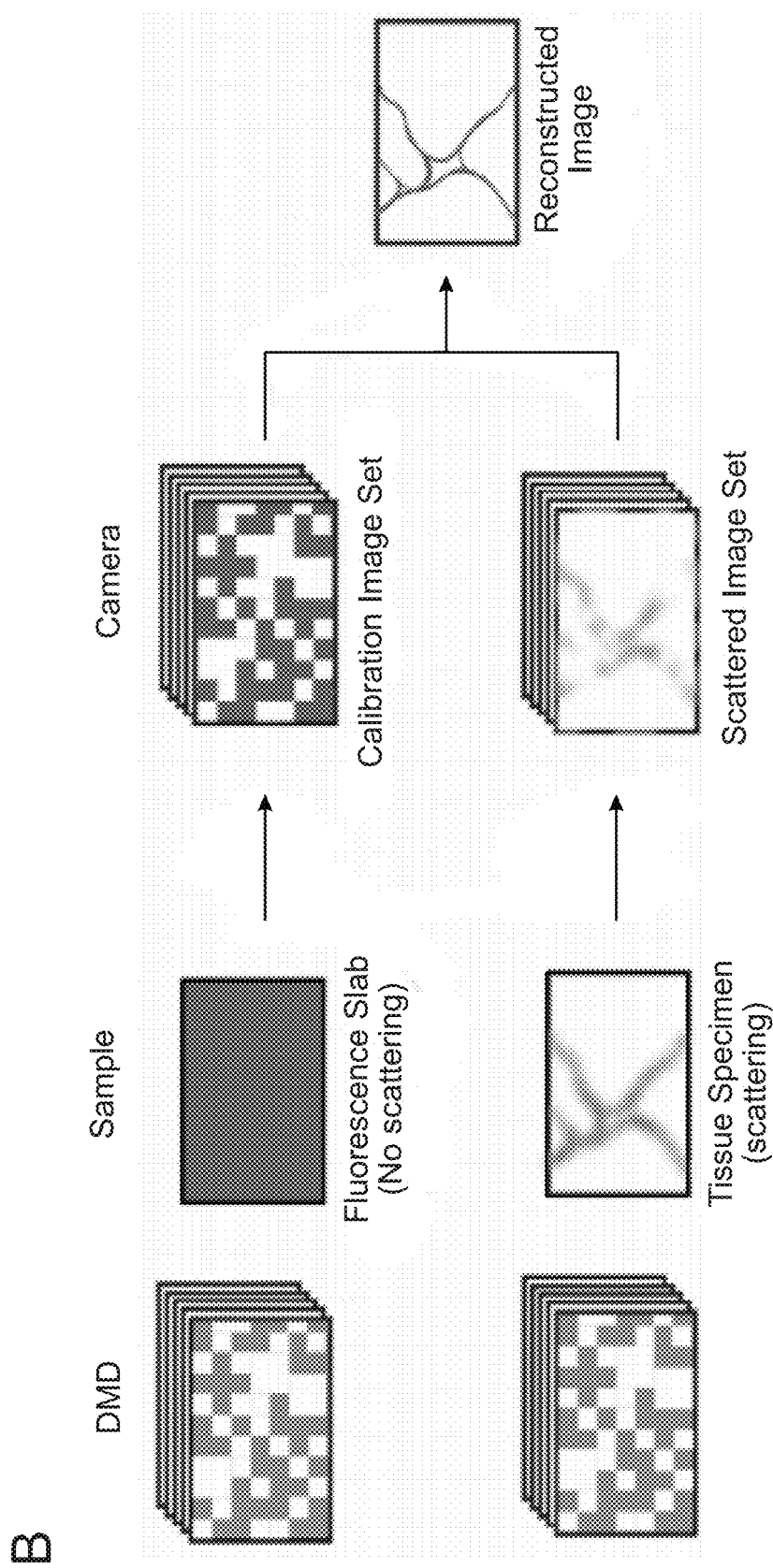
FIG. 22 illustrates a workflow for reconstructing de-scattered images using systems and methods as described herein.

FIG. 22 illustrates a workflow for obtaining reconstructed images in accordance with various embodiments described herein. First a set of patterns are projected onto a calibration specimen (e.g., a homogeneous thin fluorescent layer) to record the calibration image set at the absence of any scattering. Then, the same patterns are projected onto the sample plane 301 to record encoded images of the sample. Finally, de-scattered images can be reconstructed.

In some embodiments, calibration samples can be used to provide a baseline against which sample images can be compared. For example, a thin quantum dot layer can be used for the calibration of patterns for green (535 nm) and red channels (605 nm). A thin, fluorescent layer of green quantum dots (supplied by QDVision, Lexington, Mass., USA) dispersed in hexane (10 µL) are dropped onto a coverslip (thickness 170 µm) and allowed to dry. The coverslip is affixed to a glass slide and sealed by transparent nail varnish. Similarly, a thin DAPI solution layer can be used for the calibration of patterns for the blue channel (460 nm). Saturated DAPI solution in 1:1 mixture of deionized water and DMSO is dropped in a pre-holed spacer (120 µm thick, Secure-Seal Imaging Spacers, Grace Bio-Labs, OR, USA) onto a glass slide and a coverslip was placed on top of the spacer. The coverslip sealed using clear nail varnish.

A calibration process in accordance with embodiments described herein can give the ensemble of patterns, $\{\tilde{H}_t\}$, used to modulate the spatial features. The imaging experiment gives, the ensemble of measurement images, $\{Y_t\}$. Then the reconstruction of the de-scattered image, X, is possible from solving the set of Equation 18 equations (or the set of Equation 19 equations) as described above. However, the constituting set of equations in Equation 18 (and its corresponding frequency domain form in Equation 19) are not linear but rather quadratic with respect to the unknowns (X and sPSF). To solve this system, one could first assume a form for sPSF and then Equation 18 becomes a linear system that can be solved for X with commonly available linear-optimization methods. When a solution for X is found that can be substituted in Equation 19, a similar linear system is created that can be solved for $\mathcal{F}$ sPSF (and hence for sPSF). Thus, a proper solution for X can be iteratively found. In some embodiments, only one iteration is performed assuming a canonical form for sPSF. This can result in visually accurate reconstructions. Some embodiments can employ a two-step iterative shrinkage/thresholding algorithm (TwIST) to solve the above linear equations.

In some embodiments, the systems 200, 300 can employ line-scanning and structured illumination (SI) techniques to increase spatial resolution and obtain axial sectioning capability. SI can increase lateral resolution or even achieve super-resolution in some instances. SI encodes sample information, shifting high frequency information, which is outside of numerical aperture originally, back to the range within the numerical aperture by using multiple intermediate images to reconstruct the final image. SI combined with temporal focusing can improve the axial sectioning capability of widefield and line-scanning two-photon microscopy in some embodiments. In some examples, SI can be modulated on the conjugate imaging plane or Fourier plane. For example, the digital mirror device 315 (DMD) placed at the conjugate imaging plane can work as a grating in the system 200, 300 while generating SI at the same time. A spatial light modulator (SLM) 210 placed at the conjugate Fourier plane can generate SI by holographic phase patterning.

Figure 24:
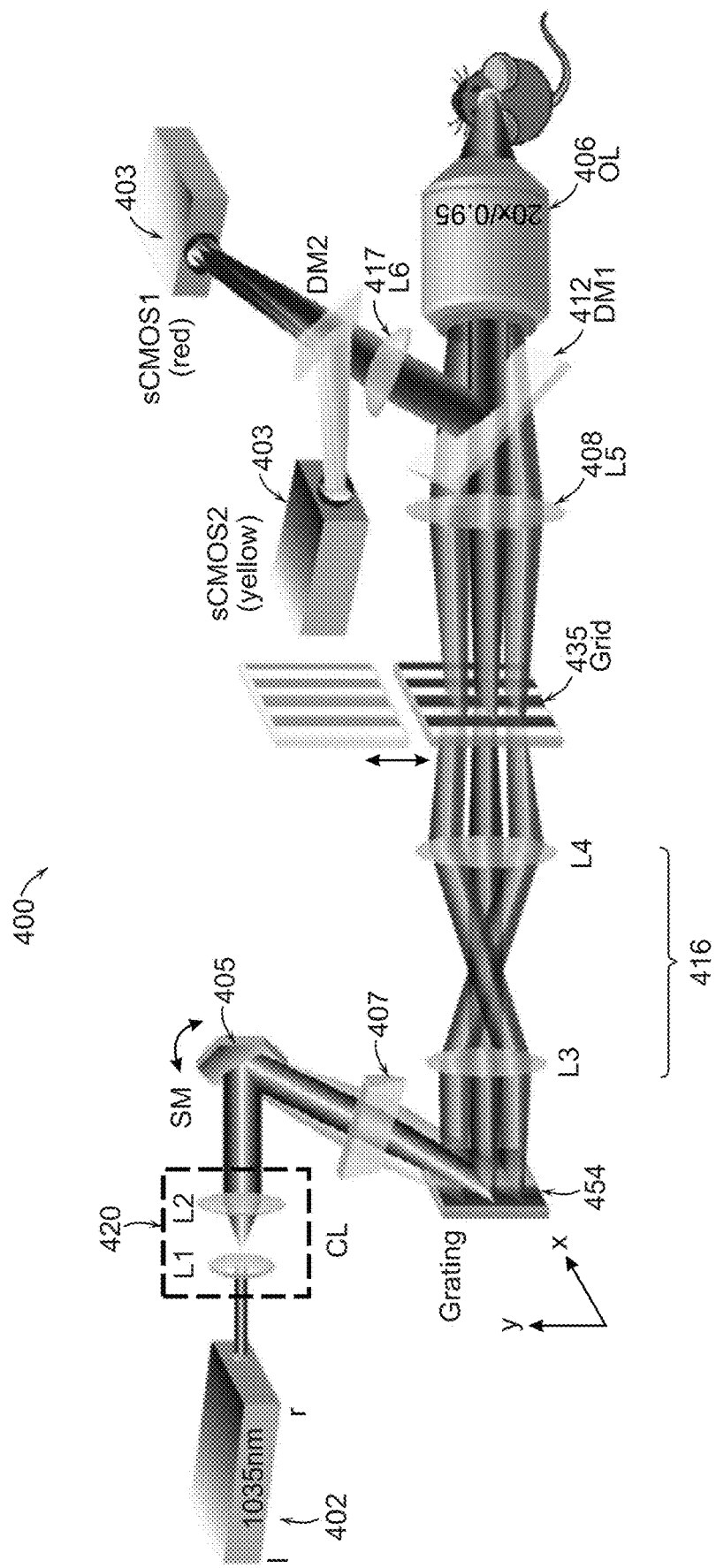
FIG. 24 illustrates a schematic of a HiLo line-scanning temporal focusing microscopy (HiLL) system in accordance with various embodiments described herein.

In accordance with various embodiments described herein, HILo-Line-scanning temporal focusing microscopy (HiLL) can be used to obtain images with better resolution and contrast and improved axial sectioning capability. A HiLL system 400 is illustrated in FIG. 24. The HiLo technique can be used to provide depth resolution in widefield microscopy. In the HiLo technique, the system 400 takes sequential images of the object using uniform illumination (UI) and structured illumination (SI). The SI image, after low pass filtering, retains only in-focus low spatial frequency components. The UI image, after high pass filtering, retains only in-focus high spatial frequency components. Appropriate merging of information from both images produces the correct depth resolved image from the focal plane.

The HiLL system 400 is similar to the systems 200, 300 described previously with respect to FIGS. 2A-2B and 5A-5B with the addition of an ability to switch between uniform illumination of the object and structured illumination of the object. The HiLL system 400 includes beam shaping optics 420, an excitation source 402, a scanning mirror 405, a cylindrical lens 407, a grating 454, relay lenses 416, and a grid 435, a dichroic mirror 412, and an objective 406.

The excitation source 402 can be a laser in some embodiments. The laser can generate femtosecond pulses at a wavelength of 1035 nm (repetition rate 1 MHz, spectrum width ±5 nm), for example, the Monaco laser (Coherent Inc., CA, USA). The scanning mirror 405 (6350, Cambridge Technology, MA, USA) mechanically scans the beam along the y-axis. The cylindrical lens 407 (f=150 mm) focuses the beam into a line on the grating 454 (20RG1200-1000-2, Newport Co., CA, USA, 1200 grooves/mm). The incident angle $\theta_i$ is about 73°, so the $1^{st}$ order diffraction angle is about 16°. The grating generates dispersion along the x-axis. The relay lenses 416 can include a first lens with focal length f=300 mm and a second lens with focal length f=75 mm.

To generate structured illumination, a grid 435 is placed on the conjugate image plane. In some embodiments, the grid 435 can be a Ronchi ruling (38-258, Edmund Optics, NJ, USA). In some embodiments, the grid 435 can be mounted on a magnetic mounting seat so that the grid 435 can be manually removed to enable uniform illumination. In some embodiments, the time to remove the grid 435 from the magnetic mounting seat can be negligible compared to the imaging time (e.g., 1.6 s per frame). The contrast of the stripes in the grid 435 is important for the HiLo process. Thus, a grid 435 can be chosen having 10 line-pair/mm, which is equivalent to a period of 2.88 μm on the image plane. This period is larger than the PSF.

The system 400 can include a tube lens 408. The focal length of the tube lens can be 300 mm in some embodiments. In the back aperture, the beam size is about 20×20 mm. The system 400 can overfill the back aperture so that the spatial resolution of HiLL microscopy is comparable with TPLSM. The FOV is about 250×250 μm² in some embodiments. A second tube lens 417 can be included in the detection path. The focal length of the tube lens 417 can be f=350 mm. The system magnification can be about 40× based upon the objective magnification and the focal length of tube lenses. The image can be detected at an imaging device 403. In some embodiments, two imaging devices 403 can be employed simultaneously to work as, for example, red channel and yellow channel. In some embodiments, the imaging device 403 can be a two-dimensional pixelated imaging device such as a charge-coupled device (CCD) or complementary metal-oxide-semiconductor (CMOS) pixelated imaging device. In some embodiments, the imaging device 403 can acquire images at a sufficient speed to acquire an image for each excitation pattern.

The axial confinement of LineTFM is the same as that of TPLSM. Thus, it can be described as $$TPE(z) \approx \frac{1}{1+(\Delta z/z_R)^2} \qquad [32]$$

where $Z_R$ represents the Rayleigh range of the beam and $\Delta z$ refers to the displacement from the focus. The FWHM of TPE(z) defines the axial resolution of LineTFM. Structured illumination in HiLL can improve axial sectioning and reduce scattering. We calculated the SI intensity change along the z-axis according to the properties of a defocused optical system. In incoherent detection, the optical transfer function (OTF) of the system represents the contrast of stripes on the image plane by scanning a thin sheet of fluorescence along the z-axis. We measured the spatial frequency in the image plane $T_g$=2.88 which is converted to normalized SI frequency s=$\lambda$/($T_g$·NA)=0.378. The OTF along z-axis is $$T_A(z) = A \frac{2J_1\left[k \sin^2 \alpha s\left(1-\frac{s}{2}\right)z\right]}{k \sin^2 \alpha s\left(1-\frac{s}{2}\right)z} \qquad [33]$$

Where A is the amplitude correction related to SI frequency s, and k is the wave vector. The SI pattern on the focal plane can be described as sinusoidal function. Both the lateral and axial periods of stripes are larger than the PSF of LineTFM. Because LineTFM overfills the back aperture of the objective, the resolution of HiLL is the same as LineTFM in our experiments. For a widefield temporal focusing system, if the axial width of the stripes is larger than the PSF of LineTFM generated by a higher frequency grid, the axial resolution of HiLL could be further improved but the contrast of the stripes would be lower.

The key of the HiLo technique is that SI only modulates objects that are in focus but not objects that are out of focus. The image acquired under uniform illumination is $$U(x)=I_{in}(x)+I_{out}(x) \quad [34]$$

where $I_{in}$ and $I_{out}$ are photons in focus and out of focus, respectively. The images acquired under sinusoidal SI are represented as $$S(x)=A[I_{in}(x)(1+M\cos(k_g x))+I_{out}(x)], k_g=2\pi/T_g \quad [35]$$

Because $I_{out}$ is not modulated, we can remove $I_{out}$ by subtracting Equation 35 from Equation 34, that is, $$D(x) = \left| U(x) - \frac{1}{A}S(x) \right| = I_{in}(x)(1 + M\cos(k_g x)) \quad [36]$$

This product is a low resolution version of $I_{in}$. A low-pass (LP) filter can be applied to $D(x)$ on the Fourier plane, e.g., a Gaussian filter. Different filters can slightly influence the reconstructed image contrast. The cutoff frequency $k_c$ is smaller than $1/T_g$; normally we choose half of the modulation frequency. So the low-passed image is $$I_{LP}(x) = \mathcal{F}^{-1}\{\mathcal{F}\{D(x)\} \times LP(k_x)\} \quad [37]$$

To recover the high resolution part of $I_{in}$, a high-pass (HP) filter can be applied to $U(x)$, because a single structured illumination image lost information smaller than the fringes. The HP filter satisfies $HP(k_x)=1-LP(k_x)$. The high-passed image is $$I_{HP}(x) = \mathcal{F}^{-1}\{\mathcal{F}\{U(x)\} \times HP(k_x)\} \quad [38]$$

The reconstructed image is a combination of $I_{LP}$ and $I_{HP}$:

$$I_{HiLo}(x)=\eta I_{LP}(x)+I_{HP}(x) \quad [39]$$

where $\eta$ adjusts the relative intensity of the two images to combine them seamlessly.

Figure 25:
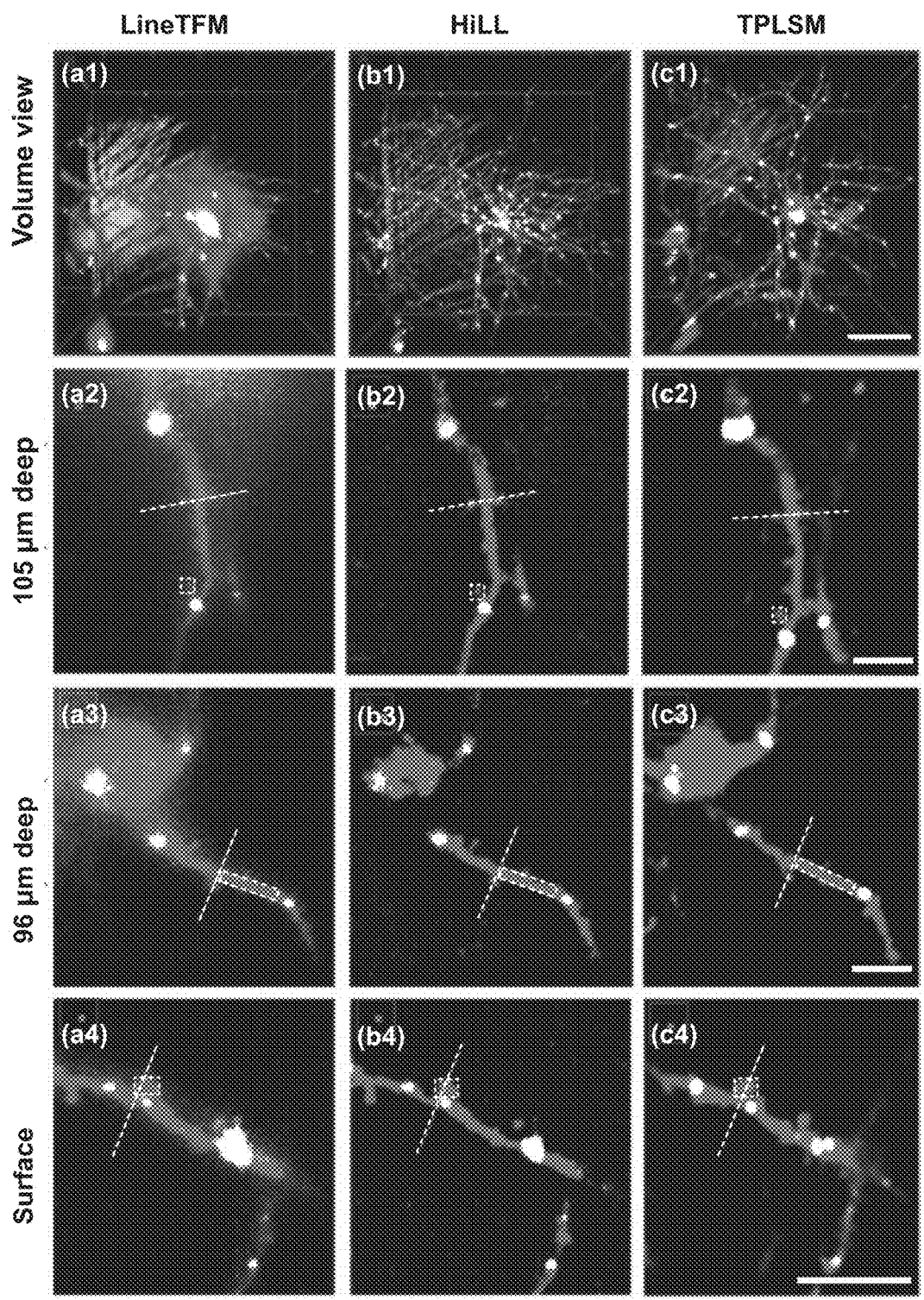
FIG. 25 illustrates images of mice of mScarlet-I cell fill and venus-gephyrin labeled inhibitory synapses using LineTFM, HiLL and TPLSM.

FIG. 25 illustrates images of mice of mScarlet-I cell fill and venus-gephyrin labeled inhibitory synapses using LineTFM, HiLL and TPLSM. The figure shows a comparison of the same cell imaged by these three methods. Here, TPLSM works as a ground truth to evaluate HiLL microscopy. For in vivo imaging, bright objects contribute more to the scattered photons compared to dim objects. The scattered photons add to background intensity that lowers the contrast of the image. The HiLo technique has more obvious effect on contiguously labeled objects (e.g., the mScarlet-I cell fill) than on sparsely distributed ones (e.g., venus puncta). Comparing FIGS. 25(a1) and (b1), it is notable that HiLL efficiently removes the scattered photons from soma and bright dendrites without depleting fine structures such as spines. In other words, spines are more visible in HiLL while they are blurry in the homogeneously illuminated image. However, venus-gephyrin labeled inhibitory synapses are nearly identical in HiLL and LineTFM. Unlike the mScarlet-I cell fill, inhibitory synapses distribute sparsely, and the size of each synapse is small. Thus, the number of scattered photons in the venus-gephyrin channel is comparably less; the scattered photons rarely cover adjacent labels. HiLL has less influence on image contrast for sparsely distributed objects.

Dendritic branches are also illustrated at different depths. FIG. 25 shows the magnified images of the results, from 100 µm deep (a2-c2, a3-c3) to surface (a4-c4). The photons originating deep inside the tissue suffer from scattering; thus, the contrast is lower for deeper structures than for structures near the surface. HiLL has a more obvious effect on structures deep inside tissue than on superficial structures.

Figure 26:
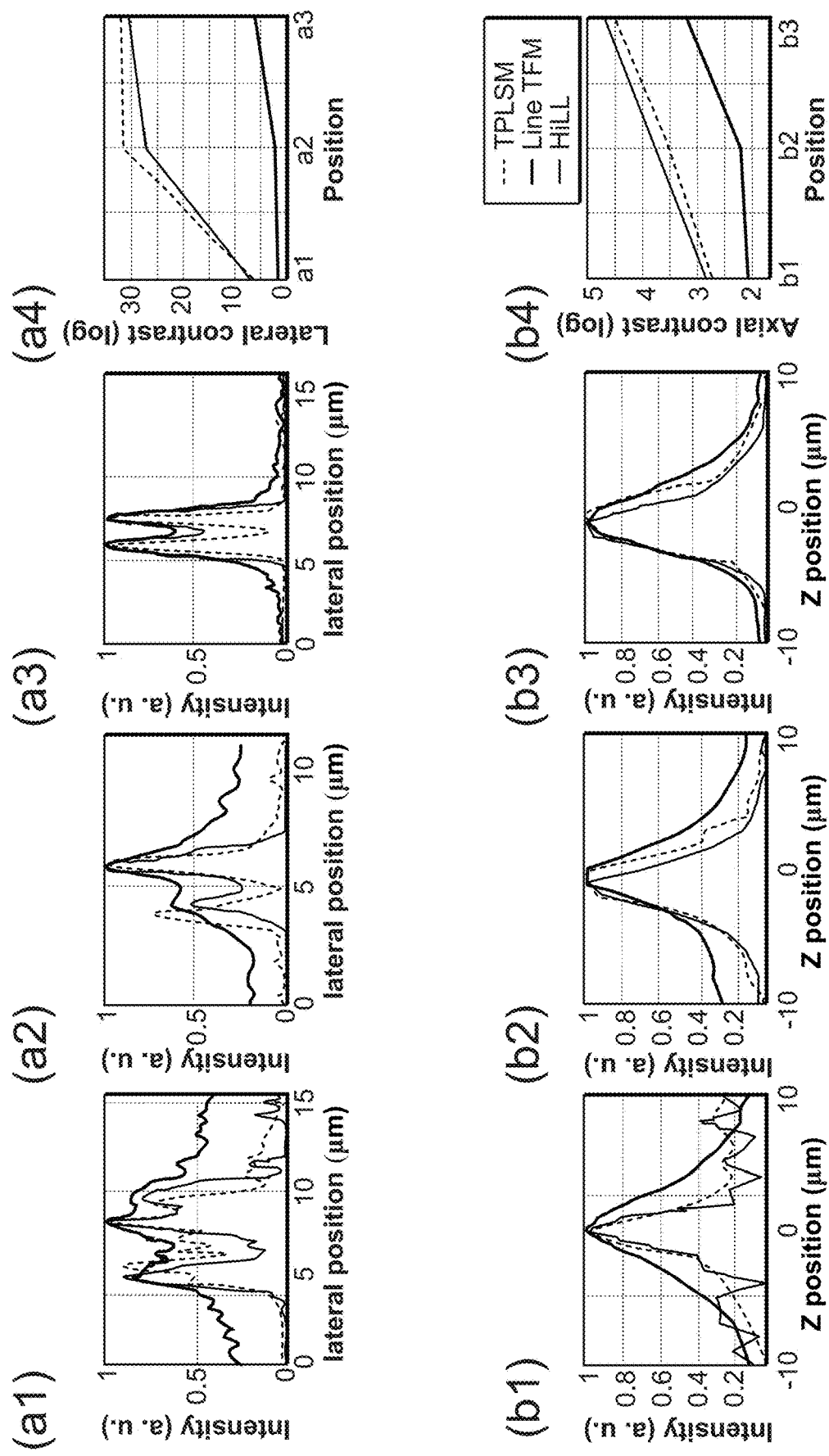
FIG. 26 shows the intensity profiles for cross dendrites and spines identified in FIG. 25.

The image stack in FIG. 25 is further quantitatively analyzed to specifically evaluate contrast. FIG. 26 shows the normalized intensity profiles of the regions marked by white dashed lines in FIG. 25. HiLL reduces the scattering effect in both lateral and axial directions. As a consequence, small objects are more distinguishable in HiLL, which is nearly the same as TPLSM, than LineTFM. For example, FIG. 26 shows the intensity profiles for cross dendrites and spines. HiLL and TPLSM can identify the spines clearly, while LineTFM cannot. In addition, the effect of reducing scattering is more obvious in deep tissue (a1-2, b1-2) than on the surface (a3, b3) because photon scattering is more severe in deeper tissue. The contrast improvement of HiLL is shown in a4 and b4. The contrast is calculated according to $C=I_{max}/I_{min}$, where $I_{max}$ is the maximum intensity in the intensity profile, and $I_{min}$ is the minimum non-zero intensity in the intensity profile. Because $I_{min}$ is very small in HiLL and TPLSM, C is plotted on a log scale. HiLL has similar contrast with TPLSM in both lateral and axial directions. Thus, HiLL significantly improves contrast compared to LineTFM, especially near soma and bright dendrites.

Generating structured illumination is an important step in HiLL. The structured illumination can be generated using the grid 435 (e.g., a Ronchi ruling) in the conjugate image plane. Manual removal of the Ronchi ruling can be performed after finishing the structured illumination image stack. The manual method works well when the sample does not change during the imaging time (e.g., about 90 s for one image stack in some embodiments). In some embodiments described herein, the grid 435 can be associated with a motor controlled mount to enable the grid 435 to in and out of position in the optical path for each frame acquisition (e.g., about 1.6 s exposure time per frame in some embodiments).

HiLL can image the same sample much faster than TPLSM with similar signal to background noise and resolution. The imaging speed of HiLL is compared with TPLSM under the same pulse energy and the number of pulses of a diffracted limited spot. To visualize weak fluorescent structures, such as dendrites and spines, the imaging average power and exposure time can be selected to achieve sufficient SNR from weak fluorescent structures inside the sample while staying below the power threshold of two-photon excitation saturation.

An example of the speed-up obtainable using HiLL is described here. The excitation source of TPLSM is a Ti:Sapphire femtosecond laser. The average power out of the objective is about 40 mW, repetition rate is 80 MHz, and the dwell time of each pixel is 40 µs. The dwell time is longer than usual because the sample is dim. Thus, the maximum pulse energy for fluorophore such as most fluorescent proteins is about 40 mW/80 MHz=0.5 nJ without fluorescence saturation. The number of pulses is 40 µs×80 MHz=3200. The step size is 250 nm/pixel. A 256×256 µm² field of view (FOV) requires about 1000×1000 pixels. So, the imaging time of one frame is 40×1000×1000=40 s.

The radial resolution of LineTFM is about 0.5 µm, and the FOV is about 250×250 µm². The sampling rate of each diffracted spot is 3 pixels. Thus, LineTFM parallelizes N=250/0.5=500 diffracted limited spots in a single line. Pulse energy per line equals to 0.5 nJ×500=250 nJ. The repetition rate of the laser is 1 MHz, so the average power per line is $p_o$=250 nJ×1 MHz=250 mW. For the same number of pulses, the dwell time of a single line is 3200/1

MHz=3.2 ms. The scanning direction also has 500 diffracted limited spots, so the frame exposure time is 3.2 ms×500=1.6 s. We need to get one stack with uniform illumination and another stack with structured illumination, so the imaging time of HiLL is 3.2 s. Compared to the frame rate of TPLSM, HiLL is about 40/3.2=12.5 times faster.

Figure 27:
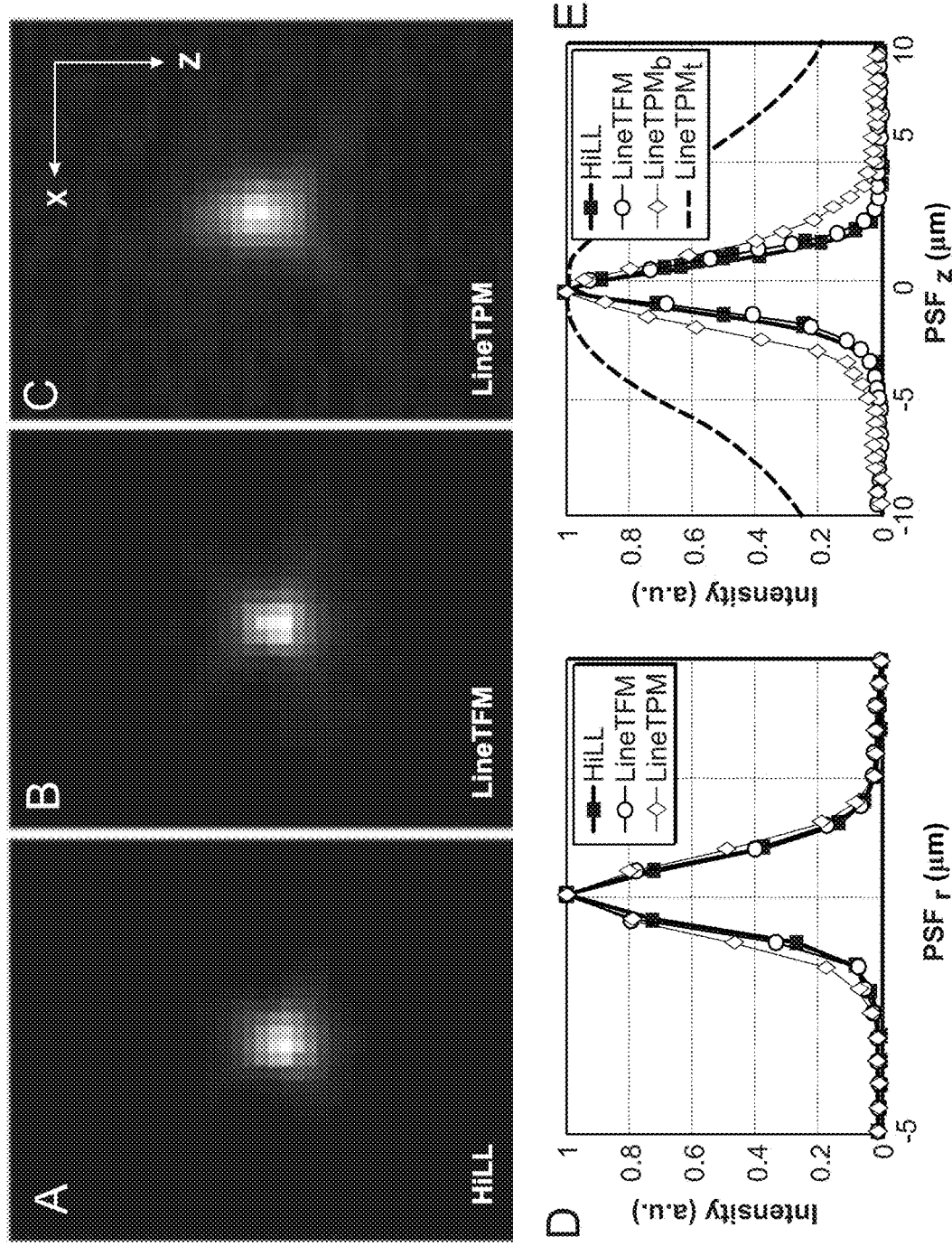
FIG. 27 illustrates the PSF for HiLL, LineTFM and line-scanning two photon microscopy (LineTPM) systems.

The PSF of HiLL, LineTFM and line-scanning two photon microscopy (LineTPM) are measured, respectively, using 200 nm red fluorescent beads (Carboxylate-modified Microspheres, red fluorescent (580/605), ThermoFisher Scientific, MA, USA). The results are illustrated in FIG. 27. The PSF of HiLL is calculated according to Equations 37-39 after acquiring image stacks of these beads under uniform illuminated LineTFM and structured illuminated LineTFM, respectively. The radial resolution is about 0.65 µm and the axial resolution is about 2.56 µm. Both radial and longitudinal FWHM of the PSF are nearly the same with and without HiLo processing. Both HiLL and LineTFM PSF have smaller FWHM than the PSF of LineTPM, because temporal focusing overfills the back aperture rather than only a line on the back aperture in LineTPM. Optical sectioning ability is measured by axially scanning a thin fluorescence layer (single layer of the same fluorescent beads), which shows LineTPM has poor optical sectioning ability (Panel E, black dashed line). The experimental results are consistent with the theoretical calculation above.

The lenses and gratings can be selected to achieve a sufficiently large FOV and overfill the back aperture at the same time. The beam shaping optics 420 can collimate the beam and expand it to the size of $x_o$. After that, along the x-axis, the beam is collimated until the grating 454 adds dispersion to it. The incident angle to the grating 454 is $\theta_i$. Along y-axis, the beam is focused by cylindrical lens 407, and the grating 454 is on the focal plane of the cylindrical lens 407. The beam size at back aperture and FOV are calculated using matrix methods.

After the grating 454, the input beam is $[x_{in}, \alpha_{in}]'$, where $$x_{in} = x_o/\cos\theta_i, \alpha_{in} = \frac{d\lambda}{d\cos\theta}.$$

d$\lambda$ is the spectrum width of laser, which is 10 nm here. d is the groove spacing of the grating 454, which is 1/1200 mm. $\theta$ is the diffraction angle of the grating, which is related to the incident angle by $\sin\theta_i + \sin\theta = m\lambda/d$, where m=1 for the 1$^{st}$ order diffraction.

Then the lens matrix is $$\begin{bmatrix} 1 & 0 \\ 1/f_j & 1 \end{bmatrix},$$

and the propagation matrix is $$\begin{bmatrix} 1 & f_j \\ 0 & 1 \end{bmatrix}, j = 3, 4, 5.$$

In our setup, $f_3$=300 mm, $f_4$=75 mm, $f_5$=300 mm. Thus, the size of beam along x-axis on the back aperture is:

$$\begin{bmatrix} x_{BA} \\ \alpha_{BA} \end{bmatrix} = \begin{bmatrix} 1 & f_5 \\ 0 & 1 \end{bmatrix}\begin{bmatrix} 1 & 0 \\ -1/f_5 & 1 \end{bmatrix}\begin{bmatrix} 1 & f_5+f_4 \\ 0 & 1 \end{bmatrix}\begin{bmatrix} 1 & 0 \\ -1/f_4 & 1 \end{bmatrix}\begin{bmatrix} 1 & f_3+f_4 \\ 0 & 1 \end{bmatrix} \quad (40)$$

$$\begin{bmatrix} 1 & 0 \\ -1/f_3 & 1 \end{bmatrix}\begin{bmatrix} 1 & f_3 \\ 0 & 1 \end{bmatrix}\begin{bmatrix} x_{in} \\ \alpha_{in} \end{bmatrix}$$

$x_{BA} \approx 20$ mm. For y-axis, $$y_{BA} = \frac{f_3}{f_{CL}} \cdot \frac{f_5}{f_4} \cdot y_{in}. \quad (41)$$

To match with x-direction beam size, we choose the focal length of the cylindrical lens 417 to be 150 mm, then $y_{BA}$ is about 20 mm on the back aperture. Both directions overfill the back aperture. The objective 406 can be a 20× objective (0.95NA from Olympus) in some embodiments, so the FOV is:

$$\begin{bmatrix} x_{FOV} \\ \alpha_{FOV} \end{bmatrix} = \begin{bmatrix} 1 & f_{ob} \\ 0 & 1 \end{bmatrix}\begin{bmatrix} 1 & 0 \\ -1/f_{ob} & 1 \end{bmatrix}\begin{bmatrix} 1 & f_{ob} \\ 0 & 1 \end{bmatrix}\begin{bmatrix} x_{BA} \\ \alpha_{BA} \end{bmatrix}, \quad (42)$$

which is about 250 µm. $y_{FOV}$ can be easily adjusted by changing the voltage on the scanning mirror 405. We choose the focal length of tube lens 417 to be 350 mm according to the pixel size of the imaging device 303 to fulfill the Nyquist theorem.

FIG. 28 illustrates a flowchart for a method 2800 of performing HiLo line scanning temporal focusing microscopy according to various embodiments described herein. The method includes illuminating a sample with one or more spatially and temporally focused line beams of light to cause light emission or light scattering from a plane at a selected depth at least more than one scattering length deep (preferably greater than two scattering lengths deep) within the sample (step 2802). The method includes acquiring a first image including scattered or emitted light from the sample illuminated by the one or more scanning beams (step 2804). The method includes Encode the one or more spatially and temporally focused line beams with structured illumination by passing the one or more line beams through a grid or arbitrary pattern generator (step 2806).

The method includes illuminating the sample with the one or more spatially and temporally focused line beams of light including encoded structured illumination to cause light emission or scattering from the plane at the selected depth within the sample (step 2808). The method includes acquiring a second image including scattered or emitted light from the sample illuminated by the one or more line beams including encoded structured illumination (step 2810). The method includes extracting low spatial frequency information from the first image and high spatial frequency information from the second image (step 2812). The method includes combining at least the low spatial frequency information and the high spatial frequency information to reconstruct at least multiphoton image data related to the object at the selected depth (step 2814). The method includes assemble a plurality of reconstructed images acquired from different illumination angles to provide a reconstructed image having an isotropic lateral point spread function (step 2816).

While the present inventive concepts have been described with reference to particular embodiments, those of ordinary skill in the art will appreciate that various substitutions and/or other alterations may be made to the embodiments without departing from the spirit of the present inventive concepts. Accordingly, the foregoing description is meant to be exemplary and does not limit the scope of the present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A multi-photon temporal focusing microscopy system, comprising:
    a light source that generates multi-photon excitation light;
    a sample illumination system that couples the multi-photon excitation light onto a sample wherein one or more selected structured illumination patterns of the multi-photon excitation light is delivered onto the sample to induce fluorescence in patterned regions of the sample;
    a computing system having a processor, wherein the computing system communicates the one or more selected structured illumination patterns to the sample illumination system to illuminate the sample with the one or more structured illumination patterns;
    an imaging device having a plurality of light detection elements that receives light from the sample at the plurality of detection elements of the imaging device to form a plurality of intermediate images of the sample corresponding to each of the one or more selected structured illumination patterns; and
    wherein the computing system generates a reconstructed image of the sample by performing a processing operation on the plurality of detected intermediate images of the sample corresponding to each of the one or more selected illumination patterns.

2. The system of claim 1 further comprising an array of controlled mirror elements configured to scan a line of illumination onto the sample.

3. The system of claim 1 further comprising a multiline illumination device that couples a plurality of scanning lines onto the sample.

4. The system of claim 1 wherein the imaging device comprises a two dimensional pixelated imaging device having at least 400,000 pixels.

5. The system of claim 1 wherein the computing system comprises one or more processors, at least one processor being configured to process the plurality of intermediate images and generate the reconstructed image and wherein the computing system generates the reconstructed image by altering a spatial frequency to provide a plurality of selected structured illumination patterns using a selected pixel group.

6. The system of claim 5 wherein a detected intermediate image is expressed as a Poisson distribution of a scattering function.

7. The system of claim 1 wherein the light source comprises a pulsed laser that generates a two-photon excitation emission, or a three-photon excitation emission, that is coupled to the sample.

8. The system of claim 1 further comprising a spatial light modulator, or a digital micromirror device, that generates a temporally focused structured illumination pattern.

9. The system of claim 1 further comprising an objective lens, the sample and the objective lens undergoing relative movement to select an imaging depth in the sample.

10. The system of claim 1 further comprising a rotation element that rotates an illumination beam relative to the sample and optionally wherein the rotation element comprises a dove prism.

11. The system of claim 1 further comprising a grating or a diffractive optical element.

12. The system of claim 1 wherein the one or more selected structured illumination patterns further comprises a plurality of preset structured illumination patterns stored in a memory and wherein the imaging device comprises a charge-coupled device (CCD), a complementary metal-oxide semiconductor (CMOS) imager, or a multi-anode photomultiplier (PMT) array.

13. The system of claim 1 wherein the computing system comprises a memory having stored on a non-volatile computer readable medium a reconstruction algorithm using a plurality of preset structured illumination patterns and wherein the reconstruction algorithm further comprises adjusting a pixel group size of the imaging device as a function of imaging plane depth in the sample.

14. A method for multi-photon temporal focusing microscopy, comprising:
    illuminating a sample using a structured illumination system that couples a plurality of structured multi-photon illumination patterns onto the sample to induce fluorescence in the sample;
    detecting a plurality of intermediate images of the sample with an imaging device having a plurality of light detection elements that receives fluorescence light from the sample to form the plurality of detected intermediate images of the sample that correspond to each of the plurality of structured multi-photon illumination patterns; and
    processing the plurality of detected intermediate images with a computing system that generates a reconstructed image of the sample.

15. The method of claim 14 further comprising controlling an array of mirror elements configured to scan a line of illumination onto the sample or scanning the sample with a multiline illumination device that couples a plurality of scanning lines onto the sample.

16. The method of claim 14 wherein the imaging device comprises a two dimensional pixelated imaging device.

17. The method of claim 14 wherein the computing system comprises one or more processors, at least one processor being configured to process the plurality of detected intermediate images and generate the reconstructed image and further comprising generating the reconstructed image by altering a spatial frequency to provide a plurality of illumination patterns using a selected pixel group.

18. The method of claim 14 further comprising processing a detected intermediate image represented as a Poisson distribution of a scattering function.

19. The method of claim 14 further comprising rotating an illumination beam relative to the sample with a rotation element.

20. The method of claim 14 further comprising:
    storing a plurality of preset structured illumination patterns in a memory;
    communicating each of the stored plurality of preset structured illumination patterns to the structured illumination system to thereby illuminate the sample; and
    processing the plurality of intermediate detected images with a reconstruction algorithm to reduce scattering using the preset structured illumination patterns, the reconstruction algorithm comprising a function of an excitation point spread function (PSF), a scattering PSF, and a modulation pattern.

21. A multi-photon temporal focusing microscopy system, comprising:
a light source that generates multi-photon illumination light;
a sample illumination system that couples the multiphoton illumination light onto a sample in a structured illumination pattern to induce fluorescence in the sample;
an imaging device having a plurality of detection elements; and
a computing system with a processor configured to execute instructions to:
select the structured illumination pattern from a plurality of stored illumination patterns;
configure the structured illumination system to modulate light from the light source using the selected structured illumination pattern, the modulated light illuminating the sample with the selected illumination pattern;
receive fluorescence light emitted or scattered from the sample at the plurality of detection elements of the imaging device to detect an intermediate image of the sample for each of the stored plurality of illumination patterns; and
generating a reconstructed image of the sample by performing a processing operation on the detected intermediate images of the sample corresponding to the illumination patterns.

22. The system of claim 21 further comprising an array of controlled mirror elements configured to scan a line of illumination onto the sample.

23. The system of claim 21 further comprising a multiline illumination device that couples a plurality of scanning lines onto the sample and an actuator that controls spatial locations of the scanning lines.

24. The system of claim 21 wherein the imaging device comprises a two dimensional pixelated imaging device to acquire the intermediate image for each illumination pattern and wherein the computing system comprises one or more processors, at least one processor being configured to process the detected intermediate images and generate the reconstructed image.

25. The system of claim 24 wherein the at least one processor is configured to generate the reconstructed image by altering a spatial frequency to provide a plurality of illumination patterns using a selected pixel group, and
wherein the at least one processor demodulates the detected intermediate images of the sample to provide the reconstructed image using the structured illumination patterns, and
wherein the at least one processor computes a single pixel value for each pixel group.

26. The system of claim 24 wherein a detected intermediate image is expressed as a Poisson distribution of a scattering function at a depth in the sample.

27. The system of claim 21 wherein the light source comprises a pulsed laser configured to generate two-photon excitation emission, or a three-photon excitation emission, that is coupled to the sample.

28. The system of claim 21 further comprising a spatial light modulator, or a digital micromirror device, that generates the structured illumination pattern.

29. The system of claim 21 further comprising:
an objective lens, the sample and the objective lens undergoing relative movement to select an imaging depth in the sample, and
a rotation element that rotates an illumination beam relative to the sample.

30. The system of claim 29 wherein the rotation element comprises a dove prism.

31. The system of claim 21 further comprising a grating or a diffractive optical element.

32. A multi-photon temporal focusing microscopy system, comprising:
an excitation source that generates multi-photon illumination light;
a structured illumination system including a spatial light modulator or a digital micromirror device;
an imaging device having a plurality of detection elements;
a computing system with a processor configured to execute instructions to:
select a structured illumination pattern based on a row of a Hadamard matrix;
configure the structured illumination system to modulate the multi-photon illumination light from the excitation source using the structured illumination pattern, the modulated light illuminating a sample to induce fluorescence;
receive light emitted or scattered from the sample at the plurality of detection elements of the imaging device to form an intermediate image;
collect additional intermediate images each corresponding to a different structured illumination pattern;
reconstruct a portion of a depth-selective image of the sample by performing an element-wise reassignment or demodulation operation on the intermediate image based on a stored preset structured illumination pattern.

33. The system of claim 32 wherein at least one structured illumination pattern is derived from a random pattern.

34. The system of claim 32 wherein the imaging device is pixelated and comprises a charge-coupled device (CCD), a complementary metal-oxide semiconductor (CMOS), or a multi anode photomultiplier tube (PMT) grid and wherein the system further comprises a multiline illumination system that illuminates the sample with a plurality of scanning lines.

35. The system of claim 32, further comprising a reconstruction algorithm that utilizes the structured illumination patterns.

36. The system of claim 32, wherein the instructions further comprise illuminating the sample to generate high spatial frequency image data and low spatial frequency image data wherein the sample is illuminated at a depth in the sample that is greater than at least one scattering length, or at least two scattering lengths, of light in the sample.

37. The system of claim 32, wherein the system comprises a wide field compressed sensing microscope.

38. The system of claim 34, wherein a reconstructed image is isotropic based on scanning in a plurality of orientations and wherein a pixel group of the pixelated imaging device comprises an n x n set of pixels and a central pixel is selected to reduce a scattering likelihood from neighboring pixels in the pixel group.

39. The system of claim 1 further comprising a beam shaping optical device to adjust a size of a beam of illuminating light from the light source that is directed onto the sample.

40. The system of claim 1 wherein a beam of light generated by the light source is separated into a plurality of components to temporally focus the plurality of components onto an imaging plane of the sample with a lens.

41. The method of claim 14 further comprising generating pulses of illuminating light and separating the illuminating light into a plurality of components to temporally focus the plurality of components onto an imaging plane of the sample with a lens.

42. The method of claim 14 further comprising adjusting a size of an illuminating beam of light with a beam shaping optical device.

* * * * *